United States Patent [19]

Sing et al.

[11] Patent Number: 4,826,532

[45] Date of Patent: May 2, 1989

[54] SUBSTITUTED 2,6-SUBSTITUTED PYRIDINE COMPOUNDS

[75] Inventors: Yuen-Lung L. Sing, St. Louis; Maria L. Miller, Manchester; Len F. Lee, St. Charles, all of Mo.

[73] Assignee: Monsanto Company, St. Louis, Mo.

[21] Appl. No.: 134,232

[22] Filed: Dec. 24, 1987

Related U.S. Application Data

[63] Continuation-in-part of Ser. No. 12,925, Feb. 9, 1987, abandoned.

[51] Int. Cl.[4] .................... C07D 401/02; A01N 43/40
[52] U.S. Cl. ................................ 71/94; 71/92; 546/275; 546/276; 546/278; 546/279; 546/281
[58] Field of Search ..................... 71/92, 94; 546/313, 546/316, 321, 315, 275, 278, 279, 276, 281

[56] References Cited

U.S. PATENT DOCUMENTS 4,692,184 9/1987 Lee ........................................ 546/318

Primary Examiner—Jane T. Fan
Attorney, Agent, or Firm—James C. Bolding

[57] ABSTRACT

Compounds of the formula

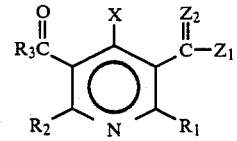

are disclosed as herbicides.

Disclosed herein are cyclic amides of pyridine 3,5-carboxylic acids substituted at the 2- and/or 6-position with a fluorinated methyl group. Also disclosed are herbicidal use of such compounds and compositions containing them.

15 Claims, No Drawings

SUBSTITUTED 2,6-SUBSTITUTED PYRIDINE COMPOUNDS

This is a continuation-in-part of application Ser. No. 012,925, filed 02/09/87 now abandoned.

This invention relates to a new class of 2,6-substituted pyridinecarboxylic acid derivatives having a wide range of activity as herbicides.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent 44,262 there are disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intravenous injection of such compounds.

Pyridine dicarboxylate compounds useful as herbicides are described in European Patent publication No. 133,612 published Feb. 27, 1985 which corresponds to U.S. application Ser. No. 612,021. These compounds have fluorinated methyl groups at the 2- and 6-positions and carboxylic acid derivative at the 3- and 5-positions.

Other pyridine dicarboxylate compounds including pyrazole amides are disclosed in European Patent publication No. 0182769, published May 28, 1986. This European publication corresponds to U.S. application Ser. No. 768,659.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

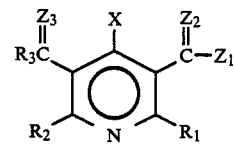

wherein:
$Z_1$ is selected from —SR, —OR,

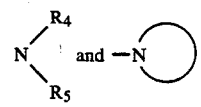

in which R is selected from the group consisting of hydrogen, lower alkyl, lower alkenyl, lower alkynyl, haloalkyl, haloalkenyl, and cyanoalkyl, and

is selected from azetidinyl and a nitrogen-containing heterocyclic ring moiety containing 5 atoms of which 1 to 4 may be nitrogen, optionally substituted with 1 to 3 groups selected from hydrogen, lower alkyl, lower alkoxy, cyano, halo, nitro, haloalkyl, alkoxyalkyl, dialkoxyalkyl, hydroxyalkyl, and formyl, and the heterocyclic ring is connected to carbon at one of its nitrogen atoms, and $R_4$ and $R_5$ are selected from hydrogen and lower alkyl;

$Z_2$ is selected from O, S and $NR_4$ in which $R_4$ is hydrogen or lower alkyl;

$Z_3$ is selected from O and $NR_4$;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

$R_3$ is

where

is as defined above; and
X is selected from lower alkyl, lower cycloalkyl, cycloalkylalkyl, alkoxyalkyl, and alkylthioalkyl.

The term "alkyl" means herein both straight and branched chain radicals having 1 to 7 carbon atoms which include, but are not limited to, ethyl, methyl, n-propyl, 1-ethylpropyl, 1-methylpropyl, n-butyl, 2,2-dimethylpropyl, pentyl, isobutyl, isopropyl.

The terms "lower alkenyl" and "lower alkynyl" herein means alkenyl and alkynyl groups having 3 to 7 carbon atoms. Examples of such alkenyl groups include 2-propenyl, 2-butenyl, 3-butenyl, 2-methyl-2-propenyl, and the like. Examples of such lower alkynyl groups include 2-propynyl, and so forth.

The term "haloalkyl" is intended to mean alkyl radicals substituted with one or more halogen atoms.

The term

as used herein includes radicals derived from imidazole, pyrazole, pyrrole, triazole, and tetrazole, including those with one to three methyl substituents.

The term "fluorinated methyl" means herein methyl radicals having one or more fluorine atoms attached thereto including radicals wherein all hydrogen atoms replaced by fluorine.

The term "chlorofluorinated methyl" means herein a methyl radical having at least one hydrogen replaced by fluorine and at least one other hydrogen replaced by chlorine.

DETAILED DESCRIPTION OF THE INVENTION

The compounds of this invention are readily prepared by reaction of a heterocyclic amine with the desired pyridinecarboxylic acid halide or pyridinedicarboxylic acid halide in the presence of a base (which may be an excess of the heterocyclic amine). Steps 1–9 which follow set out in detail the preparation of three specific acid halides which are used as starting materials for the compounds of this invention. Other acid halides may be readily prepared using the procedures of Steps 1–9 by varying the ketoester and aldehyde used in Step 1 to obtain the desired substituents in the pyridinedicarboxylate product. Other suitable pyridinedicarboxylate acid halides as starting materials are shown in European Patent publication No. 133,612 in Examples 44–51 and 82–83 inclusive. Other acid halide starting materials may be readily prepared using the techniques set out in that European Patent publication.

The following Steps 1–9 illustrate an example of the procedures for preparation of the acid halide compounds which are the starting materials for making the amides of the present invention. In these steps, a β-ketoester is reacted with an aldehyde to form a pyran (Step 1). The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4).

The ester groups of the pyridinedicarboxylate compound are the ester groups of the β-ketoester, and the 4-position of the pyridine is substituted with the same substituent as is on the aldehyde reagent.

When the pyridinedicarboxylate is substituted at the 2- or 6-position with a trifluoromethyl radical and at the other of these positions with a difluoromethyl radical, hydrolysis of the pyridine dicarboxylate compound occurs selectively on the side having the $CF_2H$ group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent the $CF_2H$ group.

STEP 1

Preparation of dimethyl 2,6-bis(trifluoromethyl)-2,6-dihydroxy-4-isobutyl-tetrahydro-3,5-pyrandicarboxylate To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p. 83°–87° C. and 14.51 g of a second crop, m.p. 67°–73° C.

The first crop is the desired product which contains a mixture of 5:1 cis and trans isomers.

Anal. Calc'd for $C_{15}H_{20}F_6O_7$: C, 42.26; H, 4.73; Found: C, 42.54; H, 4.77.

The second crop is a 2:1 mixture of cis and trans isomers. The mother liquor is concentrated to give 344 g of a residue which is a crude mixture of cis and trans isomer of the desired product.

STEP 2

Preparation of dimethyl 2,6-bis(trifluoromethyl)-2,6-dihydroxy-4-isobutyl-3,5-piperidinedicarboxylate To a solution of 344 g (0.920 mole) crude product from Step 1 in 500 ml of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°–106° C.

Anal. Calc'd for $C_{15}H_{21}F_6N_1O_6$: C, 42.36; H, 5.00; N, 3.29; Found: C, 42.84; H, 4.94; N, 3.29.

The mother liquor is concentrated to provide more of the crude desired product.

STEP 3

Preparation of a 2:1 mixture of dimethyl 2,6-bis(trifluoromethyl)-1,4-dihydro-4-isobutyl-3,5-pyridinedicarboxylate and its 3,4-dihydropyridine isomer To an ice water cooled mixture of 200 ml of concentrated sulfuric acid and 200 ml of methylene chloride is added 48.7 g (0.115 mole) of the product of Step 2 at once. The reaction mixture is stirred for 20 minutes and poured into 1 L. of ice water The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_D^{25}$ 1.4391.

Anal. Calc'd for $C_{15}H_{17}F_6N_1O_4$: C, 46.28; H, 4.40; N, 3.60; Found: C, 46.39; H, 4.44; N, 3.60.

Step 3 Product may be Prepared in Better Overall Yield Without Isolation of Step 1 and Step 2 Product by the Following Procedure To a mechanically stirred mixture of 340.3 g (1.98 mole) of 98.9% pure methyl trifluoroacetoacetate (MTFAA), 100 mL of toluene and 0.86 g (0.01 mol) of piperidine was added 90.5 g (1.03 mol) of isovaleraldehyde in 20 minutes. The reaction mixture exothermed causing a rise of temperature to 83° C. The reaction mixture was maintained at 80° C. for 3 hours. $^{19}$F NMR showed that the reaction was 89% complete. Heat was removed, and the reaction mixture was diluted with 125 mL of toluene and stirred overnight (16 hours). Gaseous ammonia was passed through the reaction mixture, the exotherm caused a rise of temperature to 68° C. in 50 minutes. A water cooling bath was applied to the reaction vessel to reduce the reaction temperature to 53° C. while ammonia was passed continuously. A total of 47.3 g (2.78 mol) of ammonia was passed in 1.5 hours. The reaction mixture was diluted with 100 mL of toluene. A Claisen distillation head was attached to the reaction vessel.

Excess ammonia and parts of toluene were removed in vacuo (water aspirator) while temperature was maintained at 26° C. An additional 200 mL of toluene was added, and the distillation was continued to remove a total of 200 mL of distillate in 1.5 hours. The reaction mixture was diluted with 100 mL of toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) of sulfuric acid was added, and the reaction mixture was stirred at 5° C. for 20 minutes before being poured into a mixture of 500 mL of toluene and 2 L of ice water. The toluene layer was separated and the aqueous layer was extracted once with 500 mL of toluene. The combined toluene extracts were washed successively with 500 mL of water, 500 mL of saturated aqueous NaHCO$_3$, 500 mL of brine and concentrated in vacuo to 363.6 g of an oil. GC area percent analysis indicated that the oil contained 9% of 3,4-dihydropyridine isomer and 75.4% of 1,4-dihydropyridine isomer corresponding to an overall yield of 82.9% from MTFAA.

STEP 4

Preparation of dimethyl 2-(difluoromethyl)-6-(trifluoromethyl)-4-isobutyl-3,5-pyridinedicarboxylate (a) Reaction of the Product of Step 3 with DBU A mixture of 23.0 g (0.0591 mole) of the product of Step 3, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried (MgSO$_4$) and concentrated to give 14.4 g of an oil which, according to $^1$H NMR, contained the desired product and acidic products. This oil is dissolved in ether and extracted with 100 ml of saturated sodium bicarbonate. The ether layer is dried (MgSO$_4$) and concentrated to give 8.9 g of an oil which is 71% pure desired product (by $^{19}$F NMR).

The sodium bicarbonate extract is acidified with concentrated HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from Step 3) of the desired product as an oil, n$_D^{25}$ 1.4478. This product crystallizes after standing, m.p. 36°–37° C.

Anal. Calc'd for C$_{15}$H$_{16}$F$_5$N$_1$O$_4$: C, 48.79; H, 4.37; N, 3.79; Found: C, 48.75; H, 4.39; N, 3.77.

The 71% pure desired product described previously was chromatographed by HPLC using 3% ethyl acetate/cyclohexane as eluent to give an earlier fraction (0.79 g, retention time 7–8.5 minutes) which was identified as methyl 6-(difluoromethyl)-4-(isobutyl)-2-(trifluoromethyl)-3-pyridinecarboxylate. The second fraction (retention time 8.5–18.5 minutes) is an additional 6.4 g (29.4%) of pure desired product, n$_D^{25}$ 1.4474.

(b) Reaction of the Product of Step 3 with Tributylamine

A mixture of 38.9 g of an 80% pure product of Step 3 and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to an 86% yield. This reaction can also be carried out in excess of tributylamine (10 equivalent) giving essentially similar results.

(c) Reaction of the Product of Step 3 with Tributylamine in Toluene

A mixture o 38.9 g of an 80% pure product of Step 3, 20.4 g of tributylamine and 30 ml of toluene is heated to 115° C. in 40 minutes and held at 115° C. for 1 hour and 40 minutes. The reaction mixture is cooled and worked up as in (b) above to give 36.3 g of a 76% pure product which corresponds to a 90% yield.

(d) Reaction of the Product of Step 3 with Triethylamine

A mixture of 11.8 g of an 80% pure product of Step 3 and 3.34 g of triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 with 2,6-Lutidine in the Presence of a Catalytic Amount of DBU A mixture of 5.0 g of product of Step 3 and 2.13 g of 2,6-lutidine is heated at 143° C. for 30 minutes. Two drops of DBU are added and the reaction mixture is heated for additional 1 hour and 30 minutes, cooled and worked up as in (b) above to give 4.23 g of the desired product. The reaction can also be carried out in excess of 2,6-lutidine and catalytic amount of DBU without solvent or in the presence of toluene as solvent giving similar results.

STEP 5

Preparation of 2-(difluoromethyl)-6-(trifluoromethyl)-4-isobutyl-3,5-pyridinedicarboxylic acid A 5-liter flask was charged with 894 g (2.42 mol) of the compound of Step 4 and 1 liter of water. To this was added a solution of 574 g (8.7 mol) of KOH in 800 ml of water. The mixture was refluxed overnight, after which HPLC showed that the reaction was complete. The flask was cooled to room temperature, acidified with HCl, and stirred until the organic phase solidified. The solids were filtered, washed with water, and dried in a fluid bed dryer. The diacid was obtained (756 g, 91.6% yield) as a brown solid.

STEP 6

Preparation of 3,5-bis-(chlorocarbonyl)-2-(difluoromethyl)-4-isobutyl-6-(trifluoromethyl)pyridine The diacid product of Step 5 (37.06 g, 0.108 mole) was refluxed with 150 ml $SOCl_2$ for three hours. At this time, $^{19}F$ NMR indicated the reaction was complete. The excess $SOCl_2$ was removed by rotary evaporation, leaving a dark oil which was the bis-acid chloride. This was Kugelrohr distilled at 100° C. to give a colorless oil.

STEP 7

Preparation of methyl 5-chlorocarbonyl-2-(difluoromethyl)-4-isobutyl-6-(trifluoromethyl)pyridine-3-carboxylate The product of Step 6 was then dissolved in 100 ml THF followed by 100 ml methanol. After 2½ hours the solvent was evaporated, leaving 31.2 g white solid, m.p. 71°–75° C. in 77% yield.

STEP 8

Preparation of 2-(difluoromethyl)-4-isobutyl-6-(trifluoromethyl)-3,5-pyridinedicarboxylic acid, 5-methyl ester A 1-liter 4-necked flask was charged with 300 gm of product of Step 4 and about 200 ml ethanol. In a separate flask was combined 59.14 g (0.896 mol) of 85% KOH and about 100 ml of water. The aqueous solution was poured into the organics and the flask was equipped with a mechanical stirrer, thermometer, nitrogen inlet and a water cooled conenser. The reaction mixture was heated to reflux, refluxed for 45 minutes and was cooled. The reaction mixture was concentrated and the concentrate was diluted with water and extracted once with ethyl ether. The ether extract (to remove starting material) was discarded. The aqueous solution was acidified with concentrated HCl and the orange precipitate that resulted was extracted with ethyl ether. (The aqueous solution was extracted with ether 3 times. The ether extracts were combined and dried over anhydrous magnesium sulfate, filtered and concentrated to yield 253.13 g (87.5% yield) of the monoacid acid.

STEP 9

Preparation of methyl 2-(difluoromethyl)-3-chlorocarbonyl-4-isobutyl-6-(trifluoromethyl)-5-pyridinecarboxylate The acid (253 g 0.7121 mol) from Step 8 was refluxed for 24 hours in approximately 250–300 ml of thionyl chloride. The reaction mixture was concentrated to yield 244.59 g of acid chloride in 91.9% yield. $n_D^{25}$ 1.4614.

In compounds of the invention where the $Z_1$ group is SR, a thiol is substituted for the alcohol for reaction with the acid chloride. Where the $Z_1$ group is

one of the 5-membered heterocyclic amines is employed for reaction with the acid chloride.

In compounds of this invention where the $Z_2$ group is $NR_4$, the carboxamide is reacted with thionyl chloride to form a chloroimide followed by the reaction with an alcohol, thiol, or heterocyclic amine containing the $Z_1$ group as above.

Preparation of compounds of this invention will become clear by reference to the following examples.

As used throughout the specification, including the Examples, the following abbreviations have the following meanings:

THF—tetrahydrofuran
HPLC—high pressure liquid chromatography
TLC—thin layer chromatography
RT—room temperature
DBU—1,8-diazabicyclo-[5.4.0]-undec-5-ene

EXAMPLE 1

3-Pyridinecarboxylic acid, 2-(difluoromethyl)-5-[(1H-imidazol-1-yl)carbonyl]-4-(2-methylpropyl)-6-(trifluoromethyl)-, methyl ester Methyl 5-(chlorocarbonyl)-2-(difluoromethyl)-4-(2-methylpropyl)-6-(trifluoromethyl)-3-pyridinecarboxylate (5.15 g, 0.0138 mole), 50 ml THF and 2.09 g imidazole were combined at room temperature. After a few minutes a solid began to form. After 1½ hours a gas chromatographic assay showed the reaction was complete. The solid was filtered off and washed with THF. The THF was evaporated to give 6.0 g of an oil. This oil was purified by HPLC (20% EtOAc/cyclohexane) and then kugelrohr distilled at 104° C. to give 4.1 g of product as a yellowish oil. 73% yield

EXAMPLE 2

3-Pyridinecarboxylic acid, 2-(difluoromethyl)-4-(2-methylpropyl)-5-[(1H-pyrazol-1-yl)carbonyl]-6-(trifluoromethyl), methyl ester Methyl 5-(chlorocarbonyl)-2-(difluoromethyl)-4-(2-methylpropyl)-6-(trifluoromethyl)-3-pyridinecarboxylate (2.09 g, 0.0056 mole), 50 ml $CH_2Cl_2$ and 0.88 g (0.013 mole) of pyrazole were combined at ice bath temperature. After 1 hour there was no reaction. The $CH_2Cl_2$ was evaporated and replaced by 30 ml $CCl_4$. An additional 0.35 g of pyrazole was added. This mixture was refluxed overnight. $^{19}F$ nmR showed ~10% starting material and the remainder product. The reaction mixture was washed with $H_2O$ and extracted with $CH_2Cl_2$. The $CH_2Cl_2$ layer was dried with $MgSO_4$, filtered and concentrated to a nearly colorless oil. This was purified by chromatography in 40% $CH_2Cl_2$/cyclohexane to give 1.9 g colorless oil, which gradually solidified, m.p. 49°–52° C., 87% yield.

EXAMPLE 3

3-Pyridinecarboxylic acid, 2-(difluoromethyl)-4-(2-methylpropyl)-5-(1-pyrrolidinylcarbonyl)-6-(trifluoromethyl)-, methyl ester Methyl 5-(chlorocarbonyl)-2-(difluoromethyl)-4-(2-methylpropyl)-6-(trifluoromethyl)-3-pyridinecarboxylate (3.3 g, 0.0088 mole) and 100 ml $CH_2Cl_2$ were combined and cooled in an ice bath before adding 2 ml of pyrrolidine by pipet. The ice bath was removed, and the reaction mixture was stirred at room temperature for 4 hours. A gas chromatograph assay showed that the reaction was complete. The product mixture was washed with H$_2$O and extracted with CH$_2$Cl$_2$. The CH$_2$Cl$_2$ layer was dried with MgSO$_4$, filtered and concentrated to yield about 4 grams of a yellow solid which was recrystallized from about 10% EtOAc/hexane to give 2.92 g of off-white crystals, m.p. 117°–120° C., 80% yield.

Using similar procedures, the following amides were prepared. A physical property is shown for each.

TABLE 1

| Example | Name | M.P. (°C.) | B.P. (°C.) | $n_D^{25}$ |
|---|---|---|---|---|
| 4 | 3-pyridinecarbothioic acid, 6-(difluoromethyl)-4-(2-methylpropyl)-5-[(3-methyl-1H—pyrazol-1-yl)carbonyl]-2-(trifluoromethyl)-, S—methyl ester mixture with S—methyl 6-(difluoromethyl)-4-(2-methylpropyl)-5-[(5-methyl-1H—pyrazol-1-yl)carbonyl]-2-(trifluoromethyl)-3-pyridinecarbothioate | | 130 @ 0.100 torr | |
| 5 | 3-pyridinecarbothioic acid, 6-(difluoromethyl)-4-(2-methylpropyl)-5-[(1H—pyrazol-1-yl)carbonyl]-2-(trifluoromethyl)-, S—methyl ester | | 130 @ 0.100 torr | |
| 6 | 3-pyridinecarboxylic acid, 6-(difluoromethyl)-4-(2-methylpropyl)-5-[(1H—pyrazol-1-yl)carbonyl]-2-(trifluoromethyl)-, methyl ester | | | 1.4860 |
| 7 | 3-pyridinecarboxylic acid, 6-(difluoromethyl)-4-(2-methylpropyl)-5-[(3-methyl-1H—pyrazol-1-yl)carbonyl]-2-(trifluoromethyl)-, methyl ester mixture with methyl 6-(difluoromethyl)-4-(2-methylpropyl)-5-[(5-methyl-1H—pyrazol-1-yl)carbonyl]-2-(trifluoromethyl)-3-pyridinecarboxylate | | | 1.487 |
| 8 | pyridine, 2-(difluoromethyl)-4-(2-methylpropyl)-3,5-bis[(1H—pyrazol-1-yl)carbonyl]-6-(trifluoromethyl) | | 140 @ 0.100 torr | |
| 9 | 3-pyridinecarboxylic acid, 6-(difluoromethyl)-5-[(methylimino)-1H—pyrazol-1-ylmethyl]-4-(2-methylpropyl)-2-(trifluoromethyl)-, methyl ester | | | 1.4946 |
| 10 | 3-pyridinecarbothioic acid, 2-(difluoromethyl)-4-(2-methylpropyl)-5-[(1H—pyrazol-1-yl)carbonyl]-6-(trifluoromethyl)-, S—methyl ester | 110.0–113.0 | | |
| 11 | 3-pyridinecarboxylic acid, 6-(difluoromethyl)-5-[(3,5-dimethyl-1H—pyrazol-1-yl)carbonyl]-4-(2-methylpropyl)-2-(trifluoromethyl)-, methyl ester | | | 1.4867 |
| 12 | 3-pyridinecarboxylic acid, 2-(difluoromethyl)-5-[(3,5-dimethyl-1H—pyrazol-1-yl)carbonyl]-4-(2-methylpropyl)-6-(trifluoromethyl)-, methyl ester | | | 1.4865 |
| 13 | 3-pyridinecarboxylic acid, 4-cyclobutyl-2-(difluoromethyl)-5-[(1H—pyrazol-1-yl)carbonyl]-6-(trifluoromethyl)-, methyl ester | 101.0–102.0 | | |
| 14 | 3-pyridinecarboxylic acid, 4-cyclobutyl-2-(difluoromethyl)-5-[(3-methyl-1H—pyrazol-1-yl)carbonyl]-6-(trifluoromethyl)-, methyl ester mixture with methyl 4-cyclobutyl-2-(difluoromethyl)-5-[(5-methyl-1H—pyrazol-1-yl)carbonyl]-6-(trifluoromethyl)-3-pyridinecarboxylate | 98.0–100.0 | | |
| 15 | 3-pyridinecarboxylic acid, 6-(difluoromethyl)-4-methyl-5-[(1H—pyrazol-1-yl)carbonyl]-2-(trifluoromethyl)-, methyl ester | 100.0–102.0 | | |
| 16 | 3-pyridinecarboxylic acid, 6-(difluoromethyl)-4-[(methylthio)methyl]-5-[(1H—pyrazol-1-yl)carbonyl]-2-(trifluoromethyl)-, ethyl ester | 63.0–65.0 | | |
| 17 | pyridine, 3,5-bis[(1H—pyrazol-1-yl)carbonyl]-2-(difluoromethyl)-4-[(methylthio)methyl]-6-(trifluoromethyl)- | | 170.0–180.0 @ 1.500 torr | |
| 18 | 3-pyridinecarbothioic acid, 2-(difluoromethyl)-4-[(methylthio)methyl]-5-[(1H—pyrazol-1-yl)carbonyl]-6-(trifluoromethyl)-, S—methyl ester | 103.0–105.0 | | |
| 19 | 3-pyridinecarboxylic acid, 2-(difluoromethyl)-4-(2-methylpropyl)-5-[(3-methyl-1H—pyrazol-1-yl)carbonyl[-6-(trifluoromethyl)-, methyl ester, mixture with methyl 2-(difluoromethyl)-4-(2-methylpropyl)-5-[(5-methyl-1H—pyrazol-1-yl)carbonyl]-6-(trifluoromethyl)-3-pyridinecarboxylate | | | 1.4877 |
| 20 | 3-pyridinecarboxylic acid, 2-(difluoromethyl)-5-[(methylimino)(1H—pyrazol-1-yl)methyl]-4-(2-methylpropyl)-2-(trifluoromethyl)-, methyl ester | | | 1.497 |
| 21 | 3-pyridinecarboxylic acid, 2-(difluoromethyl)-5-[(1H—imidazol-1-yl)(methylimino)methyl]-4-(2-methylpropyl)-6-(trifluoromethyl)-, methyl ester | | 135 @ 0.100 torr | |
| 22 | 3-pyridinecarboxylic acid, 2-(difluoromethyl)-4-(1-methylpropyl)-5-[(1H—1,2,4-triazol-1-yl)carbonyl]-6-(trifluoromethyl)-, methyl ester | | | 1.4836 |
| 23 | 3-pyridinecarboxylic acid, 6-(difluoromethyl)-4-(2-methylpropyl)-5-[(1-pyrrolidinyl)carbonyl]- | 94.0–97.0 | | |

TABLE 1-continued

| Example | Name | M.P. (°C.) | B.P. (°C.) | $n_D^{25}$ |
|---|---|---|---|---|
| | 2-(trifluoromethyl)-, methyl ester | | | |
| 24 | 3-pyridinecarboxylic acid, 6-(difluoromethyl)-4-(2-methylpropyl)-5-[(4-methyl-1H—pyrazol-1-yl)carbonyl]-2-(trifluoromethyl)-, methyl ester | | | 1.487 |
| 25 | 3-pyridinecarboxylic acid, 6-(difluoromethyl)-4-(cyclopropylmethyl)-5-[(1H—pyrazol-1-yl)carbonyl]-2-(trifluoromethyl)-, methyl ester | | | 1.4990 |
| 26 | 3-pyridinecarboxylic acid, 2-(difluoromethyl)-4-(cyclopropylmethyl)-5-[(1H—pyrazol-1-yl)carbonyl]-6-(trifluoromethyl)-, methyl ester | | 130 @ 0.100 torr | |
| 27 | methanamine, N—{[2-(difluoromethyl)-4-(2-methylpropyl)-5-[(1H—pyrazol-1-yl)carbonyl]-6-(trifluoromethyl)-3-pyridinyl](methylthio)methylene} | | | 1.5176 |
| 28 | 3-pyridinecarboxylic acid, 6-(difluoromethyl)-4-(2-methylpropyl)-5-[(1H—pyrrol-1-yl)carbonyl]-2-(trifluoromethyl)-, methyl ester | 90.0–95.0 | | |
| 29 | 3-pyridinecarboxylic acid, 2-(difluoromethyl)-4-(2-methylpropyl)-5-[(1H—pyrrol-1-yl)carbonyl]-6-(trifluoromethyl)-, methyl ester | 95.0–99.0 | | |
| 30 | 3-pyridinecarboxylic acid, 6-(difluoromethyl)-4-(2-methylpropyl)-5-[(1H—1,2,3,5-tetrazol-1-yl)carbonyl]-6-(trifluoromethyl)-, methyl ester | 100.0–105.0 | | |
| 31 | 3-pyridinecarboxylic acid, 2-(difluoromethyl)-4-(2-methylpropyl)-5-[(2H—1,2,3,4-tetrazol-2-yl)carbonyl]-6-(trifluoromethyl)-, methyl ester | 96.0–98.0 | | |
| 32 | 3-pyridinecarboxylic acid, 2-(fluoromethyl)-4-(2-methylpropyl)-5-[ (1H—pyrazol-1-yl)carbonyl]-6-(trifluoromethyl)-, methyl ester | | 145–155 @ 1.300 torr | |

EXAMPLE 33

3-Pyridinedithioic acid, 2-(difluoromethyl)-4-(2-methylpropyl)-5-(1H-pyrazol-1-ylcarbonyl)-6-(trifluoromethyl)-, methyl ester A solution of 4.26 g (0.010 mole) of 3-pyridinecarboxylic acid, 2-(difluoromethyl)-4-(2-methylpropyl)-5-(1H-pyrazol-1-ylcarbonyl)-6-(trifluoromethyl)-, methyl ester, 4.9 g (0.012 mole) of Lawesson's Reagent, and 8.3 mL of hexamethylphosphoramide in 75 mL of xylenes was heated to reflux for 16 hours. The solution was cooled and passed through a silica gel pad using 10% ethyl acetate in cyclohexane. Chromatographic purification followed by crystallization from hexanes/ethyl acetate yielded 1.6 g (35%) of the title compound as orange crystals (m.p. 124.5°–125.5° C.). Anal. Calcd for $C_{17}H_{16}F_5N_3O_1S_2$: C, 46.67; H, 3.69; N, 9.60. Found: C, 46.14; H, 3.96; N, 9.20.

EXAMPLE 34

1H-Pyrazole, 1[[5-cyano-6-(difluoromethyl)-4-(2-methylpropyl)-2(trifluoromethyl)-3-pyridinal]carbonyl]-

A solution of 7.0 g (0.018 mole) of 3-pyridinecarboxamide, 2-(difluoromethyl)-4-(2-methylpropyl)-5-(1H-pyrazol-1-ylcarbonyl)-6-(trifluoromethyl)-, in 50 mL of $POCl_3$ was refluxed for 4 hours. The solution was concentrated, taken up in water, and extracted with dichloromethane. The organics were dried over $MgSO_4$, filtered, and concentrated to give 7.8 g of light brown oil. Kugelrohr distillation gave 4.95 g (74%) of the title compound as a pale yellow oil which solidified upon standing (m.p. 74°–75° C.). Anal. Calcd for $C_{16}H_{13}F_5N_4O_1$: C, 51.61; H, 3.52; N, 15.04. Found: C, 51.03; H, 3.48; N, 14.99.

EXAMPLE 35

3-Pyridinecarboxylic Acid, 4-(cyclopropylmethyl)-2-(difluoromethyl)-5-[(3-fluoro-1H-pyrazol-1-yl)carbonyl]-6-(trifluoromethyl)-, methyl ester A 2.0 g (0.0054 mole) sample of 3-pyridinecarboxylic acid, 5-(chlorocarbonyl)-4-(cyclopropylmethyl)-2-(difluoromethyl)-6-(trifluoromethyl)-, methyl ester in 20 mL of anhydrous THF was placed in a dry addition funnel. An oven dried 3-neck round bottomed flask was charged with 0.47 g (0.0054 mole) of 3-fluoropyrazole and 25 mL of anhydrous THF and cooled to 5° C. Then was added 6 mL of 1M sodium bis(trimethylsilyl)amide. The acid chloride was dripped in over 10 minutes. The ice bath was removed and after 10 minutes GLC assay showed no starting material. The solution was poured into dilute HCl and extracted with ethyl ether. The organics were dried over $MgSO_4$, filtered, concentrated, and purified using a chromatograph (5:1 hexanes to ethyl acetate) to afford 1.1 g (57%) of the title compound as a white solid (m.p. 57°–58° C.). Anal. Calcd for $C_{17}H_{13}F_6N_3O_3$: C, 48.47; H, 3.11; N, 9.97. Found: C, 48.49; H, 3.18; N, 9.85.

EXAMPLE 36

3-Pyridinecarboxylic Acid, 2-(difluoromethyl)-4-(2-methylpropyl)-5-(1H-pyrazol-1-ylcarbonyl)-6-(trifluoromethyl)-, cyanomethyl ester To a solution of 4.46 g (0.0109 mole) of 3-pyridinecarbonyl chloride, 2-(difluoromethyl)-4-(2-methylpropyl)-5-(1H-pyrazol-1-ylcarbonyl)-6-(trifluoromethyl)-, in 20 mL of anhydrous DMF was added 2.72 g (0.0272 mole) of anhydrous potassium bicarbonate. The resulting solution was stirred for one hour under nitrogen until $CO_2$ evolution ceased. Bromoacetonitrile (0.91 mL, 0.0131 mole) was added and the reaction was stirred at room temperature overnight. The reaction mixture was poured into 150 mL of water and the resulting solution was extracted with ether. The ether extracts were washed with brine and dried over anhydrous magnesium sulfate. Concentration gave a solid which was recrystallized from methylene chloride-hexanes to give 4.12 g (88%) of the title compound as tan crystals (MP 117°–119° C.). Anal. Calcd for $C_{18}H_{15}F_5N_4O_3$: C, 50.24; H, 3.51; N, 13.02. Found: C, 50.33; H, 3.55; N, 13.00.

EXAMPLE 37

3-Pyridinecarboxylic Acid, 2-(chlorodifluoromethyl)-6-(1-methylethyl)-4-(2-methylpropyl)-5-(1H-pyrazol-1-ylcarbonyl)-, methyl ester To a solution of 240 g of t-butyl isobutyrylacetate in 500 mL of methanol was passed 70 g of ammonia in 2 hours, maintaining the temperature at below 25° C. The resulting solution was stirred at room temperature for 18 hours, after which methanol was removed in vacuo. Methylene chloride was added and the suspension was filtered. The filtrate was concentrated on a rotary evaporator to give 180 g of t-butyl 3-amino-4-methyl-2-pentenoate as an oil.

A solution of 18.6 g (0.1 mol) of methyl chlorodifluoroacetoacetate, 8.4 g (0.1 mol) of isobutyraldehyde and 20.5 g (0.1 mol) of t-butyl 3-amino-4-methyl-2-pentenoate in 80 mL of THF containing 1 mL of piperidine was refluxed for 18 h. Then the solution was concentrated in vacuo to give 46 g of crude oil.

To a solution of 27 g of the above crude oil and 20 mL of DBU in 80 mL of methylene chloride was added dropwise 9 mL of trifluoroacetic anhydride below 10° C. and the resulting solution was stirred at room temperature for 18 h. Water was addded and the two layers were separated. The organic layer was washed with 2N HCl, water, and brine, then dried and concentrated to give 22 g of crude 3-methyl 5-(1,1-dimethylethyl) 2-(chlorodifluoromethyl)-1,4-dihydro-6-(1-methylethyl)-4-(2-methylpropyl)-3,5-pyridinedicarboxylate as an oil.

To a solution of 11 g of the above crude dihydropyridine in 120 mL of methylene chloride was added in portions 12 g of 2,3-dichloro-5,6-dicyano-1,4-benzoquinone (DDQ) keeping the reaction temperature at 20°–30° C. and then stirred at room temperature for 3 h, after which the suspension was filtered and the cake was washed thoroughly with methylene chloride. The filtrate was washed with saturated sodium dicarbonate solution brine, dried and concentrated. Column chromatography on silica gel (2% ethylacetate-cyclohexane) gave 7.8 g of crude 3-methyl 5-(1,1-dimethylethyl) 2-(chlorodifluoromethyl)-6-(1-methylethyl)-4-(2-methylpropyl)-3,5-pyridinedicarboxylate as an oil.

A solution of 2.5 g (6 mmol) of the above crude pyridinedicarboxylate in 9 mL of trifluoroacetic acid was stirred at RT for 18 h. Water and $CH_2Cl_2$ were added and the two layers were separated. The $CH_2Cl_2$ solution was washed with $H_2O$ and brine, then dried and concentrated to give the monoacid. The acid was refluxed in 20 mL of oxalyl chloride for 2 h, after which the excess oxalyl chloride was removed in vacuo to give crude 3-methyl 2-(Chlorodifuloromethyl)-5-(chlorocarbonyl)-6-(2-methylethyl)-4-(2-methylpropyl)-3-pyridinecarboxylate. The acid chloride was dissolved in 20 mL $CH_2Cl_2$ and 1.2 g (18 mmol) of pyrazole was added in 1 portion and stirred at RT for 18 h. $H_2O$ was added. The organic layer was separated and washed with brine, dried and concentrated. Column chromatography on silica gel (3% ethyl acetate-cyclohexane) gave 1.4 g (56%) of the product as a colorless oil, $n_D^{25}$ 1.5024. Anal Calcd for $C_{19}H_{22}Cl_1F_2N_3O_3$: C, 55.14; H, 5.32; N, 10.16. Found: C, 54.67; H, 5.37; N, 9.78.

EXAMPLE 38

3-Pyridinecarboxylic Acid, 2-(difluoromethyl)-6-(1-methylethyl)-4-(2-methylpropyl)-5-(1H-pyrazol-1-ylcarbonyl)-, methyl ester Step 1: A solution of 17 g (40 mmol) of crude 3-methyl 5-(1,1-dimethylethyl) 2-(chlorodifluoromethyl)-6-(1-methylethyl)-4-(2-methylpropyl)-3,5-pyridinedicarboxylate and 7 mL of triethylamine in 160 mL of ethanol was subjected to hydrogenolysis at ambient temperature and 2 atom pressure in the presence of 3 g of 5% palladium on charcoal for 18 hours. The suspension was filtered through celite and concentrated. Water and $CH_2Cl_2$ were added. The $CH_2Cl_2$ layer was separated, washed with $H_2O$, dried and concentrated. Column chromatography on silica gel (2% ethyl acetate/cyclohexane) gave 14 g (91%) of 5-(1,1-dimethylethyl) 3-methyl 2-(difluoromethyl)-6-(1-methylethyl)-4-(2-methylpropyl)-3,5-Pyridinedicarboxylate as colorless oil, $n_D^{25}$ 1.4713.

Step 2: A solution of 5.4 g (14 mmol) of the above pyridinedicarboxylate in 25 mL of trifluoroacetic acid was stirred at room temperature for 18 hours. After which trifluoroacetic acid was removed. $H_2O$ and $CH_2Cl_2$ were added and separated. The organic layer was washed with $H_2O$, brine, dried and concentrated to give a monoacid. The monoacid in 30 mL of oxalyl chloride containing 3 drops of dimethylformamide was heated under reflux for 6 hours. Then the excess oxalyl chloride was removed in vacuo to give crude 3-methyl 5-(chlorocarbonyl)-2-(difluoromethyl)-6-(2-methylethyl)-4-(2-methylpropyl)-3-pyridinecarboxylate. To the above crude acid chloride in 10 mL of $CH_2Cl_2$ was added 2 g of pyrazole and 4 mL of triethylamine at 0° C. and the reaction solution was stirred at room temperature for 18 hours. $H_2O$ was added. The organic layer was separated, washed with $H_2O$, brine, dried and concentrated. Column chromatography on silica gel (5% ethyl acetate-cyclohexane) gave 2.9 g (55%) of colorless oil, $N_{D25}$ 1.5082.

Anal. Calc'd. for $C_{19}H_{23}F_2N_3O_3$: C, 60.12; H, 6.07; N, 11.08; Found: C, 59.76; H, 6.09; N, 10.93.

EXAMPLE 39

3-Pyridinecarboxylic acid, 2-(dichloromethyl)-4-(2-methylpropyl)-5-(1H-pyrazole-1-ylcarbonyl)-6-(trifluoromethyl)-, methyl ester Product of Example 2 (3.5 g at 93% assay) in about 50 mL of methylene chloride was mixed with 3.5 g of fresh $AlCl_3$. The Mixture was stirred several hours whereupon most material had reacted. Overnight stirring produced some chloroactone. The material was poured into ice/37% HCl, and extracted with more methylene chloride. After evaporating solvent, Kugelrohr distillation gave 2.9 g of an oil, which was subjected to HPLC with 6% EtOAc in cyclohexane to give 1.8 g of product containing starting material and chloroactone. This was separated by Kugelrohr distillation collecting starting material as fraction 1 up to 132° C. at 1 mm. Fraction 2, bp 132°–175° C. at 1 mm, is the desired product, $n_D^{25} = 1.5175$. Anal. Calc'd. for $C_{17}H_{16}Cl_2F_3N_3O_3$: C, 46.59, H, 3.68, N, 16.18; Found: C, 46.80, H, 3.75, N, 16.01.

TABLE 2

| Example | Name | M.P. (°C.) | B.P. (°C.) | $n_D^{25}$ |
|---|---|---|---|---|
| 40 | 3-Pyridinecarbonyl chloride, 2-(difluoromethyl)-4-(2-methylpropyl)-5-(1H—pyrazol-1-ylcarbonyl)-6-(trifluoromethyl)- | 83–84° C. | | |
| 41 | 3-Pyridinecarboxylic acid, 5-(1-azetidinylcarbonyl)-6-(difluoromethyl(-4-(2-methylpropyl)-2-(trifluoromethyl)-, methyl ester | 94–96° C. | | |
| 42 | 3-Pyridinecarboxylic acid, 5-(1-azetidinylcarbonyl)-2-(difluoromethyl)-4-(2-methylpropyl)-6-(trifluoromethyl)-, methyl ester | 100–101° C. | | |
| 43 | 3-Pyridinecarboxylic acid, 5-(1-azetidinyl carbonyl)-4-(cyclopropylmethyl)-2-(difluoromethyl)-6-(trifluoromethyl)-, methyl ester | 123–124° C. | | |
| 44 | 3-pyridinecarbothioic acid, 4-(cyclopropylmethyl)-2-(difluoromethyl)-5-(1H—pyrazol-1-ylcarbonyl)-6-(trifluoromethyl)-, S—methyl ester | 113–114° C. | | |
| 45 | 3-Pyridinecarboxamide, 2-(difluoromethyl)-4-(2-methylpropyl)-5-(1H—pyrazol-1-ylcarbonyl)-6-(trifluoromethyl)- | 217–218° C. | | |
| 46 | 3-Pyridinecarboxylic acid, 5-[(4-cyano-1H—pyrazol-1-yl)carbonyl]-2-(difluoromethyl)-4-(2-methylpropyl)-6-(trifluoromethyl)-, methyl ester | 74–76° C. | | |
| 47 | 3-Pyridinecarboxylic acid, 5-[(4-chloro-1H—pyrazol-1-yl)carbonyl]-2-(difluoromethyl)-4-(2-methylpropyl)-6-(trifluoromethyl)-, methyl ester | 75–76° C. | | |
| 48 | 3-Pyridinecarboxylic acid, 2-(difluoromethyl)-5-[(4-methoxy-1H—pyrazol-1-yl)carbonyl]-4-(2-methylpropyl)-6-(trifluoromethyl)-, methyl ester | 60–62° C. | | |
| 49 | 3-Pyridinecarboxylic acid, 2-(difluoromethyl)-4-(2-methylpropyl)-5-(1H—pyrazol-1-ylcarbonyl)-6-(trifluoromethyl)-, 2-fluoroethyl ester | | | 1.4830 |
| 50 | 3-Pyridinecarboxylic acid, 4-(cyclopropylmethyl)-2-(difluoromethyl)-5-[(3-ethyl-1H—pyrazol-1-yl)carbonyl] -6-(trifluoromethyl)-, methyl ester, mixture with methyl 4-(cyclopropylmethyl)-2-(difluoromethyl)-5-[(5-ethyl-1H—pyrazol-1-yl)carbonyl]-6-(trifluoromethyl)-3-pyridinecarboxylate | | | 1.4955 |
| 51 | 3-Pyridinecarboxylic acid, 4-(cyclopropylmethyl)-2-(difluoromethyl)-5-(4-nitro-1H—pyrazol-1-yl)-6-(trifluoromethyl)-, methyl ester | 99–100° C. | | |
| 52 | 3-Pyridinecarboxylic acid, 2-(difluoromethyl)-5-[(3-fluoro-1H—pyrazol-1-yl)carbonyl]-4-(2-methylpropyl)-6-(trifluoromethyl)-, methyl ester | | 120° C. @ 0.47 mm Hg | |
| 53 | 3-Pyridinecarboxylic acid, 2-(difluoromethyl)-5-[(3-ethyl-1H—pyrazol-1-yl)carbonyl]-4-(2-methylpropyl)-6-(trifluoromethyl)-, methyl ester, mixture with methyl 2-(difluoromethyl)-5-[(5-ethyl-1H—pyrazol-1-yl)carbonyl]-4-(2-methylpropyl)-6-(trifluoromethyl)-3-pyridinecarboxylate | | | 1.4845 |
| 54 | 3-Pyridinecarboxylic acid, 4-(cyclopropylmethyl)-2-(difluoromethyl)-5-[3-(1-methyethyl)-1H—pyrazol-1-yl)carbonyl]-6-(trifluoromethyl)-, methyl ester, mixture with methyl 4-(cyclopropylmethyl)-2-(difluoromethyl)-5-[5-(1-methylethyl)-1H—pyrazol-1-yl)carbonyl]-6-(trifluoromethyl)-3-pyridinecarboxylate | | | 1.4898 |
| 55 | 3-Pyridinecarboxylic acid, 2-(difluoromethyl)-4-(2-methylpropyl)-5-[(4-nitro-1H—pyrazol-1-yl)carbonyl]-6-(trifluoromethyl)-, methyl ester | 90–91° C. | | |
| 56 | 3-Pyridinecarbothioic acid, 4-cyclobutyl-2-(difluoromethyl)-5-(1H—pyrazol-1-ylcarbonyl)-6-(trifluoromethyl)-, S—methyl ester | | | 1.5349 |
| 57 | 3-Pyridinecarboxylic acid, 2-(difluoromethyl)-5-[[3-(dimethoxymethyl)-1H—pyrazol-1-yl]carbonyl]-2-(methylpropyl)-6-(trifluoromethyl)-, methyl ester | | | 1.484 |
| 58 | 3-Pyridinecarboxylic acid, 2-(difluoromethyl)-5-[(3-formyl-1H—pyrazol-1-yl)carbonyl]-4-(2-methylpropyl)-6-(trifluoromethyl)-, methyl ester | 97–97.5 | | |
| 59 | 3-Pyridinecarboxylic acid, 2-(difluoromethyl)-5-[[3-(difluoromethyl)-1H—pyrazol-1-yl]carbonyl]-4-(2-methylpropyl)-6-(trifluoromethyl)-, methyl ester | | | 1.474 |
| 60 | 3-Pyridinecarboxylic acid, 2-(difluoromethyl)-5-[[3-(hydroxymethyl)-1H—pyrazol-1-yl]carbonyl]-4-(2-methylpropyl)-6-(trifluoromethyl)-, methyl | | | 1.4974 |

TABLE 2-continued

| Example | Name | M.P. (°C.) | B.P. (°C.) | $n_D^{25}$ |
|---|---|---|---|---|
| | ester | | | |

PRE-EMERGENT HERBICIDE EXAMPLES

As noted above, compounds of this invention have been found to be effective as herbicides, particularly pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The herbicide rating symbols in Tables A and B are defined as follows:

| % Inhibition | Rating |
|---|---|
| 0–24 | 0 |
| 25–49 | 1 |
| 50–74 | 2 |
| 75–100 | 3 |
| Not planted | — |
| Species planted, no data | N or a blank |

For some compounds of this invention data were orginally recorded as percent inhibition (or control) in ten percent increments. Where this system was used, the percentages have been mathematically converted to the above equivalent system using the correlation table above.

PRE-EMERGENT ACTIVITY ON WEEDS

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amount of active ingredient was equivalent to an application rate of 11.2 kg/ha. After treatment, the pans were moved to a greenhouse bench where they were watered as needed to give adequate moisture for germination and growth.

Approximately 10–14 days (usually 11 days) after planting and treating, the pans were observed and the results recorded. In some instances, a second observation was made approximately 24–28 days after seeding and treating, and these observations are indicated in the following tables by a "pound" (#) sign immediately following the Example number.

The plant species usually regarded as weeds which were utilized in one set of pre-emergent activity test, the data for which are shown in Table A, are identified by letter headings printed diagonally above the columns according to the following legend:

| | |
|---|---|
| CATH — | Canada thistle* |
| COBU — | Cocklebur |
| VELE — | Velvetleaf |
| MOGL — | Morningglory |
| COLQ — | Common Lambsquarters |
| PESW — | Pennsylvania Smartweed |
| YENS — | Yellow Nutsedge* |
| RHJG — | Rhizome Johnsongrass* |
| SEJG — | Seedling Johnsongrass |
| RHQG — | Quackgrass* |
| DOBR — | Downy Brome |
| BYGR — | Barnyardgrass |
| ANBG — | Annual Bluegrass |
| INMU — | Indian Mustard |
| WIBW — | Wild Buckwheat |

*Group from vegetative propagules

In Table A, the first column is the application rate of the compound being tested in kg/ha. Where applicable, the footnotes follow the Table.

TABLE A

| Ex. No. | Rate kg/ha | Yens | Anbg | Sejg | Dobr | Bygr | Mogl | Colq | Vele | Inmu | Wibw | Cath | Cobu | Pesw | Rhqg | Rhjg |
|---|---|---|---|---|---|---|---|---|---|---|---|---|---|---|---|---|
| 1 | 11.2100 | 1 | | | 3 | 3 | 3 | 1 | 3 | | | 3 | 3 | 3 | 3 | 1 |
| 2 | 11.2100 | 3 | | | 3 | 3 | 3 | 3 | 3 | | | 3 | 3 | 3 | 3 | 3 |
| 3 | 11.2100 | 1 | | | — | 3 | 3 | 0 | 3 | | | 3 | 3 | 3 | 3 | 3 |
| 4 | 11.2100 | 0 | | | 3 | 3 | 2 | 0 | 3 | | | 0 | 3 | 3 | 2 | 3 |
| 5 | 11.2100 | 2 | | | 3 | 3 | 3 | 2 | 3 | | | 3 | 3 | 3 | 3 | 3 |
| 6 | 11.2100 | 2 | | | 3 | 3 | 3 | 3 | 2 | | | 3 | 3 | 3 | 3 | 2 |
| 7 | 11.2100 | 0 | | | 3 | 3 | 3 | 1 | 3 | | | 3 | 3 | 3 | 2 | 0 |
| 8 | 11.2100 | 3 | | | 2 | 3 | 3 | 2 | 3 | | | 3 | 3 | 3 | 3 | 0 |
| 9 | 11.2100 | 1 | | | 3 | 3 | 3 | 0 | 2 | | | 0 | 3 | 3 | 3 | 3 |
| 10 | 11.2100 | 2 | | | 3 | 3 | 3 | 3 | 3 | | | 3 | 3 | 3 | 3 | 0 |
| 11 | 11.2100 | 2 | | | 3 | 3 | 3 | 0 | 3 | | | 0 | 3 | 3 | 3 | 3 |
| 12 | 11.2100 | 3 | | | 3 | 3 | 3 | 3 | 3 | | | 3 | 3 | 3 | 3 | 3 |
| 13 | 11.2100 | 2 | | | 3 | 3 | 3 | 3 | 3 | | | 3 | 3 | 3 | 3 | 0 |
| 14 | 11.2100 | 3 | | | 3 | 3 | 3 | 3 | 3 | | | 3 | 3 | 3 | 3 | 0 |
| 15 | 11.2100 | 0 | | | 1 | 3 | 2 | 0 | 2 | | | 0 | 3 | 3 | 2 | 0 |
| 16 | 11.2100 | 3 | | | 3 | 3 | 3 | 1 | 3 | | | 0 | 3 | 3 | 3 | 3 |
| 17 | 11.2100 | 3 | | | 3 | 3 | 3 | 1 | 3 | | | 0 | 3 | 3 | 1 | 0 |
| 18 | 11.2100 | 2 | | | 3 | 3 | 3 | 1 | 3 | | | 0 | 3 | 3 | 3 | 0 |
| 19 | 11.2100 | 3 | | | 3 | 3 | 3 | 3 | 3 | | | 3 | 3 | 3 | 3 | 3 |
| 20 | 11.2100 | 1 | | | 3 | 3 | 3 | 1 | 3 | | | 0 | 3 | 3 | 3 | 3 |
| 21 | 11.2100 | 0 | | | 3 | 3 | 3 | 1 | 2 | | | 2 | 3 | 3 | 3 | 3 |

TABLE A-continued

| Ex. No. | Rate kg/ha | Yens | Anbg | Sejg | Dobr | Bygr | Mogl | Cobu | Vblu | Inmu | Wibw | Cath | Colq | Pesw | Rhqg | Rhjg |
|---|---|---|---|---|---|---|---|---|---|---|---|---|---|---|---|---|
| 22 | 11.2100 | 3 | | | 3 | 3 | 3 | 3 | 3 | | | 3 | 3 | 3 | 3 | 0 |
| 23 | 11.2100 | 1 | | | 3 | 3 | 2 | 0 | 2 | | | 3 | 3 | 2 | 3 | 0 |
| 24 | 11.2100 | 0 | | | 3 | 3 | 2 | 0 | 3 | | | 3 | 3 | 3 | 3 | 0 |
| 25 | 11.2100 | 1 | | | 3 | 3 | 3 | 1 | 3 | | | 3 | 3 | 3 | 3 | 0 |
| 26 | 11.2100 | 3 | | | 3 | 3 | 3 | 3 | 3 | | | 3 | 3 | 3 | 3 | 3 |
| 27 | 11.2100 | 1 | | | 3 | 3 | 1 | 0 | 2 | | | 2 | 3 | 3 | 3 | 3 |
| 28 | 11.2100 | 0 | | | 3 | 3 | 3 | 0 | 2 | | | 3 | 3 | 3 | 3 | 3 |
| 29 | 11.2100 | 2 | | | 3 | 3 | 3 | 0 | 2 | | | 0 | 3 | 3 | 3 | 3 |
| 30 | 11.2100 | 0 | | | 0 | 0 | 0 | 0 | 0 | | | 0 | 2 | 0 | 0 | 0 |
| 31 | 11.2100 | 0 | | | 0 | 1 | 0 | 0 | 0 | | | 0 | 0 | 1 | 0 | 0 |
| 32 | 11.2100 | 3 | | | 3 | 3 | 3 | 3 | 3 | | | 3 | 3 | 3 | 3 | 3 |
| 33 | 11.2100 | 0 | 3 | 3 | 3 | 3 | 2 | 1 | 3 | 3 | 3 | | | | | |
| 34 | 11.2100 | 0 | 3 | 3 | 3 | 3 | 3 | 0 | 3 | 3 | 3 | | | | | |
| 35 | 11.2100 | 3 | 3 | 3 | 3 | 3 | 3 | 3 | 3 | 3 | 3 | | | | | |
| 36* | 11.2100 | 0 | 3 | 3 | 2 | 3 | 3 | 0 | 3 | 3 | 3 | | | | | |
| 37 | 11.2100 | 1 | 3 | 3 | 3 | 3 | 3 | 2 | 3 | 3 | 3 | | | | | |
| 38 | 11.2100 | 3 | 3 | 3 | 3 | 3 | 3 | 3 | 3 | 3 | 3 | | | | | |
| 39 | 11.2100 | 0 | | | 3 | 3 | 2 | 0 | 2 | | | 1 | 3 | 3 | 3 | 1 |
| 40 | 11.2100 | 0 | 3 | 3 | 3 | 3 | 2 | 0 | 2 | 3 | 3 | | | | | |
| 41 | 11.2100 | 0 | 3 | 3 | 3 | 2 | 3 | 0 | 2 | 2 | 1 | | | | | |
| 42 | 11.2100 | 0 | 3 | 3 | 3 | 3 | 3 | 0 | 3 | 3 | 1 | | | | | |
| 43 | 11.2100 | 0 | 3 | 3 | 3 | 3 | 3 | 2 | 3 | 3 | 1 | | | | | |
| 44@ | 11.2100 | 1 | | | 3 | 3 | 3 | 1 | 3 | | | 2 | 3 | N | 3 | 0 |
| 45+ | 11.2100 | 0 | 3 | 3 | 0 | 3 | 0 | 0 | 0 | 1 | 0 | | | | | |
| 46+ | 11.2100 | 3 | 3 | 3 | 3 | 3 | 3 | 3 | 3 | 3 | 3 | | | | | |
| 47+ | 11.2100 | 3 | 3 | 3 | 3 | 3 | 3 | 0 | 3 | 3 | 3 | | | | | |
| 48+ | 11.2100 | 2 | 3 | 3 | 3 | 3 | 3 | 0 | 3 | 3 | 3 | | | | | |
| 49+ | 11.2100 | 3 | 3 | 3 | 3 | 3 | 3 | 3 | 3 | 3 | 3 | | | | | |
| 50 | 11.2100 | 3 | 3 | 3 | 3 | 3 | 3 | 3 | 3 | 3 | 3 | | | | | |
| 51 | 11.2100 | 0 | 3 | 3 | 3 | 3 | 3 | 0 | 3 | 3 | 1 | | | | | |
| 52 | 11.2100 | 3 | 3 | 3 | 3 | 3 | 3 | 3 | 3 | 3 | 3 | | | | | |
| 53 | 11.2100 | 3 | 3 | 3 | 3 | 3 | 3 | 2 | 3 | 3 | 3 | | | | | |
| 54 | 11.2100 | 1 | 3 | 3 | 3 | 3 | 2 | 0 | 3 | 3 | 3 | | | | | |
| 55 | 11.2100 | 1 | 3 | 3 | 3 | 3 | 3 | 0 | 3 | 3 | 3 | | | | | |
| 56 | 11.2100 | 0 | 3 | 2 | 3 | 3 | 3 | 0 | 3 | 3 | 3 | | | | | |
| 57 | 11.2100 | 2 | 3 | 3 | 3 | 3 | 3 | 0 | 3 | 3 | 3 | | | | | |
| 58 | 11.2100 | 0 | 3 | 3 | 3 | 3 | 3 | 0 | 3 | 3 | 2 | | | | | |
| 59 | 11.2100 | 3 | 3 | 3 | 3 | 3 | 3 | 1 | 3 | 3 | 3 | | | | | |
| 60 | 11.2100 | 0 | 3 | 3 | 3 | 3 | 3 | 0 | 3 | 3 | 2 | | | | | |

*DAMPING OFF-IM,WB. POOR GERMINATION-WB.
DAMPING OFF-IM,WB.
@POOR SW AND CA GERMINATION.
+POOR GERMINATION-CB,SJ.
+DAMPING OFF-IM,WB POOR GERMINATION-CB

PRE-EMERGENCE ACTIVITY ON WEEDS AND CROPS

In another set of tests, the pre-emergence activity of compounds of this invention was tested on weeds in the presence of crop plants. In these tests the following procedure was used:

Topsoil was sieved to pass through a ½ inch (1.27 cm) screen. Fertilizer was added to the topsoil in some of the tests, while in testing other compounds the fertilizer was omitted. The mixture was then sterilized by exposure to methyl bromide or by heating.

The topsoil mixture was placed in an aluminum pan and compacted to a depth of about 1.27 cm. from the top of the pan. A predetermined number of seeds of each of several monocotyledonous and dicotyledonous plant species and where noted vegetative propagules of various perennial plant species. The soil required to level fill a pan after seeding or adding vegetative propagules was weighed into another pan. A known amount of test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. Alternatively, the pans may be covered with the soil layer and the spray solution uniformly applied to the soil surface. When this latter method was used, the statement "surface application" accompanies the test data. In Table B below the amount of active ingredient applied is shown in the Table. After treatment, the pans were moved to a greenhouse bench. Moisture was supplied to each pan as needed for germination and growth. Growth of each species was observed and corrective measures (greenhouse fumigation, insecticide treatment, and the like) were applied as needed Approximately 10-14 days (usually 11 days) after planting and treating, the pans were observed and the results recorded. In some instances, a second observation is made (usually 24-28 days after seeding and treating, although this time interval was at the discretion of the observer), and these observations are indicated in the following tables by a "pound" sign (#) immediately following the Example number.

The pre-emergence data for weeds in the presence of crop plants is shown in the following Table B. In these tests, the plants are identified according to the following column headings printed diagonally above each column, the first column being the rate of application of the test compound in kg/ha:

| | | | | | | | | | | | | | | | | | | | |
|---|---|---|---|---|---|---|---|---|---|---|---|---|---|---|---|---|---|---|---|
| SOBE | Soybean | | VELE | Velvetleaf | | NOGL | Morningglory | | COTZ | Cotton | | | | | | | | | |
| SUBE | Sugarbeet | | DOBR | Downy Brome | | HESE | Hemp Sesbania | | RAPE | Oilseed Rape | | | | | | | | | |
| WHEZ | Wheat | | PRMI | Proso Millet | | COLQ | Common Lambsquarters | | JIWE | Jimsonweed | | | | | | | | | |
| RICE | Rice | | BYGR | Barnyardgrass | | PESW | Pennsylvania Smartweed | | | | | | | | | | | | |
| GRSO | Grain Sorghum | | LACG | Large Crabgrass | | | | | | | | | | | | | | | |
| COBU | Cocklebur | | GRFT | Green Foxtail | | | | | | | | | | | | | | | |
| WIBW | Wild Buckwheat | | CORN | Corn | | | | | | | | | | | | | | | |

As above, footnotes are shown at the end of the Table.

TABLE B

| Ex. No. | Rate kg/ha | Sobe | Cotz | Rapu | Cobe | Wibw | Mobgl | Hese | Jiwe | Vele | Whez | Rice | Grson | Corn | Dobr | Prmi | Bygr | Lacg | Grft | Subt | Colq | Pesw |
|---|---|---|---|---|---|---|---|---|---|---|---|---|---|---|---|---|---|---|---|---|---|---|
| 1* | 5.6050 | 3 | | 2 | 2 | 3 | 3 | | 3 | 3 | 3 | 3 | 2 | 3 | 3 | 3 | 3 | 3 | 3 | 3 | 3 | |
| * | 1.1210 | 2 | | 0 | 1 | 0 | 3 | | 3 | 3 | 3 | 3 | 2 | 3 | 3 | 3 | 3 | 3 | 3 | 3 | 3 | |
| * | 0.5605 | 1 | | 0 | 1 | 0 | 3 | | 2 | 1 | 2 | 3 | 0 | 3 | 3 | 3 | 3 | 3 | 3 | 3 | 3 | |
| * | 0.2803 | 0 | | 0 | 1 | 0 | 1 | | 0 | 0 | 1 | 2 | 1 | 1 | 3 | 3 | 3 | 3 | 1 | 2 | 3 | |
| * | 0.1401 | 0 | | 0 | 0 | 0 | 1 | | 0 | 0 | 2 | 1 | 0 | 0 | 2 | 3 | 2 | 3 | 1 | 3 | 3 | |
| * | 0.0701 | 0 | | 0 | 0 | 0 | 0 | | 0 | 0 | 0 | 0 | 0 | 0 | 0 | 0 | 1 | 3 | 0 | 0 | 0 | |
| * | 0.0350 | 0 | | 0 | 0 | 0 | 0 | | 0 | 0 | 0 | 0 | 0 | 0 | 0 | 0 | 1 | 0 | 0 | 0 | 0 | |
| * | 0.0175 | 0 | | 0 | 0 | 0 | 0 | | 0 | 0 | 0 | 0 | 0 | 0 | 0 | 0 | 0 | 0 | 0 | 0 | 0 | |
| * | 0.0087 | 0 | | 0 | 0 | 0 | 0 | | 0 | 0 | 0 | 0 | 0 | 0 | 0 | 0 | 0 | 0 | 0 | 0 | 0 | |
| 2 | 5.6050 | 3 | | 3 | 3 | 3 | 3 | | 3 | 3 | 3 | 3 | 3 | 3 | 3 | 3 | 3 | 3 | 3 | 3 | 3 | |
| | 5.6050 | 3 | | 3 | 3 | 3 | 3 | | 3 | 3 | 3 | 3 | 3 | — | 3 | 3 | 3 | 3 | 3 | 3 | 3 | |
| | 1.1210 | 3 | | 2 | 3 | 3 | 3 | | 3 | 3 | 3 | 3 | 3 | 3 | 3 | 3 | 3 | 3 | 3 | 3 | 3 | |
| | 1.1210 | 3 | | 2 | 3 | 3 | 3 | | 3 | 3 | 3 | 3 | 3 | — | 3 | 3 | 3 | 3 | 3 | 3 | 3 | |
| | 1.1210 | 3 | | 3 | 3 | 3 | 3 | | 3 | 3 | 3 | 3 | 3 | 3 | 3 | 3 | 3 | 3 | 3 | 3 | 3 | |
| | 0.5605 | 3 | | 3 | 3 | 3 | 3 | | 3 | 3 | 3 | 3 | 3 | 3 | 3 | 3 | 3 | 3 | 3 | 3 | 3 | |
| 2 | 0.5605 | 3 | | 1 | 3 | 3 | 3 | | 3 | 3 | 3 | 3 | 3 | — | 3 | 3 | 3 | 3 | 3 | 3 | 3 | |
| | 0.5605 | 3 | | 1 | 3 | 3 | 3 | | 3 | 3 | 3 | 3 | 3 | 3 | 3 | 3 | 3 | 3 | 3 | 3 | 3 | |
| | 0.2803 | 3 | | 0 | 3 | 3 | 3 | | 3 | 3 | 3 | 3 | 3 | 3 | 3 | 3 | 3 | 3 | 3 | 3 | 3 | |
| | 0.2803 | 3 | | 0 | 3 | 2 | 3 | | 3 | 3 | 3 | 3 | 3 | — | 3 | 3 | 3 | 3 | 3 | 3 | 3 | |
| | 0.2803 | 3 | | 3 | 3 | 3 | 3 | | 3 | 3 | 3 | 3 | 3 | 3 | 3 | 3 | 3 | 3 | 3 | 3 | 3 | |
| | 0.2803 | 3 | | 1 | 3 | 3 | 3 | | 3 | 3 | 3 | 3 | 3 | 3 | 3 | 3 | 3 | 3 | 3 | 3 | 3 | |
| | 0.2803 | 3 | | 3 | 3 | 3 | 3 | | 3 | 3 | 3 | 3 | 3 | 3 | 3 | 3 | 3 | 3 | 3 | 3 | 3 | |
| | 0.2803 | 3 | | 1 | 3 | 3 | 3 | | 3 | 3 | 3 | 3 | 3 | 3 | 3 | 3 | 3 | 3 | 3 | 3 | 3 | |
| | 0.2803 | 3 | | 2 | 3 | 3 | 3 | | 3 | 3 | 3 | 3 | 3 | 3 | 3 | 3 | 3 | 3 | 3 | 3 | 3 | |
| | 0.2803 | 3 | | 0 | 3 | 3 | 3 | | 3 | 3 | 3 | 3 | 3 | 3 | 3 | 3 | 3 | 3 | 3 | 3 | 3 | |
| | 0.2803 | 3 | | 2 | 2 | 3 | 3 | | 3 | 3 | 3 | 3 | 3 | 3 | 3 | 3 | 3 | 3 | 3 | 3 | 3 | |
| | 0.1401 | 2 | | 0 | 3 | 1 | 3 | | 3 | 3 | 3 | 3 | 2 | — | 3 | 3 | 3 | 3 | 3 | 3 | 3 | |
| | 0.1401 | 2 | | 0 | 3 | 3 | 3 | | 3 | 3 | 2 | 3 | 1 | 3 | 3 | 3 | 3 | 3 | 3 | 3 | 3 | |
| | 0.0701 | 2 | | 0 | 2 | 1 | 3 | | 3 | 3 | 3 | 3 | 2 | 3 | 3 | 3 | 3 | 3 | 3 | 3 | 3 | |
| | 0.0701 | 3 | | 0 | 3 | 0 | 3 | | 3 | 2 | 2 | 3 | 1 | — | 3 | 3 | 3 | 3 | 3 | 3 | 3 | |
| | 0.0701 | 3 | | 1 | 2 | 3 | 3 | | 3 | 1 | 3 | 3 | 1 | 3 | 3 | 3 | 3 | 3 | 3 | 3 | 3 | |
| 2 | 0.0701 | 3 | | 0 | 3 | 3 | 3 | | 3 | 2 | 3 | 3 | 2 | 3 | 3 | 3 | 3 | 3 | 2 | 3 | 3 | |
| | 0.0701 | 3 | | 0 | 3 | 3 | 3 | | 3 | 3 | 3 | 3 | 1 | 3 | 3 | 3 | 3 | 3 | 3 | 3 | 3 | |
| | 0.0701 | 3 | | 0 | 0 | 2 | 0 | | 1 | 3 | 0 | 3 | 0 | 3 | 3 | 3 | 3 | 3 | 2 | 3 | 3 | |
| | 0.0701 | 3 | | 1 | 3 | 3 | 1 | | 2 | 2 | 3 | 3 | 1 | 3 | 3 | 3 | 3 | 3 | 3 | 3 | 3 | |
| | 0.0701 | 3 | | 3 | 0 | 1 | 3 | | 3 | 2 | 3 | 3 | 2 | 3 | 3 | 3 | 3 | 3 | 2 | 2 | 3 | |
| | 0.0701 | 3 | | 0 | 3 | 3 | 3 | | 3 | 3 | 3 | 3 | 1 | 3 | 3 | 3 | 3 | 3 | 3 | 3 | 3 | |
| | 0.0350 | 3 | | 2 | 1 | 3 | 3 | | 3 | 0 | 3 | 1 | 0 | 3 | 3 | 3 | 3 | 3 | 3 | 3 | 3 | |
| | 0.0350 | 0 | | 0 | 1 | 0 | 2 | | 2 | 1 | 2 | 2 | 0 | 3 | 3 | 3 | 3 | 3 | 2 | 3 | 3 | |
| | 0.0350 | 1 | | 0 | 2 | 0 | 3 | | 3 | 2 | 3 | 3 | 0 | — | 3 | 3 | 3 | 3 | 2 | 3 | 3 | |
| | 0.0175 | 0 | | 0 | 2 | 0 | 3 | | 2 | 0 | 1 | 1 | 0 | — | 3 | 3 | 3 | 3 | 3 | 3 | 3 | |
| | 0.0175 | 0 | | 0 | 1 | 0 | 1 | | 1 | 1 | 1 | 0 | 2 | 3 | 3 | 3 | 3 | 3 | 1 | 1 | 3 | |
| | 0.0175 | 0 | | 1 | 1 | 3 | 3 | | 3 | 0 | 3 | 2 | 0 | 3 | 3 | 3 | 3 | 3 | 3 | 3 | 3 | |
| | 0.0175 | 1 | | 0 | 1 | 3 | 0 | | 0 | 2 | 3 | 3 | 0 | 3 | 3 | 3 | 3 | 3 | 1 | 0 | 2 | |
| | 0.0175 | 2 | | N | 1 | 2 | 2 | | 3 | 0 | 3 | 3 | 0 | 2 | 3 | 3 | 3 | 3 | 1 | 2 | 3 | |
| | 0.0175 | 0 | | 0 | 2 | 1 | 1 | | 1 | 2 | 3 | 1 | 0 | 1 | 3 | 3 | 3 | 3 | 1 | 3 | 3 | |
| 2 | 0.0175 | 1 | | 0 | 2 | 0 | 3 | | 3 | 1 | 3 | 0 | 0 | 3 | 3 | 3 | 3 | 3 | 2 | 2 | 3 | |
| | 0.0175 | 0 | | 0 | 0 | 0 | 0 | | 0 | 1 | 0 | 1 | 0 | 0 | 0 | 3 | 3 | 3 | 0 | 2 | 2 | |
| | 0.0175 | 2 | | 0 | 0 | 1 | 0 | | 3 | 1 | 3 | 3 | 0 | 1 | 3 | 3 | 3 | 3 | 0 | 0 | 3 | |
| | 0.0087 | 0 | | 0 | 0 | 0 | 1 | | 1 | 0 | 0 | 0 | 0 | 1 | 3 | 3 | 3 | 3 | 0 | 1 | 2 | |
| | 0.0087 | 0 | | 0 | 1 | 0 | 1 | | 2 | 0 | 0 | 2 | 0 | — | 3 | 3 | 3 | 3 | 1 | 3 | 3 | |
| | 0.0044 | 0 | | 0 | 0 | 0 | 0 | | 0 | 0 | 0 | 0 | 0 | 0 | 0 | 0 | 0 | 0 | 0 | 0 | 0 | |
| | 0.0044 | 0 | | 2 | 0 | 3 | 1 | | 0 | 0 | 2 | 0 | 0 | 1 | 3 | 3 | 3 | 3 | | 0 | 3 | |
| | 0.0044 | 0 | | 0 | 0 | 0 | 0 | | 0 | 0 | 0 | 0 | 0 | N | 0 | 0 | 1 | 2 | 0 | 0 | 3 | |
| | 0.0044 | 0 | | 0 | 0 | 0 | 0 | | 0 | 1 | 0 | 2 | 0 | 0 | 1 | 2 | 1 | 3 | 0 | 0 | 1 | |
| | 0.0044 | 0 | | 0 | 0 | 0 | 3 | | 0 | 0 | 3 | 0 | 0 | 3 | 0 | 3 | 1 | 3 | 2 | 3 | 3 | |
| | 0.0044 | 0 | | 0 | N | 0 | 1 | | 0 | 0 | 1 | 0 | 0 | 1 | 2 | 2 | 3 | 3 | 0 | 2 | 1 | |
| | 0.0044 | 0 | | 0 | 0 | 0 | 0 | | 0 | 0 | 1 | 0 | 0 | 0 | 3 | 3 | 3 | 3 | 1 | 1 | 2 | |
| | 0.0044 | 0 | | N | 1 | 0 | 0 | | 0 | 0 | 3 | 0 | 0 | 0 | 2 | 1 | 3 | 3 | 0 | 3 | 3 | |
| | 0.0021 | 0 | | 0 | 0 | 0 | 0 | | 0 | 0 | 0 | 0 | 0 | 0 | 0 | 0 | 0 | 0 | 0 | 0 | 0 | |
| 3 | 5.6050 | 2 | | 0 | 2 | 3 | 3 | | 3 | 3 | 3 | 3 | 3 | 2 | 3 | 3 | 3 | 3 | 3 | 3 | 3 | |
| | 1.1210 | 2 | | 0 | 1 | 1 | 3 | | 3 | 3 | 3 | 2 | 2 | 3 | 3 | 3 | 3 | 3 | 2 | 3 | 3 | |
| | 0.5605 | 0 | | 0 | 1 | 1 | 2 | | 2 | 1 | 2 | 3 | 1 | 0 | 3 | 3 | 3 | 3 | 1 | 3 | 2 | |
| | 0.2803 | 0 | | 0 | 0 | 0 | 1 | | 1 | 1 | 1 | 2 | 0 | 2 | 2 | 3 | 3 | 0 | 3 | 2 | | |
| | 0.1401 | 0 | | 0 | 0 | 0 | 1 | | 0 | 0 | 2 | 0 | 0 | 2 | 1 | 2 | 3 | 0 | 1 | 1 | | |
| | 0.0701 | 0 | | 0 | 0 | 0 | 0 | | 0 | 0 | 0 | 0 | 0 | 0 | 2 | 2 | 0 | 0 | 0 | 0 | | |
| | 0.0350 | 0 | | 0 | 0 | 0 | 0 | | 0 | 0 | 0 | 0 | 0 | 0 | 0 | 0 | 0 | 0 | 0 | 0 | | |

TABLE B-continued

| Ex. No. | Rate kg/ha | Soybe | Cotze | Rape | Cobuw | Wibl | Moge | Hese | Jiwee | Velee | Wheze | Rice | Grson | Cornr | Dobri | Prmi | Bygrg | Lacft | Grfbte | Suqb | Peqsw |
|---|---|---|---|---|---|---|---|---|---|---|---|---|---|---|---|---|---|---|---|---|---|
|  | 0.0175 | 0 |  |  | 0 | 0 | 0 | 0 | 0 | 0 | 0 | 0 | 0 | 0 | 0 | 0 | 0 | 0 | 0 | 0 | 0 |
|  | 0.0087 | 0 |  |  | 0 | 0 | 0 | 0 | 0 | 0 | 0 | 0 | 0 | 0 | 0 | 0 | 0 | 0 | 0 | 0 | 0 |
| 4 | 5.6050 | 0 |  |  | 0 | 3 | 2 | 3 | 3 | 2 | 2 | 2 | 2 | 2 | 3 | 3 | 3 | 3 | 2 | 3 | 3 |
|  | 1.1210 | 0 |  |  | 0 | 1 | 0 | 0 | 2 | 1 | 1 | 1 | 0 | 3 | 3 | 3 | 3 | 3 | 1 | 3 | 3 |
|  | 0.5605 | 0 |  |  | 0 | 1 | 0 | 0 | 0 | 0 | 0 | 1 | 0 | 2 | N | 3 | 3 | 2 | 0 | 2 | 3 |
|  | 0.2803 | 0 |  |  | 0 | 1 | 0 | 0 | 0 | 0 | 0 | 0 | 0 | 1 | 0 | 2 | 2 | 2 | 0 | 0 | 3 |
|  | 0.1401 | 0 |  |  | 0 | 1 | 0 | 0 | 0 | 0 | 0 | 0 | 0 | 1 | 0 | 0 | 0 | 0 | 0 | 0 | 1 |
|  | 0.0701 | 0 |  |  | 0 | 0 | 0 | 0 | 0 | 0 | 0 | 0 | 0 | 0 | 0 | 0 | 0 | 0 | 0 | 0 | 3 |
|  | 0.0350 | 0 |  |  | 0 | 0 | 0 | 0 | 0 | 0 | 0 | 0 | 0 | 0 | 0 | 0 | 0 | 0 | 0 | 0 | 3 |
| 5 | 5.6050 | 2 |  |  | 1 | 3 | 3 | 3 | 3 | 3 | 3 | 3 | 3 | 3 | 3 | 3 | 3 | 3 | 3 | 3 | 3 |
|  | 1.1210 | 1 |  |  | 0 | 3 | 3 | 3 | 3 | 2 | 2 | 3 | 1 | 3 | 3 | 3 | 3 | 3 | 2 | 3 | 3 |
|  | 0.5605 | 1 |  |  | 0 | 2 | 3 | 3 | 3 | 2 | 2 | 3 | 1 | 3 | 3 | 3 | 3 | 3 | 2 | 3 | 3 |
|  | 0.2803 | 1 |  |  | 0 | 3 | 0 | 3 | 3 | 2 | 2 | 2 | 0 | 3 | 3 | 3 | 3 | 3 | 2 | 3 | 3 |
|  | 0.1401 | 0 |  |  | 0 | 0 | 0 | 0 | 2 | 1 | 1 | 2 | 0 | 2 | N | 3 | 3 | 3 | 0 | 2 | 3 |
|  | 0.0701 | 0 |  |  | 0 | 0 | 0 | 0 | 1 | 0 | 1 | 1 | 0 | 1 | N | 3 | 3 | 3 | 0 | 1 | 2 |
|  | 0.0350 | 0 |  |  | 0 | 1 | 0 | 0 | N | 0 | 0 | 1 | 0 | 0 | 1 | 1 | 3 | 3 | 0 | N | 2 |
|  | 0.0175 | 0 |  |  | 0 | 0 | 0 | 0 | 0 | 0 | 0 | 0 | 0 | 0 | 0 | 0 | 2 | 1 | 0 | 0 | N |
|  | 0.0087 | 0 |  |  | 0 | 0 | 0 | 0 | 0 | 0 | 0 | 0 | 0 | 0 | 0 | 0 | 0 | 0 | 0 | 0 | 2 |
| 6 | 5.6050 | 3 |  |  | 1 | 3 | 3 | 3 | 3 | 3 | 3 | 3 | 3 | 3 | 3 | 3 | 3 | 3 | 3 | 3 | 3 |
|  | 1.1210 | 2 |  |  | 1 | 3 | 3 | 3 | 3 | 3 | 3 | 3 | 3 | 3 | 3 | 3 | 3 | 3 | 3 | 3 | 3 |
|  | 0.5605 | 1 |  |  | 0 | 3 | 3 | 3 | 3 | 3 | 2 | 3 | 1 | 3 | 3 | 3 | 3 | 3 | 3 | 3 | 3 |
|  | 0.2803 | 1 |  |  | 0 | 2 | 1 | 3 | 3 | 1 | 1 | 3 | 1 | 2 | 3 | 3 | 3 | 3 | 2 | 3 | 3 |
|  | 0.1401 | 0 |  |  | 0 | 2 | 1 | 1 | 3 | 1 | 1 | 1 | 0 | 0 | N | 3 | 3 | 3 | 1 | N | 3 |
|  | 0.0701 | 0 |  |  | 0 | 2 | 0 | 1 | 1 | 0 | 1 | 1 | 0 | 1 | 3 | 3 | 3 | 3 | N | N | 3 |
| 6 | 0.0350 | 0 |  |  | 0 | 1 | 0 | 0 | 1 | 0 | 0 | 1 | 0 | 0 | N | 2 | 3 | 3 | 0 | 0 | 2 |
|  | 0.0175 | 0 |  |  | 0 | 0 | 0 | 0 | 0 | 0 | 0 | 0 | 0 | 0 | N | 0 | 0 | 0 | 0 | 0 | N |
|  | 0.0087 | 0 |  |  | 0 | 0 | 0 | 0 | 0 | 0 | 0 | 0 | 0 | N | 2 | 0 | 0 | 0 | 0 | 0 | 0 |
| 7 | 5.6050 | 2 |  |  | 1 | 3 | 3 | 3 | 3 | 3 | 3 | 3 | 3 | 3 | 3 | 3 | 3 | 3 | 3 | 3 | 3 |
|  | 1.1210 | 2 |  |  | 0 | 3 | 2 | 3 | 3 | 2 | 1 | 2 | 2 | 3 | 3 | 3 | 3 | 3 | 3 | 3 | 3 |
|  | 0.5605 | 0 |  |  | 0 | 1 | 0 | 1 | 2 | 1 | 1 | 2 | 2 | 1 | 3 | 3 | 3 | 3 | 2 | 2 | 3 |
|  | 0.2803 | 0 |  |  | 0 | 0 | 0 | 0 | 1 | 0 | 0 | 1 | 0 | 3 | 3 | 3 | 3 | 3 | 0 | 1 | 3 |
|  | 0.1401 | 0 |  |  | 0 | N | 0 | 0 | 0 | 0 | 0 | 1 | 0 | 0 | 1 | 3 | 3 | 3 | 0 | N | 0 |
|  | 0.0701 | 0 |  |  | 0 | 0 | 0 | 0 | 0 | 0 | 0 | 0 | 0 | 0 | N | 0 | 1 | 2 | 0 | N | 3 |
|  | 0.0350 | 0 |  |  | 0 | 0 | 0 | 0 | 0 | 0 | 0 | 0 | 0 | 0 | N | 0 | 0 | 1 | 0 | 0 | N |
|  | 0.0175 | 0 |  |  | 0 | 0 | 0 | 0 | 0 | 0 | 0 | 0 | 0 | 0 | N | 0 | 0 | 0 | 0 | 0 | 3 |
| 8 | 5.6050 | 2 |  |  | 1 | 3 | 3 | 3 | 3 | 3 | 3 | 3 | 3 | 3 | 3 | 3 | 3 | 3 | 3 | 3 | 3 |
|  | 1.1210 | 2 |  |  | 0 | 3 | 2 | 3 | 3 | 2 | 3 | 3 | 1 | 3 | 3 | 3 | 3 | 3 | 3 | 3 | 3 |
|  | 0.5605 | 1 |  |  | 0 | 3 | 1 | 3 | 3 | 2 | 2 | 2 | 1 | 3 | 3 | 3 | 3 | 3 | 2 | 3 | 3 |
|  | 0.2803 | 0 |  |  | 0 | 3 | 0 | 3 | 2 | 1 | 2 | 2 | 0 | 3 | 3 | 3 | 3 | 3 | 1 | 3 | 3 |
| 8 | 0.1401 | 0 |  |  | 0 | 1 | 0 | 1 | 2 | 0 | 2 | 2 | 0 | 3 | 3 | 3 | 3 | 3 | 1 | 3 | 3 |
|  | 0.0701 | 0 |  |  | 0 | 0 | 0 | 0 | 0 | 0 | 1 | 0 | 0 | 2 | 2 | 1 | 3 | 3 | 0 | 1 | 2 |
|  | 0.0350 | 0 |  |  | 0 | 0 | 0 | 0 | 0 | 0 | 1 | 0 | 0 | 2 | 1 | 1 | 3 | 3 | 0 | 0 | 1 |
|  | 0.0175 | 0 |  |  | 0 | 0 | 0 | 0 | 0 | 0 | 1 | 0 | 0 | 1 | 1 | 2 | 3 | 3 | 0 | 0 | 1 |
| 9 | 5.6050 | 0 |  |  | 0 | 0 | 0 | 1 | 2 | 1 | 2 | 3 | 0 | 2 | 3 | 3 | 3 | 3 | 0 | 2 | 2 |
|  | 1.1210 | 0 |  |  | 0 | 0 | 0 | 0 | 0 | 0 | 0 | 0 | 1 | 0 | 0 | 0 | 1 | 0 | 0 | 0 |
|  | 0.5605 | 0 |  |  | 0 | 0 | 0 | 0 | 0 | 0 | 0 | 0 | 0 | 0 | 0 | 0 | 0 | 0 | 0 | 0 | 0 |
|  | 0.2803 | 0 |  |  | 0 | 0 | 0 | 0 | 0 | 0 | 0 | 0 | 0 | 0 | 0 | 0 | 0 | 0 | 0 | 0 | 0 |
|  | 0.1401 | 0 |  |  | 0 | 0 | 0 | 0 | 0 | 0 | 0 | 0 | 0 | 0 | 0 | 0 | 0 | 0 | 0 | 0 | 0 |
|  | 0.0701 | 0 |  |  | 0 | 0 | 0 | 0 | 0 | 0 | 0 | 0 | 0 | 0 | 0 | 0 | 0 | 0 | 0 | 0 | 0 |
|  | 0.0350 | 0 |  |  | 0 | 0 | 0 | 0 | 0 | 0 | 0 | 0 | 0 | 0 | 0 | 0 | 0 | 0 | 0 | 0 | 0 |
|  | 0.0175 | 0 |  |  | 0 | 0 | 0 | 0 | 0 | 0 | 0 | 0 | 0 | 0 | 0 | 0 | 0 | 0 | 0 | 0 | 0 |
| 10 | 5.6050 | 3 |  |  | 1 | 3 | 3 | 3 | 3 | 3 | 3 | 3 | 3 | 3 | 3 | 3 | 3 | 3 | 3 | 3 | 3 |
|  | 1.1210 | 2 |  |  | 1 | 3 | 3 | 3 | 3 | 2 | 3 | 3 | 3 | 3 | 3 | 3 | 3 | 3 | 3 | 3 | 3 |
|  | 0.5605 | 2 |  |  | 0 | 3 | 2 | 3 | 3 | 3 | 3 | 3 | 2 | 3 | 3 | 3 | 3 | 3 | 3 | 3 | 3 |
| 10 | 0.2803 | 1 |  |  | 0 | 3 | 1 | 3 | 3 | 2 | 3 | 3 | 3 | 3 | 3 | 3 | 3 | 3 | 1 | 3 | 3 |
|  | 0.1401 | 0 |  |  | 0 | 1 | 0 | 3 | 3 | 1 | 2 | 3 | 0 | 3 | 3 | 3 | 3 | 3 | 1 | 3 | 3 |
|  | 0.0701 | 0 |  |  | 0 | 0 | 0 | 2 | 2 | 1 | 2 | 3 | 0 | 3 | 3 | 3 | 3 | 3 | 0 | 2 | 3 |
|  | 0.0350 | 0 |  |  | 0 | 0 | 0 | 1 | 2 | 0 | 1 | 2 | 0 | 2 | 3 | 3 | 3 | 3 | 0 | 2 | 3 |
|  | 0.0175 | 0 |  |  | 0 | 0 | 0 | 0 | 0 | 0 | 0 | 0 | 0 | 2 | 2 | 2 | 3 | 3 | 0 | N | 3 |
| 11 | 5.6050 | 1 |  |  | 0 | 3 | 3 | 3 | 3 | 3 | 3 | 3 | 2 | 3 | 3 | 3 | 3 | 3 | 3 | 3 | 3 |
|  | 1.1210 | 0 |  |  | 0 | 1 | 0 | 1 | 3 | 1 | 3 | 2 | 1 | 3 | 3 | 3 | 3 | 3 | 1 | 3 | 3 |
|  | 0.5605 | 0 |  |  | 0 | 2 | 0 | 0 | 2 | 0 | 1 | 2 | 0 | 2 | 3 | 3 | 3 | 3 | N | 3 | 2 |
|  | 0.2803 | 0 |  |  | 0 | 0 | 0 | 0 | 1 | 0 | 1 | 1 | 0 | 1 | 3 | 3 | 3 | 3 | N | N | 1 |
|  | 0.1401 | 0 |  |  | 0 | 0 | 0 | 0 | 0 | 0 | 0 | 0 | 0 | 1 | 0 | 2 | 3 | 1 | 0 | 0 | 0 |
|  | 0.0701 | 0 |  |  | 0 | 0 | 0 | 0 | 0 | 0 | 0 | 0 | 0 | 0 | 0 | 0 | 1 | 0 | 0 | 0 | 0 |
|  | 0.0350 | 0 |  |  | 0 | 0 | 0 | 0 | 0 | 0 | 0 | 0 | 0 | 0 | 0 | 0 | 0 | 0 | 0 | 0 | 0 |
|  | 0.0175 | 0 |  |  | 0 | 0 | 0 | 0 | 0 | 0 | 0 | 0 | 0 | 0 | 0 | 0 | 0 | 0 | 0 | 0 | 0 |
| 12 | 5.6050 | 3 |  |  | 3 | 3 | 3 | 3 | 3 | 3 | 3 | 3 | 3 | 3 | 3 | 3 | 3 | 3 | 3 | 3 | 3 |
|  | 1.1210 | 2 |  |  | 0 | 3 | 1 | 3 | 3 | 3 | 3 | 3 | 2 | 3 | 3 | 3 | 3 | 3 | 3 | 3 | 3 |
| 12 | 0.5605 | 0 |  |  | 0 | 3 | 0 | 3 | 3 | 3 | 3 | 3 | 2 | 3 | 3 | 3 | 3 | 3 | 3 | 3 | 3 |
|  | 0.2803 | 0 |  |  | 0 | 3 | 2 | 3 | 3 | 2 | 3 | 3 | 2 | 3 | 3 | 3 | 3 | 3 | 1 | 3 | 3 |
|  | 0.1401 | 0 |  |  | 0 | 3 | 0 | 2 | 2 | 1 | 2 | 3 | 1 | 3 | 3 | 3 | 3 | 3 | 1 | 2 | 3 |
|  | 0.0701 | 0 |  |  | 0 | 2 | 0 | 1 | 1 | 0 | 2 | 3 | 0 | 3 | 3 | 3 | 3 | 3 | 0 | 1 | 3 |
|  | 0.0350 | 0 |  |  | 0 | 0 | 0 | 1 | 1 | 0 | 1 | 3 | 0 | 2 | 3 | 3 | 3 | 3 | 0 | 1 | 3 |
|  | 0.0175 | 0 |  |  | 0 | 0 | 0 | 0 | 0 | 0 | 3 | 3 | 0 | 2 | 1 | 1 | 2 | 2 | 0 | 0 | 1 |
|  | 0.0087 | 0 |  |  | 0 | 0 | 0 | 0 | 0 | 0 | 0 | N | 0 | 0 | 0 | 0 | 0 | 1 | 0 | 0 | 0 |
|  | 0.0044 | 0 |  |  | 0 | 0 | 0 | 0 | 0 | 0 | 0 | N | 0 | 0 | 0 | 0 | 0 | 1 | 0 | 0 | 0 |
| 13 | 5.6050 | 3 |  |  | 2 | 3 | 3 | 3 | 3 | 3 | 3 | 3 | 3 | 3 | 3 | 3 | 3 | 3 | 3 | 3 | 3 |

TABLE B-continued

| Ex. No. | Rate kg/ha | Soybe e | Cot t z | Rape p e | Cobu w | Wibg l | Mo g l | Hose e | Jiwe e | Vele e | Whez e | Rico n | Gror r | Cobmi r | Dry m i | Prymgr | Bary c g | Lart g | Grsfuteq | Sub e q | Pesw |
|---|---|---|---|---|---|---|---|---|---|---|---|---|---|---|---|---|---|---|---|---|
|  | 1.1210 | 3 |  | 2 | 3 | 3 | 3 | 3 | 3 | 3 | 3 | 3 | 3 | 3 | 3 | 3 | 3 | 3 | 3 | 3 | 3 |
|  | 0.5605 | 2 |  | 0 | 3 | 1 | 3 | 3 | 3 | 3 | 3 | 2 | 3 | 3 | 3 | 3 | 3 | 3 | 3 | 3 | 3 |
|  | 0.2803 | 2 |  | 0 | 2 | 2 | 3 | 3 | 1 | 3 | 3 | 2 | 3 | 3 | 3 | 3 | 3 | 3 | 3 | 3 | 3 |
|  | 0.1401 | 0 |  | 0 | 3 | 1 | 3 | 3 | 1 | 3 | 3 | 1 | 3 | 3 | 3 | 3 | 3 | 3 | 3 | 3 | 3 |
|  | 0.0701 | 1 |  | 0 | 2 | 1 | 3 | 3 | 2 | 3 | 3 | 0 | 1 | 3 | 3 | 3 | 3 | 3 | 3 | 3 | 3 |
|  | 0.0350 | 0 |  | 0 | 1 | 0 | 0 | 2 | 0 | 3 | 3 | 0 | 1 | 3 | 2 | 3 | 3 | 3 | 2 | 3 | 3 |
| 13 | 0.0175 | 0 |  | 0 | 1 | 0 | 0 | 2 | 0 | 2 | 2 | 0 | 0 | 3 | 2 | 3 | 3 | 1 | 3 | 3 | 3 |
|  | 0.0087 | 0 |  | 0 | 0 | 0 | 0 | 0 | 0 | 1 | 0 | 0 | 0 | 1 | 1 | 1 | 3 | 0 | 1 | 1 | 1 |
| 14 | 5.6050 | 3 |  | 2 | 3 | 3 | 3 | 3 | 3 | 3 | 3 | 3 | 3 | 3 | 3 | 3 | 3 | 3 | 3 | 3 | 3 |
|  | 1.1210 | 3 |  | 1 | 3 | 3 | 3 | 3 | 3 | 3 | 3 | 3 | 3 | 3 | 3 | 3 | 3 | 3 | 3 | 3 | 3 |
|  | 0.5605 | 2 |  | 0 | 3 | 2 | 3 | 3 | 2 | 2 | 3 | 2 | 3 | 3 | 3 | 3 | 3 | 3 | 3 | 3 | 3 |
|  | 0.2803 | 1 |  | 0 | 3 | 0 | 3 | 3 | 3 | 3 | 3 | 2 | 3 | 3 | 3 | 3 | 3 | 3 | 3 | 3 | 3 |
|  | 0.1401 | 0 |  | 0 | 3 | 1 | 3 | 3 | 2 | 2 | 3 | 2 | 3 | 3 | 3 | 3 | 3 | 3 | 2 | 3 | 3 |
|  | 0.0701 | 0 |  | 0 | 1 | 1 | 2 | 1 | 0 | 1 | 3 | 0 | 3 | 3 | 3 | 3 | 3 | 3 | 1 | 3 | 3 |
|  | 0.0350 | 0 |  | 0 | 0 | 0 | 2 | 2 | 0 | 2 | 3 | 0 | 3 | 3 | 3 | 3 | 3 | 3 | 1 | 2 | 3 |
|  | 0.0175 | 0 |  | 0 | 1 | 0 | 0 | 0 | 0 | 0 | 3 | 0 | 2 | 3 | 2 | 3 | 3 | 0 | 2 | 2 | 2 |
|  | 0.0087 | 0 |  | 0 | 0 | 0 | 0 | 0 | 0 | 0 | N | 0 | 0 | 1 | 0 | 1 | 3 | 0 | 0 | 0 | 0 |
| 15 | 5.6050 | 2 |  | 0 | 2 | 2 | 3 | 3 | 1 | 3 | 3 | 2 | 2 | 3 | 3 | 3 | 3 | 3 | 3 | 3 | 3 |
|  | 1.1210 | 0 |  | 0 | 2 | 0 | 1 | 3 | 0 | 2 | 2 | 0 | 0 | 3 | 2 | 1 | 3 | N | N | N | 2 |
|  | 0.5605 | 0 |  | 0 | 2 | 0 | 0 | 1 | 0 | 0 | 2 | 0 | 0 | 1 | 0 | 0 | 3 | N | N | N | 1 |
|  | 0.2803 | 0 |  | 0 | 0 | 0 | 0 | 0 | 0 | 0 | 0 | 0 | 0 | 0 | 0 | 0 | 3 | 0 | 2 | 0 |
| 15 | 0.1401 | 0 |  | 0 | 0 | 0 | 0 | 0 | 0 | 0 | 0 | 0 | 0 | 0 | 0 | 0 | 0 | 0 | 0 | 0 | 0 |
|  | 0.0701 | N |  | 0 | 0 | 0 | 0 | 0 | 0 | 0 | 0 | 0 | N | 1 | 0 | 0 | 0 | 0 | 0 | 0 | 0 |
|  | 0.0350 | 0 |  | 0 | N | 0 | 0 | 0 | 0 | 0 | 0 | 0 | 0 | 0 | 0 | 0 | 0 | 0 | 0 | N | 0 |
| 16 | 5.6050 | 3 |  | 1 | 3 | 3 | 3 | 3 | 3 | 3 | 3 | 3 | 3 | 3 | 3 | 3 | 3 | 3 | 3 | 3 | 3 |
|  | 1.1210 | 0 |  | 0 | 3 | 1 | 3 | 3 | 2 | 2 | 3 | 2 | 3 | 3 | 3 | 3 | 3 | 3 | 3 | 3 | 3 |
|  | 0.5605 | 0 |  | 0 | N | 1 | 3 | 2 | 3 | 2 | 2 | 0 | 3 | 3 | 3 | 3 | 3 | N | 3 | 3 | 3 |
|  | 0.2803 | 1 |  | 0 | 0 | 1 | 2 | 2 | 1 | 2 | 3 | 0 | 2 | 3 | 3 | 3 | 3 | 1 | 1 | 1 | 3 |
|  | 0.1401 | 0 |  | 0 | 0 | 0 | 1 | 0 | 0 | 2 | 1 | 0 | 2 | 2 | 2 | 2 | 3 | 0 | 0 | 0 | 2 |
|  | 0.0701 | 0 |  | 0 | 0 | 0 | 0 | 0 | 0 | 2 | 1 | 0 | 2 | 1 | 1 | 0 | 1 | 0 | 0 | 0 | 1 |
|  | 0.0350 | 0 |  | 0 | 0 | 0 | 0 | 0 | 0 | 0 | 0 | 0 | 0 | 0 | 0 | 0 | 0 | 0 | 0 | 0 | 0 |
|  | 0.0175 | 0 |  | 0 | 0 | 0 | 0 | 0 | 0 | 0 | 0 | 0 | 0 | 0 | 0 | 0 | 0 | 0 | 0 | 0 | 1 |
|  | 0.0087 | 0 |  | 0 | 0 | 0 | 0 | 0 | 0 | 0 | 0 | 0 | 0 | 0 | 0 | 0 | 0 | 0 | 0 | 0 | 2 |
| 17 | 5.6050 | 3 |  | 1 | 3 | 3 | 3 | 3 | 3 | 3 | 3 | 3 | 3 | 3 | 3 | 3 | 3 | 3 | 3 | 3 | 3 |
|  | 1.1210 | 2 |  | 0 | 3 | 3 | 3 | 3 | 1 | 3 | 3 | 1 | 3 | 3 | 3 | 3 | 3 | 3 | 3 | 3 | 3 |
|  | 0.5605 | N |  | N | 3 | 1 | 2 | 2 | 0 | 3 | 2 | 1 | 2 | 3 | 3 | 3 | 3 | 1 | 2 | 3 |
| 17 | 0.2803 | 0 |  | 1 | 0 | 0 | 0 | 1 | 0 | 3 | 1 | 0 | 2 | 3 | 3 | 3 | 3 | 0 | 0 | 3 |
|  | 0.1401 | 0 |  | 0 | 1 | 0 | 2 | 2 | 0 | 0 | 1 | 0 | 1 | 3 | 3 | 3 | 3 | 0 | N | 3 |
|  | 0.0701 | 0 |  | 0 | 0 | 0 | 0 | 0 | 0 | 0 | 0 | 0 | 0 | 0 | 0 | 0 | 0 | N | N | 1 |
|  | 0.0350 | 0 |  | 0 | 0 | 0 | 0 | 0 | 0 | 0 | 0 | 0 | 0 | 2 | 2 | 1 | 0 | 0 | 1 |
| 18 | 5.6050 | 3 |  | 0 | 3 | 3 | 3 | 3 | 3 | 3 | 3 | 3 | 2 | 3 | 3 | 3 | 3 | 3 | N | 3 |
|  | 1.1210 | 1 |  | 0 | 2 | 3 | 3 | 3 | 2 | 3 | 3 | 3 | 3 | 3 | 3 | 3 | 3 | 2 | 3 | 3 |
|  | 0.5605 | 1 |  | 0 | 3 | 1 | 3 | 3 | 3 | 2 | 2 | 1 | 3 | 3 | 3 | 3 | 3 | 3 | 3 | 3 |
|  | 0.2803 | 0 |  | 0 | 1 | 2 | 2 | 2 | 1 | 1 | 2 | 0 | 3 | 3 | 3 | 3 | 3 | 2 | 3 | 3 |
|  | 0.1401 | 0 |  | 0 | 0 | 0 | 0 | 0 | 1 | 3 | 1 | 0 | 3 | 3 | 3 | 3 | 3 | 0 | 2 | 3 |
|  | 0.0701 | 0 |  | 0 | 0 | 0 | 0 | 2 | 0 | 0 | 1 | 0 | 0 | 1 | 3 | 1 | 3 | 0 | 1 | 3 |
|  | 0.0350 | 0 |  | 0 | 0 | 0 | 1 | 0 | 1 | 3 | 1 | 0 | 2 | 3 | 3 | 2 | 1 | 0 | 0 | 2 |
| 19 | 5.6050 | 3 |  | 3 | 3 | 3 | 3 | 3 | 3 | 3 | 3 | 3 | 3 | 3 | 3 | 3 | 3 | 3 | 3 | 3 |
|  | 1.1210 | 3 |  | 2 | 3 | 3 | 3 | 3 | 3 | 3 | 3 | 3 | 3 | 3 | 3 | 3 | 3 | 3 | 3 | 3 |
|  | 0.5605 | 3 |  | 1 | 3 | 3 | 3 | 3 | 3 | 3 | 3 | 3 | 3 | 3 | 3 | 3 | 3 | 3 | 3 | 3 |
|  | 0.2803 | 2 |  | 0 | 3 | 3 | 3 | 3 | 3 | 3 | 3 | 3 | 3 | 3 | 3 | 3 | 3 | 3 | 3 | 3 |
| 19 | 0.1401 | 1 |  | 0 | 3 | 0 | 1 | 1 | 2 | 3 | 3 | 1 | 3 | 3 | 3 | 3 | 3 | 3 | 3 | 3 |
|  | 0.0701 | 1 |  | 0 | 3 | 0 | 3 | 3 | 2 | 2 | 3 | 0 | 2 | 3 | 3 | 3 | 3 | 2 | 3 | 3 |
|  | 0.0350 | 0 |  | 0 | 2 | 0 | 2 | 2 | 0 | 2 | 3 | 0 | 2 | 3 | 3 | 3 | 3 | 1 | 3 | 3 |
|  | 0.0175 | 0 |  | 0 | 0 | 0 | 1 | 1 | 0 | 2 | 2 | 0 | 1 | 3 | 3 | 3 | 3 | 0 | 1 | 3 |
|  | 0.0087 | 0 |  | 0 | 0 | 0 | 0 | 0 | 0 | 0 | 1 | 0 | 2 | 3 | 2 | 3 | 3 | 0 | 0 | 1 |
|  | 0.0044 | 0 |  | 0 | 0 | 0 | 0 | 0 | 0 | 0 | 0 | 0 | 0 | 1 | 3 | 3 | 0 | 0 | 0 | 0 |
| 20 | 5.6050 | 3 |  | 1 | 3 | 0 | 3 | 3 | 3 | 3 | 3 | 2 | 3 | 3 | 3 | 3 | 3 | 2 | 3 | 3 |
|  | 1.1210 | 0 |  | 0 | 3 | 0 | 2 | 2 | 1 | 2 | 3 | 1 | 2 | 3 | 3 | 3 | 3 | 0 | 2 | 2 |
|  | 0.5605 | 0 |  | 0 | 1 | 0 | 0 | 1 | 0 | 3 | 3 | 0 | 3 | 3 | 3 | 3 | 3 | 0 | 0 | 2 |
|  | 0.2803 | N |  | 0 | 0 | 0 | 0 | 0 | 0 | 1 | 1 | 0 | 0 | 0 | 3 | 3 | 3 | 0 | 0 | 0 |
|  | 0.1401 | 0 |  | 0 | 0 | 0 | 0 | 0 | 0 | 1 | 0 | 0 | 1 | 0 | 2 | 2 | 3 | 0 | 0 | 0 |
|  | 0.0701 | 0 |  | 0 | 0 | 0 | 0 | 0 | 0 | 1 | 0 | 0 | 0 | 0 | 2 | 3 | 0 | 0 | 0 |
|  | 0.0350 | 0 |  | 0 | 0 | 0 | 0 | 0 | 0 | 0 | 0 | 0 | 0 | 0 | 0 | 0 | N | 2 | 0 | 0 | 0 |
|  | 0.0175 | 0 |  | 0 | 0 | 0 | 0 | 0 | 0 | 0 | 0 | 0 | 0 | 0 | 0 | 0 | 0 | 0 | 0 | 0 | 0 |
| 21 | 5.6050 | 1 |  | 0 | 2 | 1 | 3 | 3 | 0 | 3 | 3 | 0 | 2 | 3 | 3 | 3 | 3 | 2 | 2 | 3 | 3 |
|  | 1.1210 | 0 |  | 0 | 2 | 1 | 1 | 2 | 0 | 1 | 1 | 0 | 3 | 2 | 3 | 3 | 3 | 1 | 2 | 2 |
|  | 0.5605 | 0 |  | 0 | 2 | 0 | 0 | 0 | 0 | 0 | 0 | 0 | 0 | 2 | 1 | 3 | 2 | 0 | 0 | 1 |
|  | 0.2803 | 0 |  | 0 | 0 | 0 | 0 | 0 | 0 | 0 | 0 | 0 | 0 | 1 | 0 | 0 | 0 | 0 | 0 | 0 |
|  | 0.1401 | 0 |  | 0 | 0 | 0 | 0 | 0 | 0 | 0 | 0 | 0 | 0 | 0 | 0 | 0 | 0 | 0 | 0 | 0 |
|  | 0.0701 | 0 |  | 0 | 0 | 0 | 0 | 0 | 0 | 0 | 0 | 0 | 0 | 0 | 0 | 0 | 0 | 0 | 0 | 0 |
|  | 0.0350 | 0 |  | 0 | 0 | 0 | 0 | 0 | 0 | 0 | 0 | 0 | 0 | 0 | 0 | 0 | 0 | 0 | 0 | 0 |
|  | 0.0175 | 0 |  | 0 | 0 | 0 | 0 | 0 | 0 | 0 | 0 | 0 | 0 | 0 | 0 | N | 0 | 0 | 0 | 0 |
|  | 0.0087 | N |  | 0 | 0 | 0 | 0 | 0 | 0 | 0 | 0 | 0 | 0 | 0 | 0 | N | 0 | 0 | 0 | 0 |
| 22 | 5.6050 | 3 |  | 3 | 3 | 3 | 3 | 3 | 3 | 3 | 3 | 3 | 3 | 3 | 3 | 3 | 3 | 3 | 3 | 3 |
|  | 1.1210 | 3 |  | 1 | 3 | 3 | 3 | 2 | 3 | 3 | 3 | 3 | 3 | 3 | 3 | 3 | 3 | 3 | 3 | 3 |
|  | 0.5605 | 3 |  | 0 | 3 | 2 | 3 | 3 | 3 | 3 | 3 | 3 | 3 | 3 | 3 | 3 | 3 | 3 | 3 | 3 |
|  | 0.2803 | 3 |  | 0 | 3 | 2 | 3 | 2 | 3 | 3 | 3 | 2 | 3 | 3 | 3 | 3 | 3 | 3 | 3 | 3 |

TABLE B-continued

| Ex. No. | Rate kg/ha | Soybe | Cotze | Rape | Cobuw | Miblw | Mgsle | Hese | Jiwee | Velee | Whez | Rice | Grson | Corn | Dobmi | Prmir | Bycrg | Larct | Grfte | Soble | Colq | Pesw |
|---|---|---|---|---|---|---|---|---|---|---|---|---|---|---|---|---|---|---|---|---|---|---|
|  | 0.1401 | 1 |  |  | 0 | 3 | 3 | 3 | 2 | 3 | 3 | 3 | 2 | 3 | 3 | 3 | 3 | 3 | 3 | 3 | 3 | 3 |
|  | 0.0701 | 0 |  |  | 0 | 3 | 2 | 2 | 2 | 3 | 3 | 3 | 2 | 0 | 3 | 3 | 3 | 3 | 3 | 3 | 3 | 3 |
| 22 | 0.0350 | 0 |  |  | 0 | 0 | 1 | 2 | 1 | 2 | 2 | 2 | 0 | 1 | 3 | 3 | 3 | 3 | 2 | 3 | 3 |
|  | 0.0175 | 0 |  |  | 0 | N | 0 | N | 1 | 1 | 1 | 1 | 0 | 0 | 0 | 3 | 3 | 3 | N | N | 1 |
|  | 0.0087 | 0 |  |  | 0 | 0 | 0 | 0 | 0 | 0 | N | 1 | 0 | 1 | 0 | 1 | 0 | 3 | 0 | 1 | 2 |
| 23 | 5.6050 | 3 |  |  | 0 | 3 | 3 | 3 | 3 | 3 | 3 | 3 | 2 | 3 | 3 | 3 | 3 | 3 | 2 | 3 | 3 |
|  | 1.1210 | 0 |  |  | 0 | 1 | 0 | 1 | 2 | 0 | 2 | 1 | 0 | 2 | 3 | 3 | 3 | 3 | 0 | 3 | 2 |
|  | 0.5605 | 0 |  |  | 0 | 0 | 0 | 0 | 0 | 0 | 1 | 0 | 0 | 0 | 3 | 3 | 3 | 3 | 0 | 0 | 1 |
|  | 0.2803 | 0 |  |  | 0 | 0 | 0 | 0 | 0 | 0 | 0 | 0 | 0 | 0 | 0 | 0 | 2 | 0 | 0 | 0 | 0 |
|  | 0.1401 | 0 |  |  | 0 | 0 | 0 | 0 | 0 | 0 | 0 | 0 | 0 | 1 | 1 | 1 | 1 | 1 | 0 | 0 | 0 |
|  | 0.0701 | 0 |  |  | 0 | 0 | 0 | 0 | 0 | 0 | 0 | 0 | 0 | 0 | 0 | 0 | 0 | 0 | 0 | 0 | 0 |
| 24 | 5.6050 | 0 |  |  | 1 | 3 | 1 | 2 | 3 | 3 | 1 | 3 | 2 | 3 | 3 | 3 | 3 | 3 | 1 | 3 | 3 |
|  | 1.1210 | 0 |  |  | 0 | 2 | 0 | 1 | 1 | 1 | 1 | 2 | 0 | 3 | 3 | 3 | 3 | 3 | 1 | 2 | 3 |
|  | 0.5605 | 0 |  |  | 0 | 1 | 0 | 0 | 0 | 0 | 0 | 0 | 0 | 1 | 1 | 3 | 3 | 2 | 0 | 1 | 0 |
|  | 0.2803 | 0 |  |  | 0 | 0 | 0 | 0 | 0 | 0 | 0 | 0 | 0 | 0 | 0 | 1 | 1 | 0 | 0 | N | 0 |
|  | 0.1401 | 0 |  |  | 0 | 0 | 0 | 0 | 0 | 0 | 0 | 0 | 0 | 0 | 0 | 0 | 0 | 0 | 0 | 0 | 0 |
|  | 0.0701 | 0 |  |  | 0 | 0 | 0 | 0 | 0 | 0 | 0 | 0 | 0 | 0 | 0 | 0 | 0 | 0 | 0 | 1 | 0 |
| 24 | 0.0350 | 0 |  |  | 0 | 0 | 0 | 0 | 0 | 0 | 0 | 0 | 0 | 0 | 0 | 0 | 0 | 0 | 0 | 0 | 0 |
|  | 0.0175 | 0 |  |  | 0 | 0 | 0 | 0 | 0 | 0 | 0 | 0 | 0 | 0 | 0 | 0 | N | 0 | N | N | 0 |
| 25 | 5.6050 | 3 |  |  | 0 | 3 | 3 | 3 | 3 | 3 | 3 | 3 | 3 | 3 | 3 | 3 | 3 | 3 | 3 | 3 | 3 |
|  | 1.1210 | 3 |  |  | 0 | 3 | 3 | 3 | 3 | 3 | 3 | 3 | 3 | 3 | 3 | 3 | 3 | 3 | 3 | 3 | 3 |
|  | 0.5605 | 1 |  |  | 0 | 3 | 2 | 3 | 3 | 3 | 3 | 3 | 3 | 3 | 3 | 3 | 3 | 3 | 3 | 3 | 3 |
|  | 0.2803 | 1 |  |  | 0 | 3 | 1 | 2 | 2 | 2 | N | 3 | 1 | 3 | 3 | 3 | 3 | 3 | 1 | 3 | 3 |
|  | 0.1401 | 1 |  |  | 0 | 2 | 0 | 0 | 2 | 2 | 3 | 1 | 1 | 3 | 3 | 3 | 3 | 3 | 1 | 3 | 3 |
|  | 0.0701 | 0 |  |  | 0 | 0 | 1 | 0 | 1 | 0 | 0 | 2 | 0 | 2 | 3 | 3 | 3 | 3 | 1 | 3 | 3 |
|  | 0.0350 | 0 |  |  | 0 | 1 | 0 | 0 | 0 | 0 | 0 | 1 | 0 | 2 | 3 | 3 | 3 | 3 | 0 | 2 | 3 |
|  | 0.0175 | 0 |  |  | N | 1 | 0 | 0 | 0 | 0 | 0 | 0 | 0 | 0 | 1 | 1 | 2 | 2 | 0 | 0 | 0 |
| 26 | 5.6050 | 3 |  |  | 3 | 3 | 3 | 3 | 3 | 3 | 3 | 3 | 3 | 3 | 3 | 3 | 3 | 3 | 3 | 3 | 3 |
|  | 1.1210 | 3 |  |  | 3 | 3 | 3 | 3 | 3 | 3 | 3 | 3 | 3 | 3 | 3 | 3 | 3 | 3 | 3 | 3 | 3 |
|  | 0.5605 | 3 |  |  | 1 | 3 | 2 | 3 | 3 | 3 | 3 | 3 | 3 | 3 | 3 | 3 | 3 | 3 | 3 | 3 | 3 |
|  | 0.2803 | 3 |  |  | 1 | 3 | 2 | 3 | 3 | 3 | 3 | 3 | 2 | 3 | 3 | 3 | 3 | 3 | 3 | 3 | 3 |
|  | 0.1401 | 3 |  |  | 2 | 3 | 1 | 3 | 3 | 3 | 3 | 3 | 2 | 3 | 3 | 3 | 3 | 3 | 3 | 3 | 3 |
| 26 | 0.0701 | 3 |  |  | 0 | 3 | 1 | 3 | 3 | 3 | 3 | 3 | 2 | 3 | 3 | 3 | 3 | 3 | 3 | 3 | 3 |
|  | 0.0350 | 2 |  |  | 0 | 3 | 1 | 2 | 3 | 1 | 1 | 2 | 1 | 3 | 3 | 3 | 3 | 3 | 3 | 3 | 3 |
|  | 0.0175 | 1 |  |  | 1 | 3 | 0 | 2 | 2 | 2 | 1 | 2 | 0 | 2 | 3 | 3 | 3 | 3 | 1 | 3 | 3 |
|  | 0.0087 | 1 |  |  | 0 | 3 | 0 | 1 | 2 | 1 | 1 | 1 | 0 | 2 | 3 | 2 | 3 | 3 | 0 | 3 | 3 |
| 27 | 5.6050 | 2 |  |  | 0 | 3 | 2 | 3 | 3 | 3 | 3 | 3 | 2 | 3 | 3 | 3 | 3 | 3 | 3 | 3 | 3 |
|  | 1.1210 | 0 |  |  | 0 | 3 | 0 | 2 | 3 | 0 | 1 | 1 | 1 | 3 | 3 | 3 | 3 | 2 | 3 | 3 |
|  | 0.5605 | 0 |  |  | 0 | 2 | 0 | 2 | 2 | 0 | 0 | 1 | 0 | 3 | 3 | 3 | 3 | 1 | 3 | 3 |
|  | 0.2803 | 0 |  |  | 0 | 2 | 0 | 0 | 0 | 0 | 0 | 0 | 0 | 3 | 2 | 3 | 3 | 0 | 3 | 1 |
|  | 0.1401 | 0 |  |  | 0 | 0 | 0 | 0 | 0 | 0 | 0 | 0 | 0 | 2 | 3 | 3 | 3 | 0 | 0 | 0 |
|  | 0.0701 | 0 |  |  | 0 | 0 | 0 | 0 | 0 | 0 | 0 | 0 | 0 | 1 | 3 | 3 | 1 | 0 | 0 | 0 |
|  | 0.0350 | 0 |  |  | 0 | 0 | 0 | 0 | 0 | 0 | 0 | 0 | 0 | 0 | 0 | 2 | 1 | 0 | 0 | 0 |
|  | 0.0175 | 0 |  |  | 0 | 0 | 0 | 0 | 0 | 0 | 0 | 0 | 0 | 0 | 0 | 1 | 2 | 0 | 0 | 0 |
| 28 | 5.6050 | 3 |  |  | 0 | 3 | 2 | 3 | 3 | 3 | 3 | 3 | 3 | 3 | 3 | 3 | 3 | 3 | 3 | 3 | 3 |
|  | 1.1210 | 0 |  |  | 0 | 1 | 1 | 2 | 3 | 3 | 2 | 3 | 3 | 3 | 3 | 3 | 3 | 3 | 3 | 3 | 3 |
|  | 0.5605 | 0 |  |  | 0 | 0 | 0 | 0 | 0 | 3 | 3 | 3 | 2 | 3 | 3 | 3 | 3 | 3 | 2 | 2 | 3 |
| 28 | 0.2803 | 0 |  |  | 0 | 0 | 0 | 0 | 0 | 1 | 2 | 1 | 0 | 2 | 3 | 3 | 2 | 2 | 2 | 0 | 2 |
|  | 0.1401 | 0 |  |  | 0 | N | 0 | 0 | 0 | 0 | 1 | 0 | 0 | 3 | 2 | 2 | 0 | 1 | N | N | 1 |
|  | 0.0701 | 0 |  |  | 0 | N | 0 | 0 | 0 | 0 | 0 | 0 | 0 | 0 | 0 | 0 | 0 | 0 | 0 | 0 | 1 |
|  | 0.0350 | 0 |  |  | 0 | 0 | 0 | 0 | 0 | 0 | 0 | 0 | 0 | 0 | 0 | 0 | 0 | 0 | 0 | 0 | 0 |
|  | 0.0175 | 0 |  |  | 0 | 0 | 0 | 0 | 0 | 0 | 0 | 0 | 0 | 0 | 0 | 0 | 0 | 0 | 0 | 0 | 0 |
|  | 0.0087 | 0 |  |  | 0 | 0 | 0 | 0 | 0 | 0 | 0 | 0 | 0 | 0 | 0 | 0 | 0 | 0 | 0 | 0 | 0 |
| 29 | 5.6050 | 3 |  |  | 2 | 3 | 3 | 3 | 3 | 3 | 3 | 3 | 3 | 3 | 3 | 3 | 3 | 3 | 3 | 3 | 3 |
|  | 1.1210 | 3 |  |  | 0 | 3 | 3 | 3 | 3 | 3 | 3 | 3 | 3 | 3 | 3 | 3 | 3 | 3 | 3 | 3 | 3 |
|  | 0.5605 | 1 |  |  | 0 | 1 | 0 | 3 | 3 | 3 | 3 | 3 | 3 | 3 | 3 | 3 | 3 | 3 | 3 | 3 | 3 |
|  | 0.2803 | 0 |  |  | 0 | 1 | 0 | 2 | 3 | 3 | 3 | 3 | 1 | 3 | 3 | 3 | 3 | 3 | 3 | 3 | 3 |
|  | 0.1401 | 0 |  |  | 0 | 1 | 0 | 1 | 2 | 2 | 2 | 2 | 0 | 3 | 3 | 3 | 3 | 3 | 3 | 2 | 3 |
|  | 0.0701 | 0 |  |  | 0 | N | 0 | 0 | 0 | 2 | 2 | 1 | N | 3 | 3 | 3 | 3 | 3 | N | 3 | N |
|  | 0.0350 | 0 |  |  | 0 | 0 | 0 | 0 | 0 | 2 | 1 | 0 | 0 | 2 | 3 | 3 | 3 | 2 | 0 | 0 | 0 |
|  | 0.0175 | 0 |  |  | 0 | 0 | 0 | 0 | 0 | 0 | 0 | 0 | 0 | 3 | 2 | 1 | 3 | 0 | 0 | N | N |
| 32 | 5.6050 | 3 |  |  | 3 | 3 | 3 | 3 | 3 | 3 | 3 | 3 | 3 | 3 | 3 | 3 | 3 | 3 | 3 | 3 | 3 |
|  | 1.1210 | 3 |  |  | 0 | 3 | 3 | 3 | 3 | 3 | 3 | 3 | 3 | 3 | 3 | 3 | 3 | 3 | 3 | 3 | 3 |
|  | 0.5605 | 3 |  |  | 0 | 3 | 1 | 3 | 3 | 3 | 3 | 3 | 3 | 3 | 3 | 3 | 3 | 3 | 3 | 3 | 3 |
|  | 0.2803 | 3 |  |  | 0 | 3 | 2 | 3 | 3 | 3 | 3 | 3 | 2 | 3 | 3 | 3 | 3 | 3 | 3 | 3 | 3 |
|  | 0.1401 | 2 |  |  | 0 | 3 | 1 | 2 | 2 | 3 | 2 | 3 | 1 | 3 | 3 | 3 | 3 | 3 | 3 | 3 | 3 |
|  | 0.0701 | 0 |  |  | 0 | 2 | 0 | 1 | 2 | 1 | 3 | 3 | 0 | 3 | 3 | 3 | 3 | 3 | 2 | 3 | 1 |
|  | 0.0350 | 0 |  |  | 0 | 3 | 0 | 1 | 1 | 0 | 2 | 0 | 0 | 3 | 3 | 2 | 3 | 1 | 3 | 3 | 2 |
|  | 0.0175 | 0 |  |  | 1 | 2 | 0 | 0 | 0 | 0 | 1 | 0 | 0 | 3 | 3 | 1 | 3 | 1 | 1 | 3 | 1 |
|  | 0.0087 | 0 |  |  | 1 | 1 | 0 | 0 | 0 | 0 | 0 | 0 | 0 | 2 | 0 | 0 | 0 | 0 | 0 | 2 | 0 |
|  | 0.0044 | 0 |  |  | 0 | N | 0 | 0 | 0 | 0 | 0 | 0 | 0 | 2 | 0 | 0 | N | 0 | N | N | N |
| 33 | 5.6050 | 3 | 2 | 3 | 1 | 3 | 3 | 3 | 3 | 3 | 3 | 3 | 3 | 3 | 3 | 3 | 3 | 3 | 3 |  |  |  |
|  | 1.1210 | 1 | 2 | 3 | N | 3 | 3 | 3 | 3 | 3 | 3 | 3 | 3 | 2 | 3 | 3 | 3 | 3 | 3 |  |  |  |
|  | 0.2803 | 0 | 2 | 2 | N | 3 | 0 | 3 | 3 | 3 | 2 | 3 | 2 | 0 | 3 | 3 | 3 | 3 | 3 |  |  |  |
|  | 0.0701 | 0 | 1 | 1 | 0 | 0 | 0 | 0 | 0 | 1 | 1 | 0 | 0 | 0 | 3 | 3 | 1 | 3 |  |  |  |  |
| 34 | 5.6050 | 3 | 0 | 3 | 0 | 3 | 3 | 3 | 3 | 3 | 3 | 3 | 3 | 0 | 3 | 3 | 3 | 3 | 3 |  |  |  |
|  | 1.1210 | 0 | N | 3 | 0 | 3 | 3 | 3 | 3 | 3 | 3 | 3 | 3 | 2 | 3 | 3 | 3 | 3 | 3 |  |  |  |
|  | 0.2803 | 1 | 0 | 1 | 0 | 1 | 2 | 1 | 2 | 1 | 2 | 3 | 3 | 1 | 3 | 3 | 3 | 3 | 3 |  |  |  |

TABLE B-continued

| Ex. No. | Rate kg/ha | Sobe | Cotz | Rape | Cobu | Wibw | Mogl | Hese | Jiwe | Vele | Whez | Rico | Grsr | Cobr | Dmbi | Prmi | Brgr | Lact | Grft | Subeq | Colq | Pesw |
|---|---|---|---|---|---|---|---|---|---|---|---|---|---|---|---|---|---|---|---|---|---|---|
|  | 0.0701 | 0 | N | 0 | N | 0 | 0 | 0 | 0 | 0 | 0 | 0 | 0 | 0 | 0 | 0 | 1 | 0 | | | | |
|  | 0.0175 | 0 | 0 | 0 | 0 | 0 | 0 | 0 | 0 | 0 | 0 | 0 | 0 | 0 | N | 0 | 0 | 0 | | | | |
|  | 0.0087 | 0 | 0 | 0 | 0 | 1 | 0 | 0 | 1 | 0 | 0 | 0 | 0 | 0 | N | 0 | 0 | 0 | | | | |
| 35 | 5.6050 | 3 | 3 | 3 | 3 | 3 | 3 | 3 | 3 | 3 | 3 | 3 | 3 | 3 | 3 | 3 | 3 | 3 | | | | |
|  | 1.1210 | 3 | 3 | 3 | 1 | 3 | 3 | 3 | 3 | 3 | 3 | 3 | 3 | 3 | 3 | 3 | 3 | 3 | | | | |
|  | 0.2803 | 3 | 0 | 3 | 0 | 3 | 3 | 3 | 3 | 3 | 3 | 3 | 3 | 3 | 3 | 3 | 3 | 3 | | | | |
|  | 0.0701 | 1 | 0 | 2 | 0 | 3 | 0 | 2 | 3 | 3 | 3 | 3 | 1 | 3 | 3 | 3 | 3 | 3 | | | | |
|  | 0.0175 | 1 | 0 | 0 | 0 | 3 | 1 | 2 | 3 | 1 | 1 | 1 | 1 | 0 | 3 | 3 | 1 | 3 | 3 | | | | |
|  | 0.0087 | 1 | 0 | 0 | 0 | 2 | 0 | 2 | 1 | 1 | 1 | 0 | 2 | 0 | 3 | N | 3 | 2 | | | | |
| 37 | 5.6050 | 3 | 2 | 3 | 1 | 3 | 3 | 3 | 3 | 3 | 3 | 3 | 3 | 3 | 3 | 3 | 3 | 3 | | | | |
|  | 1.1210 | 1 | 0 | 3 | 0 | 3 | 2 | 3 | 3 | 3 | 3 | 3 | 0 | 3 | 3 | 3 | 3 | 3 | | | | |
|  | 0.2803 | 1 | 0 | 0 | 1 | 2 | 0 | 0 | 2 | 0 | 2 | 0 | 0 | 0 | 3 | 3 | 3 | 3 | | | | |
| 37 | 0.0701 | 0 | 0 | 0 | 0 | 0 | 0 | 0 | 1 | 0 | 0 | 1 | 0 | 0 | 0 | 0 | 3 | 0 | | | | |
|  | 0.0175 | 0 | 0 | 0 | 0 | 0 | 0 | 0 | 0 | 0 | 0 | 0 | 0 | 0 | 0 | 0 | 1 | 0 | | | | |
|  | 0.0087 | 0 | 0 | 0 | 0 | 0 | 0 | 0 | 0 | 0 | 0 | 0 | 0 | 0 | 0 | 0 | 0 | 0 | | | | |
| 38 | 5.6050 | 3 | 2 | 3 | 1 | 3 | 3 | 3 | 3 | 3 | 3 | 3 | 3 | 3 | 3 | 3 | 3 | 3 | | | | |
|  | 1.1210 | 3 | 1 | 3 | 0 | 3 | 3 | 3 | 3 | 3 | 3 | 3 | 1 | 3 | 3 | 3 | 3 | 3 | | | | |
|  | 0.2803 | 0 | 2 | 3 | 0 | 3 | 0 | 0 | 2 | 0 | 3 | 3 | 0 | 3 | 3 | 3 | 3 | 3 | | | | |
|  | 0.0701 | 0 | 1 | 0 | 0 | 3 | 0 | 0 | N | 0 | 1 | 1 | 1 | 0 | 3 | 0 | 3 | 3 | 2 | | | | |
|  | 0.0175 | 0 | 0 | 0 | 0 | 0 | 0 | 0 | 2 | 0 | 0 | 0 | 0 | 0 | 2 | 0 | 0 | 2 | 0 | | | | |
|  | 0.0087 | 0 | 1 | 0 | 0 | 1 | 0 | N | 3 | N | 1 | 0 | 0 | 0 | 3 | 1 | 0 | 0 | 1 | | | | |
| 39 | 5.6050 | 2 | | | 0 | 2 | 2 | 2 | | 3 | 3 | 3 | 3 | 2 | 3 | 3 | 3 | 3 | 3 | 3 | 3 | 3 |
|  | 1.1210 | 1 | | | 0 | 2 | 0 | 1 | | 1 | 1 | 2 | 2 | 0 | 3 | 2 | 2 | 3 | 3 | 1 | 3 | 2 |
|  | 0.5605 | 0 | | | 0 | N | 0 | 0 | | 0 | 0 | 0 | 3 | 0 | 2 | 3 | 3 | 3 | 3 | 0 | N | 1 |
|  | 0.2803 | 0 | | | 0 | 0 | 1 | 0 | | 0 | 0 | 0 | 0 | 0 | 0 | 0 | 1 | 0 | 0 | 0 | 0 | 0 |
|  | 0.1401 | 0 | | | 0 | 1 | 0 | 0 | | 0 | 0 | 0 | 0 | 0 | 1 | 0 | 1 | 1 | 0 | 0 | 0 | 0 |
|  | 0.0701 | 0 | | | 0 | 0 | 0 | 0 | | 0 | 0 | 0 | 0 | 0 | 1 | 0 | 0 | 0 | N | 0 | 0 | 0 |
| 40 | 5.6050 | 3 | 2 | 3 | 0 | 3 | 3 | 3 | 3 | 3 | 3 | 3 | 3 | 3 | 3 | 3 | 3 | 3 | 3 | | | |
|  | 1.1210 | 1 | 0 | 3 | N | 3 | 2 | 3 | 3 | 3 | 2 | 3 | 3 | 1 | 3 | 3 | 3 | 3 | 3 | | | |
|  | 0.2803 | 1 | 1 | 0 | 0 | 0 | 0 | 1 | 1 | 1 | 0 | 1 | 0 | 1 | 3 | 3 | 0 | 3 | 3 | | | |
|  | 0.0701 | 0 | 0 | 0 | 0 | 0 | 0 | 0 | 0 | 0 | 0 | 0 | 0 | 3 | 0 | 0 | 3 | 0 | | | | |
|  | 0.0175 | 0 | 0 | 0 | 0 | 0 | 0 | 0 | 0 | 0 | 0 | 0 | 0 | 0 | 0 | 0 | 0 | 0 | | | | |
| 41@ | 5.6050 | 3 | 3 | 3 | N | 3 | 3 | 3 | 3 | 3 | 3 | 3 | 3 | 3 | 3 | 3 | 3 | 3 | 3 | | | |
| @ | 1.1210 | 3 | 3 | 0 | N | 3 | 2 | 0 | 3 | 0 | 3 | 3 | 3 | 3 | 3 | 3 | 3 | 3 | 3 | | | |
| @ | 0.2803 | 2 | 3 | 0 | N | 1 | 0 | 0 | 0 | 0 | 0 | 3 | 1 | 2 | 3 | 3 | 2 | 2 | 1 | | | |
| @ | 0.0701 | 2 | 1 | 0 | N | N | 0 | N | N | 1 | 0 | 1 | 0 | 0 | 0 | 0 | 0 | 1 | 0 | | | |
| 42@ | 5.6050 | 3 | 2 | 3 | N | 3 | 3 | 3 | 3 | 3 | 3 | 3 | 3 | 3 | 3 | 3 | 3 | 3 | 3 | | | |
| @ | 1.1210 | 3 | 2 | 3 | N | 3 | 3 | 3 | 3 | 3 | 3 | 3 | 3 | 3 | 3 | 3 | 3 | 3 | 3 | | | |
| @ | 0.2803 | 1 | 2 | 1 | N | 3 | 1 | 3 | 3 | 3 | 3 | 3 | 3 | 2 | 3 | 3 | 3 | 3 | 3 | | | |
| @ | 0.0701 | 0 | 0 | 0 | N | 0 | 0 | 0 | 1 | 0 | 0 | 3 | 1 | 1 | 1 | 1 | 3 | 3 | 3 | | | |
| 43@ | 5.6050 | 3 | 2 | 3 | N | 3 | 3 | 3 | 2 | 3 | 3 | 3 | 3 | 3 | 3 | 3 | 3 | 3 | 3 | | | |
| @ | 1.1210 | 3 | 2 | 3 | N | 3 | 2 | 1 | 3 | 2 | 3 | 3 | 3 | 3 | 3 | 3 | 3 | 3 | 3 | | | |
| @ | 0.2803 | 0 | 2 | 0 | N | 1 | 0 | 1 | 1 | 2 | 1 | 3 | 2 | 2 | 3 | 0 | 3 | 3 | 3 | | | |
| @ | 0.0701 | 0 | 1 | 0 | N | 0 | 1 | 0 | 2 | 0 | 0 | 1 | 0 | 0 | 1 | 0 | 0 | 0 | 0 | | | |
| @ | 0.0175 | 0 | 0 | 0 | N | 0 | 0 | 0 | 1 | 0 | 0 | 0 | 0 | 1 | 0 | 0 | 0 | 0 | 0 | | | |
| @ | 0.0087 | 0 | 0 | 0 | N | 0 | 0 | 0 | 1 | 0 | 0 | 0 | 0 | 0 | 0 | 0 | 0 | 0 | 0 | | | |
| 44+ | 5.6050 | 3 | 2 | 3 | 1 | 3 | 3 | 3 | 2 | 3 | 3 | 3 | 3 | 3 | 3 | 3 | 3 | 3 | 3 | | | |
| + | 1.1210 | 3 | 3 | 3 | 1 | 3 | 3 | 3 | 2 | 3 | 3 | 3 | 2 | 3 | 3 | 3 | 3 | 3 | 3 | | | |
| + | 0.5605 | 3 | 0 | 3 | 0 | 3 | 3 | 3 | 3 | 3 | 3 | 3 | 1 | 3 | 3 | 3 | 3 | 3 | 3 | | | |
| + | 0.2803 | 3 | 0 | 3 | 0 | 3 | 3 | 1 | 3 | 3 | 3 | 3 | 3 | 3 | 3 | 3 | 3 | 3 | 3 | | | |
| + | 0.1401 | 3 | N | 3 | 0 | 2 | 1 | 1 | 3 | 3 | 3 | 3 | 1 | 3 | 3 | 3 | 3 | 3 | 3 | | | |
| + | 0.0701 | 1 | 1 | 3 | 0 | 1 | 1 | 1 | 2 | 1 | 2 | 2 | 1 | 0 | 3 | 3 | 3 | 3 | 3 | | | |
| + | 0.0351 | 2 | 2 | 3 | 0 | 1 | 0 | N | 1 | 2 | 2 | 1 | 0 | 3 | 2 | 3 | 3 | 3 | 3 | | | |
| + | 0.0175 | 0 | 0 | 1 | 0 | 1 | 1 | 0 | 1 | 0 | 1 | 0 | 0 | 3 | 0 | 2 | 3 | 3 | 3 | | | |
| 45 | 5.6050 | 0 | 0 | 0 | N | 2 | 0 | 0 | 2 | 0 | 0 | 1 | 0 | 3 | 3 | N | 3 | 1 | | | | |
|  | 1.1210 | 0 | 1 | 0 | N | 2 | 0 | 1 | 2 | 0 | 0 | 1 | 0 | 0 | 3 | 0 | 0 | 3 | 1 | | | |
|  | 0.2803 | N | 0 | 1 | N | 1 | N | 0 | 1 | 0 | N | N | N | 1 | 0 | 0 | 1 | N | | | | |
| 50 | 5.6050 | 3 | 0 | 3 | 3 | 3 | 3 | 3 | 3 | 3 | 3 | 3 | 3 | 3 | 3 | 3 | 3 | 3 | 3 | | | |
|  | 1.1210 | 2 | 1 | 3 | 0 | 3 | 3 | 3 | 1 | 3 | 3 | 3 | 3 | 3 | 3 | 3 | 3 | 3 | 3 | | | |
|  | 0.2803 | 1 | 0 | 2 | N | 2 | 0 | 0 | 2 | 1 | 3 | 1 | 3 | 1 | 3 | 3 | 3 | 3 | 3 | | | |
|  | 0.0701 | 1 | 1 | 0 | 0 | 3 | 0 | 1 | 0 | 1 | 2 | 0 | 3 | 0 | 3 | 2 | 3 | 3 | 3 | | | |
|  | 0.0175 | 0 | 0 | 0 | 0 | 0 | 0 | 0 | 0 | 1 | 0 | 0 | 1 | 0 | 1 | 0 | 0 | 0 | 1 | | | |
|  | 0.0087 | 0 | 0 | 0 | 0 | 0 | 0 | 0 | 1 | 0 | 0 | 0 | 0 | 0 | 0 | 0 | 0 | 0 | | | | |
| 51 | 5.6050 | 2 | 0 | 3 | 0 | 3 | 3 | 3 | 3 | 3 | 3 | 3 | 3 | 3 | 3 | 3 | 3 | 3 | 3 | | | |
|  | 1.1210 | 0 | 0 | 2 | 0 | 3 | 0 | 2 | 3 | 2 | 2 | 3 | 3 | 0 | 3 | 3 | 1 | 3 | 3 | | | |
|  | 0.2803 | 0 | 0 | 1 | 0 | 1 | 0 | 0 | 1 | 1 | 1 | 1 | 0 | 0 | 3 | 1 | 0 | 3 | 3 | | | |
|  | 0.0701 | 0 | 0 | 0 | 0 | 1 | 0 | 0 | 1 | 0 | 0 | 0 | 0 | 0 | 0 | 1 | 0 | 0 | 0 | | | |
|  | 0.0175 | 0 | 0 | 0 | 0 | 0 | 0 | 0 | 0 | 0 | 0 | 0 | 0 | 0 | 0 | 0 | 0 | 0 | 0 | | | |
| 52 | 5.6050 | 3 | 3 | 3 | 3 | 3 | 3 | 3 | 3 | 3 | 3 | 3 | 3 | 3 | 3 | 3 | 3 | 3 | 3 | | | |
|  | 1.1210 | 3 | 2 | 3 | 3 | 3 | 3 | 3 | 3 | 3 | 3 | 3 | 3 | 3 | 3 | 3 | 3 | 3 | 3 | | | |
|  | 0.2803 | 3 | 1 | 3 | 0 | 3 | 3 | 3 | 3 | 3 | 3 | 3 | 3 | 3 | 3 | 3 | 3 | 3 | 3 | | | |
|  | 0.0701 | 1 | 0 | 3 | 0 | 3 | 0 | 3 | 3 | 3 | 3 | 3 | 2 | 3 | 3 | 3 | 3 | 3 | | | | |
|  | 0.0175 | 0 | 0 | 0 | 0 | 3 | 0 | 0 | 1 | 0 | 1 | 2 | 1 | 0 | 3 | 3 | 3 | 3 | 1 | | | |
|  | 0.0087 | 0 | N | 0 | 0 | 0 | 0 | 0 | 0 | 1 | 1 | 0 | 2 | 0 | 1 | 3 | 1 | 1 | 2 | | | |
| 53 | 5.6050 | 3 | 2 | 3 | 1 | 3 | 3 | 3 | 3 | 3 | 3 | 3 | 3 | 3 | 3 | 3 | 3 | 3 | 3 | | | |
|  | 1.1210 | 2 | 0 | 3 | 0 | 3 | 2 | 3 | 3 | 3 | 3 | 3 | 3 | 3 | 3 | 3 | 3 | 3 | 3 | | | |
|  | 0.2803 | 0 | 0 | 1 | 0 | 2 | 0 | 1 | 1 | 1 | 3 | 1 | 3 | 0 | 3 | 3 | 3 | 3 | 3 | | | |
|  | 0.0701 | 0 | 0 | 0 | 0 | 0 | 0 | 0 | 0 | 1 | 0 | 0 | 0 | 0 | 2 | 1 | 1 | 1 | 3 | | | |

TABLE B-continued

| Ex. No. | Rate kg/ha | Sobe | Cotze | Rape | Cobuw | Wibw | Mogl | Hese | Jiwee | Vleez | Whece | Rize | Grson | Cobnr | Dobmir | Pyrmirg | Brgct | Lafbt | Grseq | Sobeq | Cobeq | Pesw |
|---|---|---|---|---|---|---|---|---|---|---|---|---|---|---|---|---|---|---|---|---|---|---|
|  | 0.0175 | 0 | 0 | 0 | 0 | 0 | 0 | 0 | 0 | 0 | 0 | 0 | 0 | 0 | 0 | 0 | 0 | 0 |  |  |  |  |
|  | 0.0087 | 0 | 0 | 0 | 0 | 0 | 0 | 0 | 0 | 0 | 0 | 0 | 0 | 0 | 0 | 0 | 0 | 0 |  |  |  |  |
| 54+ | 5.6050 | 3 | 1 | 3 | N | 3 | 3 | 2 | 3 | 3 | 3 | 3 | 3 | 3 | 3 | 3 | 3 | 3 |  |  |  |  |
| + | 1.1210 | 2 | 1 | 3 | N | 3 | 1 | 3 | 1 | 1 | 1 | 3 | 3 | 2 | 3 | 3 | 3 | 3 | 3 |  |  |  |
| + | 0.2803 | 0 | 1 | 1 | N | 0 | 1 | 0 | 0 | 0 | 1 | 1 | 3 | 0 | 3 | 2 | 2 | 3 | 2 |  |  |  |
| + | 0.0701 | 0 | 0 | 0 | N | 0 | 0 | 0 | 0 | 0 | 0 | 0 | 0 | 0 | 0 | 0 | 0 | 0 | 0 |  |  |  |
| + | 0.0175 | 0 | 0 | 0 | N | 0 | 0 | 0 | 0 | 0 | 0 | 0 | 0 | 0 | 0 | 0 | 0 | 0 | 0 |  |  |  |
| + | 0.0087 | 0 | N | 0 | N | 0 | 0 | 0 | 0 | 0 | 0 | 1 | 0 | 0 | 0 | 0 | 0 | 0 | 0 |  |  |  |
| 55 | 5.6050 | 2 | 2 | 3 | 2 | 3 | 3 | 3 | 3 | 3 | 3 | 3 | 3 | 3 | 3 | 3 | 3 | 3 | 3 |  |  |  |
|  | 1.1210 | 0 | 0 | 3 | 0 | 3 | 2 | 1 | 3 | 1 | 2 | 3 | 3 | 1 | 3 | 3 | 3 | 3 | 3 |  |  |  |
|  | 0.2803 | 0 | 0 | 0 | N | 0 | 0 | 0 | 1 | 0 | 0 | 2 | 0 | 0 | 3 | 3 | 0 | 3 | 3 |  |  |  |
|  | 0.0701 | 0 | N | 0 | 0 | 0 | 0 | 0 | 0 | 0 | 0 | 0 | 0 | 0 | 0 | 0 | 0 | 0 | 0 |  |  |  |
| 55 | 0.0175 | N | 0 | 0 | 0 | 0 | 0 | 0 | 0 | 0 | 0 | 0 | 0 | 0 | 0 | 0 | 0 | 1 | 0 |  |  |  |
|  | 0.0175 | N | 0 | 0 | 0 | 0 | 0 | 0 | 0 | 0 | 0 | 0 | 0 | 0 | 0 | 0 | 0 | 1 | 0 |  |  |  |

*CHEAT GRASS REPLACING DOWNYBROME
  POOR GERMINATION OR EMERGENCE OF MOGL AND COBU
@ NO DATA FOR COBU DUE TO POOR EMERGENCE
+ RICE POOR THROUGHOUT TEST
+ COBU EMERGENCE AND RICE GROWTH VARIABLE

POST-EMERGENT HERBICIDE EXAMPLES

Although as has been stated above the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In most of the tests which follow, larger and more developed plants were used.

The post-emergence herbicidal activity of compounds of this invention was demonstrated by greenhouse testing, and the results are shown in the following Table C. The post-emergent herbicidal activity index used in Table C is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — or a blank |
| Species planted, no data | N |

As was the case with the pre-emergence data, some of the compounds initially received ratings for plant response directly as percent inhibition in ten percent increments. Where this is the case, the percentage has been converted according to the scale above.

POST-EMERGENCE ACTIVITY ON WEEDS

Topsoil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was removed to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/Ha (200 gallons/acre). The pans were returned to the greenhouse and watered as before and the injury to the plants as compared to those in control pans was observed at approximately 10–14 days (usually 11 days) and in some instances observed again at 24–28 days (usually 25 days) after spraying. These latter observations are designated by a "pound" sign (#) following the column of example numbers in the Table. The plant species used in this set of tests were the same as those used in the first set of pre-emergence tests, and the plant identifying codes are the same as those shown for Table A. As above, footnotes follow the Table.

TABLE C

| Ex. No. | Rate kg/ha | Yens | Abng | Sjgr | Dobyr | Bygr | Mgl | Cobu | Vble | Imu | Cbtwh | Clstq | Prsw | Rhqg | Rhjg |
|---|---|---|---|---|---|---|---|---|---|---|---|---|---|---|---|
| 1 | 11.2100 | 0 |  |  | 0 | 0 | 0 | 0 | 0 |  | N | 0 | 0 | 0 | 0 |
| 2 | 11.2100 | 0 |  |  | 0 | 0 | 0 | 0 | 1 |  | 0 | 0 | 0 | 0 | 0 |
| 3 | 11.2100 | 0 |  |  | 0 | 0 | 1 | 1 | 0 |  | 0 | 0 | 0 | 0 | N |
| 4 | 11.2100 | 0 |  |  | 0 | 0 | 0 | 0 | 0 |  | 0 | 0 | 0 | 0 | 0 |
| 5 | 11.2100 | 0 |  |  | 0 | 0 | 0 | 1 | 0 |  | 0 | 4 | 0 | 0 | 0 |
| 6 | 11.2100 | 0 |  |  | 0 | 0 | 0 | 0 | 0 |  | 0 | 0 | 0 | 0 | 0 |
| 7 | 11.2100 | 0 |  |  | 0 | 0 | 0 | 0 | 0 |  | 0 | 0 | 0 | 0 | 0 |
| 8 | 11.2100 | 0 |  |  | 0 | 0 | 0 | 0 | 0 |  | 0 | 0 | 0 | 0 | 0 |
| 9 | 11.2100 | 0 |  |  | 0 | 0 | 0 | 0 | 0 |  | 0 | 0 | 0 | 0 | N |
| 10 | 11.2100 | 0 |  |  | 0 | 0 | 0 | 0 | 0 |  | N | 0 | 0 | 0 | 0 |
| 11 | 11.2100 | 0 |  |  | 0 | 0 | 0 | 1 | 0 |  | 0 | 0 | 0 | 0 | 0 |

TABLE C-continued

| Ex. No. | Rate kg/ha | Yens | Anbg | Sejg | Dobr | Bygr | Mogl | Cobu | Vele | Inmu | Wibw | Cath | Coq | Pesw | Rhhq | Rhjg |
|---|---|---|---|---|---|---|---|---|---|---|---|---|---|---|---|---|
| 12 | 11.2100 | 0 | | | 0 | 3 | 0 | 1 | 0 | | | 0 | 4 | 1 | 0 | 0 |
| 13 | 11.2100 | 0 | | | 0 | 0 | 0 | 0 | 0 | | | 0 | 0 | 0 | 0 | 0 |
| 14 | 11.2100 | 0 | | | 0 | 2 | 1 | 2 | 0 | | | 0 | 0 | 1 | 0 | 0 |
| 15 | 11.2100 | 0 | | | 0 | 0 | 0 | 0 | 0 | | | 0 | 4 | 0 | 0 | 0 |
| 16 | 11.2100 | 0 | | | 0 | 1 | 1 | 1 | 1 | | | N | 0 | 0 | 0 | 0 |
| 17 | 11.2100 | 0 | | | 0 | 0 | 0 | 1 | 1 | | | 0 | 1 | 1 | 0 | 0 |
| 18 | 11.2100 | 0 | | | 0 | 0 | 0 | 0 | 0 | | | 0 | 0 | 0 | 0 | 0 |
| 19 | 11.2100 | 0 | | | 0 | 1 | 0 | 1 | 0 | | | 0 | 0 | 0 | 0 | 0 |
| 20 | 11.2100 | 0 | | | 0 | 1 | 0 | 0 | 0 | | | 0 | 0 | 0 | 0 | 0 |
| 21 | 11.2100 | 0 | | | 0 | 0 | 0 | 1 | 0 | | | 0 | 0 | 0 | 0 | 0 |
| 22 | 11.2100 | 0 | | | 0 | 0 | 0 | 0 | 0 | | | 0 | 0 | 1 | 0 | 0 |
| 23 | 11.2100 | 0 | | | 0 | 0 | 0 | 0 | 0 | | | 0 | 0 | 0 | 0 | 0 |
| 24 | 11.2100 | 0 | | | 0 | 0 | 0 | 0 | 0 | | | 0 | 2 | 1 | 0 | 0 |
| 25 | 11.2100 | 0 | | | 0 | 0 | 0 | 0 | 0 | | | 0 | 1 | 0 | 0 | 0 |
| 26 | 11.2100 | 0 | | | 0 | 0 | 0 | 0 | 0 | | | 0 | 0 | 0 | 0 | 0 |
| 27 | 11.2100 | 0 | | | 0 | 0 | 0 | 0 | 0 | | | 0 | N | 0 | 0 | 0 |
| 28 | 11.2100 | 0 | | | 0 | 0 | 0 | 0 | 0 | | | 0 | 0 | 0 | 0 | 0 |
| 29 | 11.2100 | 0 | | | 0 | 0 | 0 | 0 | 0 | | | 0 | 0 | 0 | 0 | 0 |
| 30 | 11.2100 | 0 | | | 0 | 0 | 0 | 0 | 0 | | | 0 | 0 | 0 | 0 | 0 |
| 31 | 11.2100 | 0 | | | 0 | 0 | 0 | 0 | 0 | | | 0 | 0 | 0 | 0 | 0 |
| 32 | 11.2100 | 0 | | | 0 | 0 | 0 | 0 | 0 | | | 0 | 0 | 0 | 0 | 0 |
| 33 | 11.2100 | 0 | 0 | 0 | 0 | 0 | 0 | 1 | 1 | 0 | 0 | | | | | |
| 34 | 11.2100 | 0 | 0 | 2 | 0 | 1 | 0 | 0 | 0 | 0 | 0 | | | | | |
| 35 | 11.2100 | 0 | 0 | 3 | 0 | 2 | 2 | 0 | 1 | 1 | 2 | | | | | |
| 36* | 11.2100 | 0 | 0 | 2 | 0 | 2 | 2 | 2 | 2 | 2 | 2 | | | | | |
| 37 | 11.2100 | 0 | 2 | 2 | 0 | 2 | 2 | 2 | 2 | 2 | 2 | | | | | |
| 38 | 11.2100 | 0 | 0 | 2 | 0 | 2 | 2 | 0 | 2 | 1 | 2 | | | | | |
| 39 | 11.2100 | 0 | | | 0 | 0 | 0 | 0 | 0 | | | 0 | 0 | 0 | 0 | 0 |
| 40 | 11.2100 | 0 | 0 | 2 | 0 | 1 | 2 | 0 | 2 | 2 | 1 | | | | | |
| 41 | 11.2100 | 0 | 0 | 1 | 0 | 2 | 2 | 0 | 2 | 2 | 2 | | | | | |
| 42 | 11.2100 | 0 | 0 | 2 | 0 | 0 | 1 | 0 | 2 | 2 | 2 | | | | | |
| 43 | 11.2100 | 0 | 0 | 2 | 1 | 2 | 1 | 0 | 2 | 1 | 1 | | | | | |
| 44 | 11.2100 | 0 | | | 0 | 2 | 0 | 2 | 1 | | | 0 | 0 | N | 0 | 0 |
| 45 | 11.2100 | 0 | 0 | 0 | 0 | 0 | 0 | 0 | 0 | 0 | 0 | | | | | |
| 46@ | 11.2100 | 0 | 0 | 2 | 0 | 2 | 2 | 1 | 2 | 2 | 2 | | | | | |
| 47@ | 11.2100 | 0 | 0 | 2 | 0 | 2 | 2 | 2 | 2 | 2 | 2 | | | | | |
| 48@ | 11.2100 | 0 | 0 | 2 | 0 | 0 | 2 | 1 | 2 | 2 | 2 | | | | | |
| 49@ | 11.2100 | 0 | 0 | 2 | 0 | 2 | 2 | 1 | 2 | 2 | 2 | | | | | |
| 50 | 11.2100 | 0 | 0 | 1 | 0 | 2 | 2 | 0 | 1 | 1 | 2 | | | | | |
| 51 | 11.2100 | 0 | 2 | 3 | 2 | 3 | 2 | 2 | 2 | 2 | 1 | | | | | |
| 52 | 11.2100 | 0 | 0 | 2 | 0 | 2 | 2 | 2 | 2 | 1 | 2 | | | | | |
| 53 | 11.2100 | 0 | 0 | 2 | 0 | 2 | 2 | 1 | 2 | 2 | 2 | | | | | |
| 54 | 11.2100 | 0 | 0 | 2 | 0 | 0 | 1 | 0 | 1 | 1 | 1 | | | | | |
| 55 | 11.2100 | 0 | 0 | 2 | 0 | 2 | 2 | 0 | 2 | 0 | 1 | | | | | |
| 56 | 11.2100 | 0 | 0 | 2 | 0 | 2 | 2 | 2 | 2 | 2 | 2 | | | | | |
| 57 | 11.2100 | 0 | 0 | 2 | 0 | 1 | 2 | 2 | 2 | 2 | 2 | | | | | |
| 58 | 11.2100 | 0 | 0 | 0 | 0 | 0 | 1 | 1 | 1 | 2 | 1 | | | | | |
| 59 | 11.2100 | 0 | 0 | 0 | 0 | 0 | 0 | 0 | 1 | 0 | 0 | | | | | |
| 60 | 11.2100 | 0 | 0 | 0 | 0 | 0 | 0 | 0 | 1 | 0 | 0 | | | | | |

*DAMPING OFF-IM,WB
POOR SMARTWEED GERMINATION
@DAMPING OFF-IM,WB POOR GERMINATION-CB

POST-EMERGENCE ACTIVITY ON WEEDS AND CROPS

Compounds of this invention were tested for herbicidal activity on weed plants in the presence of crop plants according to the following procedure:

Topsoil (silt loam) is sieved through a screen having 1.27 cm openings. In some of the tests the soil was mixed with fertilizer (1225 g/cm. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage, each pan (except the control pans) is removed to a spraying chamber and sprayed by means of an atomizer, operating at a spary pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mols of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10–14 days (usually 11 days) and in some instances observed again at 24–28 days (usually 25 days) after spraying. These latter observations are designated by a "pound" sign (#) following the column of example numbers in the Table.

In the following Table D the legends used to identify the plant species are the same as those used in the preceding Table B.

TABLE D

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 2 | 5.6050 | 1 | | | 1 | 2 | 0 | 1 | | 0 | 1 | 1 | 1 | 2 | 1 | 1 | 2 | 3 | 0 | 1 | 2 | N |
|  | 5.6050 | 3 | | | 2 | 2 | 1 | 3 | | 3 | 2 | 1 | 2 | 3 | 1 | 1 | 3 | 2 | 2 | 1 | 3 | N |
|  | 5.6050 | 2 | 3 | 3 | 3 | 3 | 3 | 3 | 3 | 4 | 2 | 2 | 3 | 3 | 2 | 3 | 3 | 4 | 2 | | | |
|  | 5.6050 | 2 | 2 | 3 | 2 | 3 | 2 | 2 | 2 | 2 | 2 | 1 | 2 | 3 | 1 | 2 | 2 | 3 | 2 | | | |
|  | 1.1210 | 2 | 2 | 2 | 2 | 3 | 3 | 3 | 2 | 3 | 0 | 0 | 2 | 3 | 1 | 0 | 3 | 3 | 2 | | | N |
|  | 1.1210 | 1 | 3 | 3 | 1 | 1 | 1 | 1 | | 0 | 1 | 0 | 1 | 2 | 0 | 0 | 1 | 1 | 0 | | | N |
|  | 1.1210 | 1 | | | 2 | 2 | 2 | 2 | | 2 | 0 | 0 | 0 | 2 | 0 | 0 | 2 | 2 | 2 | 1 | 1 | N |
|  | 1.1210 | 1 | | | 2 | 2 | 0 | 0 | | 0 | 0 | 0 | 2 | 2 | 1 | 0 | 0 | 2 | 0 | 1 | 2 | N |
|  | 0.5605 | 1 | | | 1 | 1 | 1 | 1 | | 1 | 0 | 0 | 1 | 2 | 0 | 0 | 1 | 2 | 2 | 0 | 1 | N |
|  | 0.5605 | 0 | | | 0 | 0 | 0 | 0 | | 0 | 0 | 0 | 0 | 1 | 0 | 0 | 0 | 0 | 0 | 0 | 0 | |
|  | 0.2803 | 1 | | | 1 | 0 | 1 | 0 | | 1 | 0 | 0 | 1 | 2 | 0 | 0 | 0 | 3 | 0 | 1 | 2 | N |
|  | 0.2803 | 2 | 2 | 2 | 2 | 2 | 2 | 2 | 2 | 2 | 0 | 0 | 1 | 2 | 0 | 0 | 0 | 3 | 0 | 1 | 1 | |
|  | 0.2803 | 2 | 3 | 3 | 2 | 2 | 2 | 3 | 2 | 3 | 0 | 0 | 0 | 2 | 0 | 0 | 0 | 3 | 2 | 0 | 0 | |
|  | 0.1401 | 1 | | | 2 | 1 | 1 | 1 | | 0 | 0 | 0 | 0 | 0 | 0 | 0 | 0 | 0 | 0 | | | |
|  | 0.1401 | 2 | 2 | 2 | 2 | 2 | 2 | 2 | | 2 | 0 | 0 | 0 | 2 | 0 | 0 | 0 | 3 | 0 | | | |
|  | 0.0701 | 1 | | | 0 | 0 | 0 | 0 | | 0 | 0 | 0 | 0 | 0 | 0 | 0 | 0 | 0 | 0 | | | |
|  | 0.0701 | 0 | | | 0 | 0 | 0 | 0 | | 0 | 0 | 0 | 0 | 0 | 0 | 0 | 0 | 0 | 0 | | | |
|  | 0.0701 | 1 | 2 | 2 | 0 | 0 | 0 | 3 | | 1 | 0 | 0 | 0 | 0 | 0 | 0 | 0 | 0 | 1 | | | |
|  | 0.0701 | 2 | 1 | 2 | 2 | 3 | 2 | 2 | 2 | 2 | 0 | 0 | 0 | 1 | 0 | 2 | 2 | 3 | 1 | | | 1 |
| 10 | 5.3808 | 2 | 2 | 2 | 2 | 3 | 3 | 3 | 3 | 3 | 0 | 0 | 0 | 3 | 2 | 2 | 0 | 3 | 1 | | | 2 |
|  | 5.3808 | 2 | 3 | 3 | 3 | 3 | 2 | 3 | 2 | 3 | 0 | 0 | 0 | 3 | 0 | 2 | 0 | 3 | 1 | | | 1 |
|  | 1.1210 | 2 | 2 | 2 | 2 | N | 2 | 2 | 2 | 2 | 0 | 0 | 0 | 0 | 0 | 0 | 0 | 3 | 0 | | | 1 |
|  | 1.1210 | 2 | 2 | 3 | 2 | 1 | 2 | 3 | 2 | 3 | 0 | 0 | 0 | 1 | 0 | 0 | 2 | 3 | 1 | | | 0 |
|  | 0.2803 | 1 | 2 | 2 | 2 | N | 1 | 2 | 2 | 2 | 0 | 0 | 0 | 0 | 0 | 0 | 0 | 3 | 1 | | | 0 |
|  | 0.2803 | 1 | 1 | 3 | 2 | 1 | 1 | 3 | 2 | 3 | 0 | 0 | 0 | 0 | 0 | 0 | 0 | 3 | 0 | | | 0 |
|  | 0.0701 | 0 | | | 0 | 0 | 1 | 1 | | 1 | 0 | 0 | 0 | 0 | 0 | 0 | 0 | 2 | 1 | | | |
|  | 0.0701 | 1 | 2 | 2 | 2 | 1 | 1 | 2 | 2 | 2 | 0 | 0 | 0 | 1 | 0 | 0 | 1 | 3 | 1 | | | |
| 12 | 11.2100 | 2 | | | 2 | 2 | 3 | 3 | 2 | 3 | 0 | 0 | 0 | 2 | 2 | 2 | 0 | 3 | 0 | | | 1 |
|  | 11.2100 | 3 | | | 3 | 3 | 2 | 3 | 3 | 3 | 0 | 0 | 2 | 3 | 2 | 2 | 2 | 3 | 2 | | | 2 |
|  | 8.4075 | 2 | | | 2 | 3 | 2 | 2 | 3 | 2 | 0 | 0 | 2 | 3 | 2 | 2 | 1 | 3 | 2 | | | 1 |
|  | 8.4075 | 1 | | | 3 | 3 | 2 | 3 | 3 | 3 | 1 | 1 | 0 | 3 | 0 | 0 | 1 | 3 | 1 | | | 1 |
|  | 5.6050 | 2 | | | 2 | 2 | 2 | 3 | 2 | 2 | 0 | 0 | 0 | 1 | 1 | 1 | 0 | 3 | 1 | | | 0 |
|  | 2.8025 | 1 | | | 2 | 1 | 1 | 2 | | 2 | 0 | 0 | 1 | 3 | 2 | 1 | 2 | 3 | 1 | | | 0 |
|  | 2.8025 | 1 | | | 2 | 1 | 2 | 3 | | 3 | 0 | 0 | 1 | 3 | 0 | 2 | 0 | 3 | 2 | | | 1 |
|  | 1.1210 | 1 | | | 2 | 1 | 1 | 2 | | 2 | 0 | 0 | 0 | 2 | 1 | 0 | 0 | 2 | 2 | | | 0 |
| 13 | 5.3808 | 3 | 3 | 3 | 3 | 0 | 3 | 3 | 3 | 3 | 0 | 0 | 0 | 3 | 0 | 0 | 0 | 3 | 0 | 1 | 1 | 0 |
|  | 5.3808 | 2 | 2 | 3 | 2 | N | 2 | 3 | 3 | 3 | 1 | 0 | 2 | 3 | 1 | 1 | 2 | 3 | 0 | 2 | 2 | 0 |
|  | 1.1210 | 2 | 2 | 3 | 3 | 2 | 2 | 3 | 2 | 3 | 0 | 0 | 2 | 3 | 0 | 2 | 2 | 3 | 0 | 1 | 1 | 0 |
|  | 1.1210 | 2 | 2 | 2 | 2 | 2 | 2 | 2 | 2 | 3 | 0 | 0 | 1 | 3 | 1 | 3 | 2 | 3 | 0 | 3 | 3 | 1 |
|  | 0.2803 | 2 | 1 | 2 | 2 | N | 2 | 3 | 2 | 3 | 0 | 0 | 2 | 3 | 0 | 2 | 2 | 3 | 0 | 1 | 1 | 0 |
|  | 0.2803 | 1 | 2 | 2 | 2 | 2 | 1 | 3 | 2 | 3 | 0 | 0 | 1 | 2 | 0 | 0 | 1 | 3 | 0 | 1 | 1 | 0 |
|  | 0.0701 | 2 | 2 | 2 | 2 | N | 2 | 2 | 2 | 2 | 0 | 0 | 0 | 2 | 0 | 0 | 0 | 3 | 0 | 0 | 2 | 0 |
|  | 0.0701 | 1 | 1 | 3 | 1 | 2 | 1 | 3 | | 3 | 1 | 0 | 0 | 3 | 0 | 0 | 2 | 3 | 0 | 1 | 1 | 0 |
| 22 | 5.0445 | 3 | 3 | 2 | 3 | 3 | 3 | 3 | 3 | 3 | 0 | 0 | 3 | 3 | 3 | N | 2 | 3 | 2 | | | 0 |
|  | 5.0445 | 3 | 2 | 2 | 2 | 3 | 2 | 3 | 3 | 3 | 0 | 2 | 2 | 3 | 2 | 2 | 2 | 3 | 0 | | | |
|  | 1.1210 | 2 | 2 | 2 | 2 | 3 | 2 | 2 | 2 | 2 | 0 | 0 | 2 | 3 | 1 | 0 | 2 | 3 | 0 | | | 0 |
|  | 0.2803 | 2 | 2 | 3 | 1 | 2 | 2 | 3 | 2 | 1 | 0 | 0 | 0 | 2 | 0 | 1 | 0 | 3 | 0 | | | 0 |

TABLE D-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| | 0.2803 | 2 | 1 | 2 | 2 | 2 | 2 | 2 | 2 | 1 | 0 | 0 | 0 | 2 | 0 | 1 | 0 | 3 | 1 | | | |
| | 0.0701 | 1 | 1 | 2 | 0 | 0 | 2 | 1 | 2 | 1 | 0 | 0 | 0 | 0 | 0 | 0 | 0 | 3 | 0 | | | |
| | 0.0701 | 2 | 2 | 2 | 0 | 1 | 2 | 2 | 2 | 1 | 0 | 0 | 0 | 0 | 0 | 0 | 0 | 2 | 0 | | | |
| 35 | 5.6050 | 3 | 2 | 2 | 2 | 3 | 2 | 3 | 3 | 3 | 0 | 0 | 0 | 0 | 0 | 2 | 0 | 3 | 2 | | | |
| | 5.6050 | 3 | 3 | 4 | 4 | 3 | 3 | 4 | 4 | 4 | 0 | 3 | 0 | 0 | 0 | 2 | 1 | 3 | 2 | | | |
| | 1.1210 | 3 | 2 | 2 | 2 | 4 | 2 | 4 | 3 | 3 | 0 | 2 | 0 | 2 | 0 | 1 | 0 | 3 | 2 | | | |
| | 1.1210 | 3 | 2 | 2 | 2 | 3 | 2 | 3 | 3 | 3 | 0 | 0 | 0 | 0 | 0 | 0 | 0 | 3 | 1 | | | |
| | 0.2803 | 1 | 2 | 3 | 0 | 0 | 0 | 2 | 3 | 2 | 0 | 0 | 0 | 2 | 2 | 0 | 0 | 3 | 0 | | | |
| 51* | 5.6050 | N | 2 | 3 | 1 | 2 | 2 | 2 | 4 | 3 | 0 | 0 | 0 | 2 | 1 | 0 | 1 | 2 | 2 | | | |
| * | 1.1210 | 1 | 1 | 2 | 0 | 1 | 1 | 1 | 3 | 1 | 0 | 0 | 0 | 0 | 0 | 1 | 0 | 2 | 1 | | | |
| * | 0.2803 | 0 | 0 | 1 | 0 | 0 | 0 | 1 | 2 | 1 | 0 | 0 | 0 | 0 | 0 | 0 | 0 | 1 | 0 | | | |

*Coded comments recorded only at the highest rate observed.

By way of comparison with compounds of this invention, the following compounds were prepared and their activity was tested. The herbicidal ratings are shown in the following table.

| Example | Name |
|---------|------|
| 61 | 3-pyridinecarboxylic acid, 6-(difluoromethyl)-4-(2-methylpropyl)-5-(4-morpholinylcarbonyl)-2-(trifluoromethyl)-, methyl ester |
| 62 | 3-pyridinecarboxylic acid, 2-(difluoromethyl)-4-(2-methylpropyl)-5-(4-morpholinylcarbonyl)-6-(trifluoromethyl)-, methyl ester |
| 63 | 3-pyridinecarboxylic acid, 5-(1-aziridinylcarbonyl)-2-(difluoromethyl)-4-(2-methylpropyl)-6-(trifluoromethyl)-, methyl ester |
| 64 | 3-pyridinecarbothioic acid, 6-(difluoromethyl)-5-[(4-iodo-1H—pyrazol-1-yl)carbonyl[-4-(2-methylpropyl)-2-(trifluoromethyl)-, S—methyl ester |
| 65 | 3-pyridinecarboxylic acid, 5-(1H—benzimidazol-1-ylcarbonyl)-6-(difluoromethyl)-4-(2-methylpropyl)-2-(trifluoromethyl)-, methyl ester |
| 66 | 3-pyridinecarboxylic acid, 6-(difluoromethyl)-5-[(4-iodo-1H—pyrazol-1-yl)-carbonyl]-4-(2-methylpropyl)-2-(trifluoromethyl)-, methyl ester |
| 67 | 3-pyridinecarboxylic acid, 5-[(4-bromo-3-methyl-1H—pyrazol-1-yl)carbonyl]-6-(difluoromethyl)-4-(2-methylpropyl)-2-(trifluoromethyl)-, methyl ester, mixture with methyl 5-[(4-bromo-5-methyl-1H—pyrazol-1-yl)carbonyl]-6-(difluoromethyl)-4-(2-methylpropyl)-2-(trifluoromethyl)-3-pyridinecarboxylate |
| 68 | 3-pyridinecarboxylic acid, 5-[[3,5-bis(trifluoromethyl)-1H—pyrazol-1-yl)carbonyl]-6-(difluoromethyl)-4-(2-methylpropyl)-2-(trifluoromethyl)-, methyl ester |
| 69 | 3-pyridinecarboxylic acid, 5-[(4-bromo-3,5-dimethyl-1H—pyrazol-1-yl)carbonyl]-6-(difluoromethyl)-4-(2-methylpropyl)-2-(trifluoromethyl)-, methyl ester |
| 70 | 3-pyridinecarbonyl chloride, 6-(difluoromethyl)-4-(2-methylpropyl)-5-(1H—pyrazol-1-ylcarbonyl)-2-(trifluoromethyl)- |
| 71 | 3-pyridinecarboxylic acid, 2-(difluoromethyl)-5-[(4-iodo-1H—pyrazol-1-yl)carbonyl]-4-(2-methylpropyl)-6-(trifluoromethyl)-, methyl ester |
| 72 | 3-pyridinecarboxylic acid, 5-[(4-bromo-3-methyl-1H—pyrazol-1-yl)carbonyl]-2-(difluoromethyl)-4-(2-methylpropyl)-6-(trifluoromethyl)-, methyl ester, mixture with methyl 5-[(4-bromo-5-methyl-1H—pyrazol-1-yl)carbonyl]-2-(difluoromethyl)-4-(2-methylpropyl)-6-(trifluoromethyl)-3-pyridinecarboxylate |
| 73 | 3-pyridinecarboxylic acid, 5-[(4-bromo-3,5-dimethyl-1H—pyrazol-1-yl)carbonyl]-2-(difluoromethyl)-4-(2-methylpropyl)-6-(trifluoromethyl)-, methyl ester |
| 74 | 3-pyridinecarboxylic acid, 5-[[3,5-bis(trifluoromethyl)-1H—pyrazol-1-yl]carbonyl]-2-(difluoromethyl)-4-(2-methylpropyl)-6-(trifluoromethyl)-, methyl ester |
| 75* | 3-pyridinecarboxylic acid, 2-(difluoromethyl)-4-[(1-methylethyl)amino]-5-(1H—pyrazol-1-ylcarbonyl)-6-(trifluoromethyl)-, methyl ester |
| 76* | 3-pyridinecarboxylic acid, 2-(difluoromethyl)-5-[(1H—imidazol-1-yl)carbonyl]-4-[(1-methylethyl)amino]-6-(trifluoromethyl)-, methyl ester |

*prior art compound

WEED-PLANT HERBICIDE ACTIVITY

The plant species usually regarded as weeds which are utilized in the following set of tests, are identified by letter headings above the columns in accordance with the following legend:

A - Canada Thistle*
B - Cocklebur
C - Velvetleaf
D - Morning Glory
E - Common Lambsquarters
F - Pennsylvania Smartweed
G - Yellow Nutsedge*
H - Quackgrass*
I - Johnsongrass*
J - Downy Brome
K - Barnyardgrass

*Grown from vegetative propagules

| Example No. | kg/ha | A | B | C | D | E | F | G | H | I | J | K |
|---|---|---|---|---|---|---|---|---|---|---|---|---|
| HERBICIDE DATA PREEMERGENCE HERBICIDE ACTIVITY FOR WEEDS ||||||||||||| 
| 61 | 11.2 | 0 | 0 | 1 | 0 | 3 | 1 | 0 | 3 | 0 | 0 | 3 |
| 62 | 11.2 | 0 | 0 | 1 | 3 | 3 | 3 | 0 | 3 | 3 | 3 | 3 |
| 63 | 11.2 | 0 | 0 | 2 | 1 | 3 | 0 | 0 | 3 | 0 | 2 | 3 |
| 64 | 11.2 | 0 | 0 | 0 | 0 | 3 | 1 | 0 | 0 | 0 | 0 | 3 |
| 65 | 11.2 | 0 | 0 | 0 | 0 | 0 | 0 | 0 | 0 | 0 | 0 | 0 |
| 66 | 11.2 | 1 | 0 | 1 | 1 | 3 | 3 | 0 | 3 | 0 | 3 | 3 |
| 67 | 11.2 | 0 | 0 | 0 | 2 | 0 | 3 | 0 | 0 | 1 | 0 | 3 |
| 68 | 11.2 | 0 | 0 | 0 | 3 | 3 | 2 | 1 | 0 | 0 | 0 | 3 |
| 69 | 11.2 | 0 | 0 | 0 | 0 | 0 | 0 | 0 | 0 | 0 | 0 | 3 |
| 70 | 11.2 | 0 | 0 | 0 | 0 | 2 | 1 | 0 | 0 | 0 | 0 | 3 |
| 71 | 11.2 | 0 | 1 | 3 | 2 | 3 | 3 | 1 | 3 | 3 | 3 | 3 |
| 72 | 11.2 | 0 | 0 | 1 | 2 | 3 | 3 | 0 | 3 | 3 | 3 | 3 |
| 73 | 11.2 | 0 | 0 | 1 | 1 | 3 | 3 | 1 | 3 | 0 | 3 | 3 |
| 74 | 11.2 | 3 | 0 | 1 | 1 | 2 | 0 | 1 | 0 | 3 | 3 | 3 |
| 75 | 11.2 | 3 | 2 | 3 | 3 | 3 | 3 | 3 | 3 | 3 | 3 | 3 |
| 76 | 11.2 | 2 | 0 | 3 | 3 | 3 | 3 | 0 | 3 | 3 | 3 | 3 |
| HERBICIDE DATA POSTEMERGENCE ACTIVITY FOR WEEDS |||||||||||||
| 61 | 11.2 | 0 | 0 | 0 | 0 | 0 | 0 | 0 | 0 | 0 | 0 | 0 |
| 62 | 11.2 | 1 | 1 | 0 | 0 | 0 | 0 | 0 | 0 | 0 | 0 | 0 |
| 63 | 11.2 | 0 | 0 | 0 | 0 | 0 | 0 | 0 | 0 | 0 | 0 | 0 |
| 64 | 11.2 | 0 | 0 | 0 | 0 | 0 | 0 | 0 | 0 | 0 | 0 | 0 |
| 65 | 11.2 | 0 | 0 | 0 | 0 | 0 | 0 | 0 | 0 | 0 | — | 0 |
| 66 | 11.2 | N | 0 | 0 | 0 | 0 | 0 | 0 | 0 | 0 | 0 | 0 |
| 67 | 11.2 | 0 | 0 | 0 | 0 | 0 | 0 | 0 | 0 | 0 | 0 | 0 |
| 68 | 11.2 | 0 | 0 | 0 | 0 | 1 | 0 | 0 | 0 | 0 | 0 | 0 |
| 69 | 11.2 | 0 | 0 | 0 | 0 | 0 | 0 | 0 | 0 | 0 | 0 | 0 |
| 70 | 11.2 | 0 | 0 | 1 | 0 | 0 | 0 | 0 | 0 | 0 | 0 | 1 |
| 71 | 11.2 | 0 | 2 | 1 | 1 | 0 | 1 | 0 | 0 | 0 | 0 | 0 |
| 72 | 11.2 | 0 | 0 | 0 | 0 | 0 | 0 | 0 | 0 | 0 | 0 | 1 |
| 73 | 11.2 | 0 | 0 | 0 | 0 | 0 | 0 | 0 | 0 | 0 | 0 | 0 |
| 74 | 11.2 | 0 | 0 | 0 | 0 | 0 | 0 | 0 | 0 | 0 | 0 | 0 |
| 75 | 11.2 | 0 | 0 | 1 | 0 | 0 | 0 | 0 | 0 | 0 | 0 | 0 |
| 76 | 11.2 | 0 | 1 | 0 | 0 | 0 | 0 | 0 | 0 | 0 | 0 | 0 |

The plant species used in the following comparative tests were as follows:

| | |
|---|---|
| L - Soybean | E - Lambsquarters |
| M - Sugarbeet | F - Smartweed |
| N - Wheat | C - Velvetleaf |
| O - Rice | J - Downy Brome |
| P - Sorghum | S - Panicum |
| B - Cocklebur | K - Barnyardgrass |
| Q - Wild Buckwheat | T - Crabgrass |
| D - Morning Glory | U - Green Foxtail |
| R - Hemp Sesbania | V - Corn |

HERBICIDE DATA
PREEMERGENCE ACTIVITY FOR WEEDS IN CROP PLANTS

| Example No. | kg/ha | L | M | N | O | P | B | Q | D | R | E | F | C | J | S | K | T | U | V |
|---|---|---|---|---|---|---|---|---|---|---|---|---|---|---|---|---|---|---|---|
| 61 | 5.6 | 1 | 1 | 1 | 1 | 1 | 0 | 2 | 1 | 1 | 3 | 1 | 0 | 3 | 3 | 2 | 3 | | |
|  | 1.12 | 0 | 1 | 0 | 0 | 0 | 0 | 2 | 0 | 0 | 0 | 0 | 0 | 0 | 0 | 1 | 1 | | |
|  | 0.28 | 0 | 0 | 0 | 0 | 0 | 0 | 0 | 0 | 0 | 0 | 0 | 0 | 0 | 0 | 0 | 0 | | |
| 62 | 5.6 | 3 | 3 | 0 | 2 | 3 | 1 | 2 | 3 | 3 | 3 | 2 | 0 | 3 | 3 | 3 | 3 | | |
|  | 1.12 | 0 | 0 | 0 | 0 | 2 | 0 | 2 | 1 | 1 | 3 | 2 | 0 | 3 | 3 | 3 | 3 | | |
|  | 0.28 | 0 | 1 | 0 | 0 | 0 | 0 | 2 | 1 | 0 | 2 | 1 | 0 | 1 | 2 | 2 | 3 | | |
|  | 0.056 | 0 | 0 | 0 | 0 | 0 | 0 | 1 | 2 | 0 | 2 | 0 | 0 | 1 | 1 | 0 | 0 | | |
|  | 0.0112 | 0 | 0 | 0 | 0 | 0 | 0 | N | 0 | 0 | 0 | 0 | 0 | 1 | 0 | 0 | 0 | | |
| 63 | 5.6 | 2 | 3 | 2 | 3 | 3 | 0 | 3 | 0 | 3 | 3 | 3 | 3 | — | 3 | 3 | 3 | 3 | 2 |
|  | 1.12 | 0 | 1 | 0 | 1 | 2 | 0 | 0 | 0 | 1 | 3 | 3 | 1 | — | 3 | 3 | 3 | 3 | 1 |
|  | 0.56 | 0 | 1 | 0 | 2 | 3 | 0 | 2 | 0 | 0 | 3 | 3 | 1 | — | 3 | 3 | 3 | 3 | 1 |
|  | 0.28 | 0 | 0 | 0 | 0 | 0 | 0 | 0 | 0 | 0 | 1 | 1 | 1 | — | 3 | 1 | 3 | 3 | 0 |
|  | 0.14 | 0 | 0 | 0 | 0 | 0 | 2 | 1 | 0 | 0 | 2 | 1 | 0 | — | 1 | 0 | 3 | 3 | 0 |
| 64 | 5.6 | 0 | 0 | 0 | 0 | 0 | 0 | 0 | 0 | 0 | 3 | 3 | 0 | 0 | 1 | 1 | 3 | 3 | 0 |
|  | 1.12 | 1 | N | 0 | 0 | 0 | 0 | 1 | 0 | 0 | 2 | 2 | 1 | 1 | 0 | N | 2 | 1 | 0 |
|  | 0.56 | N | N | N | N | N | N | N | N | N | N | N | N | N | N | N | N | N | N |
|  | 0.28 | 0 | N | 0 | 0 | 0 | 0 | 1 | 0 | 0 | N | 1 | 0 | 0 | 0 | 0 | 0 | 0 | 0 |
|  | 0.14 | 0 | 0 | 0 | 0 | 0 | 0 | N | 0 | 0 | 0 | 0 | 0 | 0 | N | 0 | 0 | 0 | 0 |
|  | 0.07 | 0 | 0 | 0 | 0 | 0 | 0 | N | 0 | 0 | N | 1 | 0 | 1 | 0 | 0 | 0 | 0 | 0 |
| 65 | 5.6 | 0 | N | 2 | 3 | 3 | 0 | N | 0 | 1 | 3 | 3 | 1 | 3 | 3 | 3 | 3 | 3 | 1 |
|  | 1.12 | 0 | 0 | 0 | 0 | 0 | 0 | 0 | 0 | 0 | 0 | 0 | 0 | 2 | 1 | 2 | 3 | 2 | 0 |
|  | 0.56 | 0 | 0 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 | 0 | 0 |
|  | 0.14 | 0 | 0 | 0 | 0 | 0 | 0 | 0 | 0 | 0 | 0 | 0 | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 | 0 | 0 |
|  | 0.035 | 0 | 0 | 0 | 0 | 0 | 0 | 0 | 0 | 0 | 0 | 0 | 0 | 0 | 0 | 0 | 0 | 0 | 0 |
|  | 0.0182 | 0 | 0 | 0 | 0 | 0 | 0 | 0 | 0 | 0 | 0 | 0 | 0 | 0 | 0 | 0 | 0 | 0 | 0 |
| 66 | 5.6 | 0 | 1 | 0 | 1 | 0 | 0 | 2 | 0 | 0 | 1 | 1 | 0 | 3 | 1 | 2 | 3 | 3 | 0 |
|  | 1.12 | 0 | 0 | 0 | 0 | 0 | 0 | 0 | 0 | 2 | 0 | N | 0 | 0 | 0 | 0 | 0 | 0 | 0 |
|  | 0.56 | 0 | 0 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 | 0 | 0 |
|  | 0.14 | 0 | 0 | 0 | 0 | 0 | 0 | 0 | 0 | 0 | 0 | 0 | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 | 0 | 0 |
| 67 | 5.6 | 0 | 1 | 3 | 3 | 3 | 0 | 0 | 0 | 1 | 0 | 3 | 1 | 3 | 3 | 3 | 0 | 3 | 0 |
|  | 1.12 | 0 | N | 0 | 0 | 1 | 0 | 0 | 0 | 1 | N | 0 | 1 | 0 | 0 | 1 | 0 | 0 | 0 |
|  | 0.56 | 0 | 0 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | N | 0 | 0 | N | 0 | 0 | 0 | 0 | 1 | 0 | 0 | 0 |
|  | 0.14 | 0 | 0 | 0 | 0 | 0 | 0 | 0 | 0 | 0 | 0 | N | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 | 0 | 0 |
| 68 | 5.6 | 0 | 0 | 0 | 0 | 0 | 0 | 0 | 0 | 0 | 0 | 0 | 0 | 2 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 | 0 | 0 |
|  | 0.56 | 0 | 0 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 | 0 | 0 |
|  | 0.14 | 0 | 0 | 0 | 0 | 0 | 0 | 0 | 0 | 0 | 0 | 0 | 0 | 0 | 0 | 0 | 0 | 0 | 0 |
| 69 | 5.6 | 0 | 0 | 0 | 2 | 3 | 0 | 0 | 0 | 0 | 0 | 1 | 1 | 1 | 2 | 3 | 3 | 3 | 0 |
|  | 1.12 | 0 | 0 | 0 | 0 | N | 0 | 1 | 0 | 0 | 0 | 0 | 0 | 0 | 0 | 0 | 0 | 0 | 0 |
|  | 0.56 | 0 | 0 | 0 | 0 | 2 | 0 | 0 | 0 | 0 | 0 | 0 | 0 | 0 | 0 | 0 | 0 | 0 | 0 |
|  | 0.28 | 0 | 0 | 0 | 0 | N | 0 | 0 | 0 | 0 | 0 | 0 | 0 | 0 | 0 | 0 | 0 | 0 | 0 |
|  | 0.14 | 0 | 0 | 0 | 0 | N | 0 | 0 | 0 | 0 | 0 | 0 | 0 | 0 | 0 | 0 | 0 | 0 | 0 |
| 70 | 5.6 | 1 | 3 | 3 | 3 | 3 | 0 | 3 | 2 | 3 | 3 | 3 | 3 | 3 | 3 | 3 | 3 | 3 | 2 |
|  | 1.12 | 1 | 3 | 2 | 3 | 3 | 0 | 3 | 0 | 3 | 3 | 3 | 2 | 3 | 3 | 3 | 3 | 3 | 2 |
|  | 0.56 | 0 | 1 | 1 | 2 | 2 | 0 | 1 | 0 | 1 | 3 | 3 | 1 | 3 | 3 | 3 | 3 | 3 | 1 |
|  | 0.28 | 0 | N | 0 | 0 | 0 | 0 | N | 0 | 0 | 3 | 3 | 2 | 3 | 3 | 2 | 3 | 3 | 0 |
|  | 0.14 | 0 | N | 0 | 0 | 0 | 0 | 2 | 0 | 0 | N | 1 | 0 | 2 | 1 | 1 | 3 | 3 | 0 |
|  | 0.07 | 0 | 0 | 0 | 0 | 0 | 0 | 0 | 0 | 0 | 0 | 0 | 0 | 0 | 0 | 0 | 3 | 3 | 0 |
|  | 0.035 | 0 | 0 | 0 | 0 | 0 | 0 | N | 0 | 0 | 1 | 0 | 0 | 0 | 0 | 0 | 0 | 0 | 0 |
|  | 0.0182 | 0 | 0 | 0 | 0 | 0 | 0 | 0 | 0 | 0 | 0 | 0 | 0 | 0 | 0 | 0 | 0 | 0 | 0 |
|  | 0.009 | 0 | 0 | 0 | 0 | 0 | 0 | 0 | 0 | 0 | 0 | 0 | 0 | 0 | 0 | 0 | 0 | 0 | 0 |
| 71 | 5.6 | 1 | 2 | 3 | 3 | 3 | 0 | 2 | 1 | 3 | 3 | 3 | 3 | 3 | 3 | 3 | 3 | 3 | 2 |
|  | 1.12 | 0 | 0 | 2 | 1 | 2 | 0 | 0 | 0 | 1 | 3 | 3 | 2 | 3 | 3 | 3 | 3 | 3 | 0 |
|  | 0.56 | 0 | 0 | 0 | 0 | 0 | 0 | 0 | 0 | 0 | 1 | 2 | 0 | 3 | 3 | 2 | 3 | 3 | 0 |
|  | 0.28 | 0 | 0 | 0 | 0 | 2 | 0 | 0 | 0 | 0 | 0 | 0 | 0 | 2 | 2 | 1 | 3 | 1 | 0 |
|  | 0.14 | 0 | 0 | 0 | 0 | 0 | 0 | 0 | 0 | 0 | N | 0 | 0 | 0 | 0 | 0 | 1 | 0 | 0 |
|  | 0.07 | 0 | 0 | 0 | 0 | 0 | 0 | 0 | 0 | 0 | 0 | 0 | 0 | 0 | 0 | 0 | 0 | 0 | 0 |
|  | 0.035 | 0 | 0 | 0 | 0 | 0 | 0 | 0 | 0 | 0 | 0 | 0 | 0 | 0 | 0 | 0 | 0 | 0 | 0 |
|  | 0.0182 | N | 0 | 0 | 0 | 0 | 0 | 0 | 0 | 0 | 0 | 0 | 0 | 0 | 0 | 0 | 0 | 0 | 0 |
| 72 | 5.6 | 0 | 1 | 0 | 0 | 3 | 0 | 1 | 0 | 0 | 2 | 2 | 1 | 3 | 3 | 3 | 3 | 3 | 0 |
|  | 1.12 | 0 | 0 | 0 | 0 | 0 | 0 | 0 | 0 | 0 | 0 | 0 | 0 | 2 | 3 | 0 | 3 | 2 | 0 |
|  | 0.56 | N | 0 | 0 | 0 | 0 | 0 | 0 | 0 | 0 | 0 | 0 | 0 | 0 | 0 | 0 | 3 | 0 | 0 |
|  | 0.28 | 0 | 0 | 0 | 0 | 0 | 0 | 0 | 0 | 0 | 0 | 0 | 0 | 0 | 0 | 0 | 0 | 0 | 0 |
|  | 0.14 | 0 | 0 | 0 | 0 | 0 | 0 | 0 | 0 | 0 | 0 | 0 | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 | 0 | 0 |
|  | 0.35 | 0 | 0 | 0 | 0 | 0 | 0 | 0 | 0 | 0 | 0 | 0 | 0 | 0 | 0 | 0 | 0 | 0 | 0 |
| 73 | 5.6 | 0 | 0 | 0 | 2 | 2 | 0 | 0 | 0 | 0 | 0 | 0 | 0 | 3 | 3 | 3 | 3 | 3 | 0 |
|  | 1.12 | 0 | 0 | 0 | 0 | 1 | 0 | 0 | 0 | 0 | 0 | 0 | 0 | 0 | 0 | 0 | 0 | 0 | 0 |
|  | 0.56 | 0 | 0 | 0 | 0 | 1 | 0 | 0 | 0 | 0 | 0 | 0 | 0 | 0 | 0 | 0 | 0 | 0 | 0 |
|  | 0.28 | 0 | 0 | 0 | 0 | 0 | 0 | N | 0 | 0 | N | 0 | 0 | 0 | 0 | 0 | 2 | 0 | 0 |
|  | 0.14 | 0 | 0 | 0 | 0 | 0 | 0 | 0 | 0 | 0 | 0 | 0 | 0 | 0 | 0 | 0 | 0 | 0 | 0 |

-continued

HERBICIDE DATA
PREEMERGENCE ACTIVITY FOR WEEDS IN CROP PLANTS

| Example No. | kg/ha | L | M | N | O | P | B | Q | D | R | E | F | C | J | S | K | T | U | V |
|---|---|---|---|---|---|---|---|---|---|---|---|---|---|---|---|---|---|---|---|
| | 0.07 | 0 | 0 | 0 | 0 | 0 | 0 | 0 | 0 | 0 | 0 | 0 | 0 | 0 | 0 | 0 | 0 | 0 | 0 |
| | 0.035 | 0 | 0 | 0 | 0 | 0 | 0 | 0 | 0 | 0 | 0 | 0 | 0 | 0 | 0 | 0 | 0 | 0 | 0 |
| 74 | 5.6 | 3 | 3 | 3 | 3 | 3 | 2 | 3 | 3 | 3 | 3 | 3 | 3 | 3 | 3 | 3 | 3 | — | — |
| | 1.12 | 3 | 3 | 3 | 3 | 3 | 0 | 3 | 3 | 3 | 3 | 3 | 3 | 3 | 3 | 3 | 3 | — | — |
| | 0.56 | 3 | 3 | 3 | 1 | N | 0 | 3 | 3 | 3 | 3 | 3 | 3 | 3 | 3 | 3 | 3 | — | — |
| | 0.28 | 3 | 3 | 2 | 1 | 3 | 0 | 3 | 3 | 3 | 3 | 3 | 3 | 3 | 3 | 3 | 3 | — | — |
| | 0.14 | 2 | 2 | 1 | 0 | 3 | 0 | 2 | 2 | 2 | 3 | 2 | 2 | 3 | 3 | 3 | 3 | — | — |
| | 0.07 | 0 | 2 | 0 | 0 | 2 | 0 | 2 | N | 1 | 3 | 2 | 2 | 3 | 3 | 3 | 3 | — | — |
| | 0.035 | 0 | 0 | 0 | 0 | 0 | 0 | 0 | 1 | 0 | 2 | 2 | 1 | 0 | 3 | 3 | 3 | — | — |
| | 0.0182 | 0 | 0 | 0 | 1 | 0 | 0 | 1 | 0 | 0 | 3 | 3 | 0 | — | 3 | 0 | 3 | 3 | 0 |
| | 0.009 | 0 | 0 | 0 | 0 | 0 | 0 | 0 | 0 | 0 | 0 | 0 | 0 | — | 1 | 0 | 2 | 3 | 0 |
| 75 | 5.6 | 2 | 2 | 0 | 0 | 1 | 1 | 0 | 3 | 3 | 3 | 2 | 1 | 2 | 2 | 3 | 3 | — | — |
| | 1.12 | 0 | 1 | 0 | 0 | 0 | 0 | 0 | 0 | 1 | 0 | 1 | 0 | 2 | 2 | 3 | 3 | — | — |
| | 0.28 | 0 | 0 | 0 | 0 | 0 | 0 | 0 | 0 | 0 | 0 | 0 | 0 | 1 | 0 | 1 | 0 | — | — |
| | 0.056 | 0 | 0 | 0 | 0 | 0 | 0 | 0 | 0 | 0 | 0 | 0 | 0 | 0 | 0 | 0 | 0 | — | — |
| | 0.0112 | 0 | 0 | 0 | 0 | 0 | 0 | 0 | 0 | 0 | 0 | 0 | 0 | 0 | 0 | 0 | 0 | — | — |

From these data, it can be seen that compounds claimed herein have activity which is markedly superior to closely related compounds, and that some are substantially equal to the prior art compound of Example 47.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers, imidazolinones and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-α:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazoin-2yl)-m-toluate and methyl 2-(4-isopropyl-4-methyl-5-oxo-2-imidazolin-2-yl)-p-toluate

Ureas

N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2-((4,6-dimethoxy pyrimidin-2-yl)aminocarbonyl)amino sulfonyl methyl) benzoate
Methyl-2-(((((4-methoxy-6-methyl-1,3,5-triazin-2-yl)amino)carbonyl)amino)sulfonyl) benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

Acetamides/Acetanilides/Anilines/Amides

2-Chloro-N,N-diallylacetamide
N,N-dimethyl-2,2-diphenylacetamide
N-[2,4-dimethyl-5-[[(trifluoromethyl)sulfonyl]amino]-phenyl]acetamide N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate

Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | | Weight Percent |
|---|---|---|
| I. Emulsifiable Concentrates | | |
| A. | Compound of Example No. 3 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 14 | 25.00 |
| | Free acid of complex organic phosphate of aromatic or aliphatic hydrophobe base | 5.00 |

| | Weight Percent |
|---|---|
| -continued | |
| (e.g., GAFAC RE-610) | |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |
| II. Flowables | |
| A. Compound of Example No. 24 | 25.00 |
| Methyl cellulose | 0.3 |
| Silica Aerogel | 1.5 |
| Sodium lignosulfonate | 3.5 |
| Sodium N—methyl-N—oleyl taurate | 2.0 |
| Water | 67.7 |
| | 100.00 |
| B. Compound of Example No. 18 | 45.0 |
| Methyl cellulose | .3 |
| Silica aerogel | 1.5 |
| Sodium lignosulfonate | 3.5 |
| Sodium N—methyl-N—oleyl taurate | 2.0 |
| Water | 47.7 |
| | 100.00 |
| III. Wettable Powders | |
| A. Compound of Example No. 5 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example 21 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 6 | 10.0 |
| Sodium lignosulfonate | 3.0 |
| Sodium N—methyl-N—oleyl-taurate | 1.0 |
| Kaolinite clay | 86.0 |
| | 100.00 |
| IV. Dusts | |
| A. Compound of Example No. 13 | 2.0 |
| Attapulgite | 98.0 |
| | 100.00 |
| B. Compound of Example No. 10 | 60.0 |
| Montmorillonite | 40.0 |
| | 100.00 |
| C. Compound of Example No. 30 | 30.0 |
| Ethylene glycol | 1.0 |
| Bentonite | 69.0 |
| | 100.00 |
| D. Compound of Example No. 27 | 1.0 |
| Diatomaceous earth | 99.0 |
| | 100.00 |
| V. Granules | |
| A. Compound of Example No. 17 | 15.0 |
| Granular attapulgite (20/40 mesh) | 85.0 |
| | 100.00 |
| B. Compound of Example No. 6 | 30.0 |
| Diatomaceous earth (20/40) | 70.0 |
| | 100.00 |
| C. Compound of Example No. 21 | 1.0 |
| Ethylene glycol | 5.0 |
| Methylene blue | 0.1 |
| Pyrophyllite | 93.9 |
| | 100.00 |
| D. Compound of Example No. 31 | 5.0 |
| Pyrophyllite (20/40) | 95.0 |
| | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

What is claimed is:

1. A compound represented by the formula

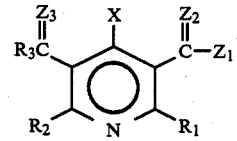

wherein:

$Z_1$ is selected from —SR, —OR,

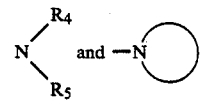

in which R is selected from the group consisting of hydrogen, lower alkyl, lower alkenyl, lower alkynyl, haloalkyl, haloalkenyl, and cyanoalkyl;

is selected from azetidinyl and a group derived from imidazole, pyrazole, pyrrole, triazole, or tetrazole, optionally substituted with up to 4 hydrogen atoms and up to 3 groups selected from lower alkyl, lower alkoxy, cyano, fluoro, chloro, nitro, haloalkyl, alkoxyalkyl, dialkoxyalkyl, hydroxyalkyl, and formyl, and the heterocyclic ring is connected to carbon at one of its nitrogen atoms, and $R_4$ and $R_5$ are selected from hydrogen and lower alkyl;

$Z_2$ is selected from O, S, and $NR_4$ in which $R_4$ is hydrogen or lower alkyl;

$Z_3$ is selected from O and $NR_4$;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

$R_3$ is

where

is as defined above; and

X is selected from lower alkyl, lower cycloalkyl, cycloalkylalkyl, alkoxyalkyl and alkylthio-alkyl.

2. A compound according to claim 1 in which R is lower alkyl.

3. A compound according to claim 2 wherein $Z_2$ and $Z_3$ are O.

4. A compound according to claim 3 in which one of $R_1$ and $R_2$ is trifluoromethyl and the other is difluoromethyl.

5. A compound according to claim 3 wherein X is selected from isobutyl, cyclobutyl, and cyclopropylmethyl.

6. A herbicidal composition containing an inert carrier and an effective amount of a composition represented by the formula

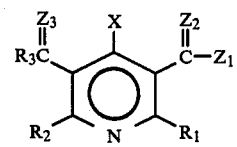

wherein:

$Z_1$ is selected from —SR, —OR,

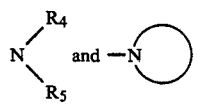

in which R is selected from the group consisting of hydrogen, lower alkyl, lower alkenyl, lower alkynyl, haloalkyl, haloalkenyl, and cyanoalkyl;

is selected from azetidinyl and a group derived from imidazole, pyrazole, pyrrole, triazole or tetrazole, optionally substituted with up to 4 hydrogen atoms and up to 3 groups selected from lower alkyl, lower alkoxy, cyano, fluoro, chloro, nitro, haloalkyl, alkoxyalkyl, dialkoxyalkyl, hydroxyalkyl, and formyl, and the heterocyclic ring is connected to carbon at one of its nitrogen atoms, and $R_4$ and $R_5$ are selected from hydrogen and lower alkyl;

$Z_2$ is selected from O, S, and $NR_4$ in which $R_4$ is hydrogen or lower alkyl;

$Z_3$ is selected from O and $NR_4$;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

$R_3$ is

where

is as defined above; and

X is selected from lower alkyl, lower cycloalkyl, cycloalkylalkyl, alkoxyalkyl and alkylthioalkyl.

7. A composition according to claim 6 in which R is lower alkyl.

8. A composition according to claim 7 wherein $Z_2$ and $Z_3$ are O.

9. A composition according to claim 8 in which one of $R_1$ and $R_2$ is trifluoromethyl and the other is difluoromethyl.

10. A composition according to claim 8 wherein X is selected from isobutyl, cyclobutyl, and cyclopropylmethyl.

11. A method of controlling the growth of vegetation comprising applying to the plant locus an effective amount of a compound represented by the formula

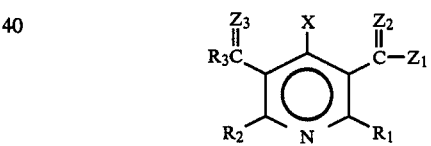

wherein:

$Z_1$ is selected from —SR, —OR,

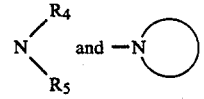

in which R is selected from the group consisting of hydrogen, lower alkyl, lower alkenyl, lower alkynyl, haloalkyl, haloalkenyl, and cyanoalkyl;

is selected from azetidinyl and a group derived from imidazole, pyrazole, pyrrole, triazole or tetrazole, optionally substituted with up to 4 hydrogen atoms and up to 3 groups selected from lower alkyl, lower alkoxy, cyano, fluoro, chloro, nitro, haloalkyl, alkoxyalkyl, dialkoxyalkyl, hydroxyalkyl, and formyl, and the heterocyclic ring is connected to carbon at one of its nitrogen atoms;

$Z_2$ is selected from O, S, and $NR_4$ in which $R_4$ is hydrogen or lower alkyl;

$Z_3$ is selected from O and $NR_4$;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

$R_3$ is

where

is as defined above; and

X is selected from lower alkyl, lower cycloalkyl, cycloalkylalkyl, alkoxyalkyl and alkylthioalkyl.

12. A compound according to claim 11 in which R is lower alkyl.

13. A compound according to claim 12 wherein $Z_2$ and $Z_3$ are O.

14. A compound according to claim 13 in which one of $R_1$ and $R_2$ is trifluoromethyl and the other is difluoromethyl.

15. A compound according to claim 13 wherein X is selected from isobutyl, cyclobutyl, and cyclopropylmethyl.

* * * * *